US011746149B2

(12) United States Patent
Kim et al.

(10) Patent No.: US 11,746,149 B2
(45) Date of Patent: Sep. 5, 2023

(54) USE OF ANTI-FAMILY WITH SEQUENCE SIMILARITY 19, MEMBER A5 ANTIBODIES FOR THE TREATMENT OF GLAUCOMA

(71) Applicant: Neuracle Science Co., Ltd., Seoul (KR)

(72) Inventors: Bongcheol Kim, Seongnam-si (KR); Dong Sik Kim, Seoul (KR); Soon-gu Kwon, Seoul (KR)

(73) Assignee: Neuracle Science Co., Ltd., Seoul (KR)

( * ) Notice: Subject to any disclaimer, the term of this patent is extended or adjusted under 35 U.S.C. 154(b) by 16 days.

(21) Appl. No.: 16/626,630

(22) PCT Filed: Jun. 27, 2018

(86) PCT No.: PCT/IB2018/054782
§ 371 (c)(1),
(2) Date: Dec. 26, 2019

(87) PCT Pub. No.: WO2019/003162
PCT Pub. Date: Jan. 3, 2019

(65) Prior Publication Data
US 2020/0157202 A1 May 21, 2020

Related U.S. Application Data

(60) Provisional application No. 62/582,889, filed on Nov. 7, 2017, provisional application No. 62/525,639, filed on Jun. 27, 2017.

(51) Int. Cl.
*A61K 39/395* (2006.01)
*A61K 39/00* (2006.01)
*C07K 16/24* (2006.01)

(52) U.S. Cl.
CPC ........ *C07K 16/24* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| 4,044,126 A | 8/1977 | Cook et al. |
| 4,364,923 A | 12/1982 | Cook et al. |
| 4,414,209 A | 11/1983 | Cook et al. |
| 5,693,780 A | 12/1997 | Newman et al. |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 9,579,398 B2 | 2/2017 | Seong et al. |
| 10,640,557 B2 | 5/2020 | Seong et al. |
| 11,155,613 B2 | 10/2021 | Kim et al. |
| 11,332,521 B2 | 5/2022 | Kim et al. |
| 11,560,425 B2 | 1/2023 | Kim et al. |
| 2004/0014194 A1 | 1/2004 | Beyer et al. |
| 2009/0221670 A1 | 9/2009 | Borglum et al. |
| 2012/0100140 A1 | 4/2012 | Reyes et al. |

(Continued)

FOREIGN PATENT DOCUMENTS

| EP | 2815769 A1 | 12/2014 |
| KR | 20160101786 A | 8/2016 |

(Continued)

OTHER PUBLICATIONS

Pennington and DeAngelis. Epigenetic Mechanisms of the Aging Human Retina. Journal of Experimental Neuroscience 2015:9(S2): 51-79. (Year: 2015).*
Busby et al. Systematic Comparison of monoclonal versus polyclonal antibodies for mapping histone modifications by ChIP-seq. bioRxiv, May 2016, p. 1-26. (Year: 2016).*
An, Z., et al., "IgG2m4, an Engineered Antibody Isotype with Reduced Fc Function," Mabs 1(6):572-579, Taylor & Francis, United States (Nov.-Dec. 2009).
Ashwell, K.W., et al., "The Appearance and Distribution of Microglia in the Developing Retina of the Rat," Visual Neuroscience 2(5):437-448, Cambridge University Press, England (May 1989).
Bird, R.E., et al., "Single-chain Antigen-binding Proteins," Science 242(4877):423-426, Association for the Advancement of Science, United States (Oct. 1988).

(Continued)

*Primary Examiner* — Maher M Haddad
(74) *Attorney, Agent, or Firm* — Sterne, Kessler, Goldstein & Fox P.L.L.C.

(57) ABSTRACT

The present disclosure relates to the pharmaceutical use of antagonists (e.g., an antibody or antigen-binding portion thereof) that specifically bind to FAM19A5 to treat a glaucoma in a subject in need thereof.

20 Claims, 5 Drawing Sheets

Specification includes a Sequence Listing.

(56) References Cited

U.S. PATENT DOCUMENTS

| | | | |
|---|---|---|---|
| 2015/0118230 A1* | 4/2015 | Seong | A61K 38/1709<br>424/135.1 |
| 2016/0060705 A1 | 3/2016 | O'Donnell et al. | |
| 2020/0299373 A1 | 9/2020 | Kim et al. | |

FOREIGN PATENT DOCUMENTS

| | | |
|---|---|---|
| WO | WO-9712622 A1 | 4/1997 |
| WO | WO-9817815 A1 | 4/1998 |
| WO | WO-9817816 A1 | 4/1998 |
| WO | WO-9818934 A1 | 5/1998 |
| WO | WO-9931251 A1 | 6/1999 |
| WO | WO-2015015000 A1 | 2/2015 |
| WO | WO-2019003162 A1 | 1/2019 |
| WO | WO-2019215702 A1 | 11/2019 |

OTHER PUBLICATIONS

Bosco, A., et al., "Early Microglia Activation in a Mouse Model of Chronic Glaucoma," The Journal of Comparative Neurology 519(4):599-620, Wiley-Liss, United States (Mar. 2011).

Bricogne, G., "Bayesian Statistical Viewpoint on Structure Determination: Basic Concepts and Examples," Methods in Enzymology 276:361-423, Academic Press, United States (Jan. 1997).

Bricogne, G., "Direct Phase Determination by Entropy Maximization and Likelihood Ranking: Status Report and Perspectives," Acta Crystallographica. Section D, Biological Crystallography 49(Pt1):37-60, Wiley-Blackwell, United States (Jan. 1993).

Champe, M., et al., "Monoclonal Antibodies that Block the Activity of Leukocyte Function-Associated Antigen 1 Recognize Three Discrete Epitopes in the Inserted Domain of CD11a," The Journal of Biological Chemistry 270 (3):1388-1394, American Society for Biochemistry and Molecular Biology, United States (Jan. 1995).

Chayen, N.E., et al., "The Role of Oil in Macromolecular Crystallization," Structure 5(10):1269-1274, Cell Press, United States (Oct. 1997).

Cheung, R.C., et al., "Epitope-specific Antibody Response to the Surface Antigen of Duck Hepatitis B Virus in Infected Ducks," Virology 176(2):546-552, Academic Press, United States (Jun. 1990).

Chothia, C. and Lesk, A.M., "Canonical Structures for the Hypervariable Regions of Immunoglobulins," Journal of Molecular Biology 196(4):901-917, Elsevier Science, United States (Aug. 1987).

Cunningham, B.C. and Wells, J.A., "High-resolution Epitope Mapping of hGH-receptor Interactions by Alanine-scanning Mutagenesis," Science 244(4908):1081-1085, American Association for the Advancement of Science, United States (Jun. 1989).

Edelman, G.M. et al., "The Covalent Structure of an Entire gammaG Immunoglobulin Molecule," Proceedings of the National Academy of Sciences USA 63(1):78-85, National Academy of Sciences, United States (May 1969).

Gieger, R., et al., "Crystallogenesis of Biological Macromolecules: Facts and Perspectives," Acta Crystallographica. Section D, Biological Crystallography 50(Pt4):339-350, Wiley-Blackwell, United States (Jul. 1994).

Gupta, D. and Chen P.P., "Glaucoma," American Family Physician 93(8):668-674, American Academy of General Practice, United States (Apr. 2016).

Harasymowycz, P., et al., "Medical Management of Glaucoma in the 21st Century from a Canadian Perspective," Journal of Ophthalmology 2016:6509809, Hindawi Publishing Corporation, United States (Nov. 2016).

Harmsen, M.M., et al., "Properties, Production, and Applications of Camelid Single-Domain Antibody Fragments," Applied Microbiology and Biotechnology 77(1):13-22, Springer International, Germany (Nov. 2007).

Huston, J.S., et al., "Protein Engineering of Antibody Binding Sites: Recovery of Specific Activity in an Anti-digoxin Single-chain Fv Analogue Produced in Escherichia coli," Proceedings of the National Academy of Sciences USA 85(16):5879-5883, National Academy of Sciences, United States (Aug. 1988).

International Search Report and Written Opinion for International Application No. PCT/IB2018/054782, European Patent Office, Rijswijk, dated Nov. 16, 2018, 12 pages.

Jefferis, R., et al., "Human Immunoglobulin Allotypes: Possible Implications for Immunogenicity," Mabs 1(4):332-338, Taylor & Francis, United States (Jul.-Aug. 2009).

Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (Dec. 1971).

Kettenmann, H, et al., "Physiology of Microglia," Physiological Reviews 91(2):461-553, American Physiological Society, United States (Apr. 2011).

Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (Dec. 1986).

Kostelny, S.A., et al., "Formation of a Bispecific Antibody by the Use of Leucine Zippers," The Journal of Immunology 148(5):1547-1553, American Association of Immunologists, United States (Mar. 1992).

Lau, C., et al., "Chimeric Anti-CD14 IGG2/4 Hybrid Antibodies for Therapeutic Intervention in Pig and Human Models of Inflammation," Journal of Immunology 91(9):4769-4777, American Association of Immunologists, United States(Nov. 2013).

Lee, B.L., et al., "The Glaucoma Symptom Scale. A Brief Index of Glaucoma-Specific Symptoms," Archives of Ophthalmology 116(7):861-866, American Medical Association, United States (Jul. 1998).

Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).

Lonberg, N., "Human Antibodies From Transgenic Animals," Nature Biotechnology, 23(9):1117-1125, Nature America Publishing, United States (Sep. 2005).

McCafferty, J., et al., "Phage Antibodies: Filamentous Phage Displaying Antibody Variable Domains," Nature 348(6301):552-554, Nature Publishing Group, London (Dec. 1990).

McPherson, A., "Crystallization of Proteins From Polyethylene Glycol," The Journal of Biological Chemistry 251(20):6300-6303, American Society for Biochemistry and Molecular Biology, United States (Oct. 1976).

McPherson, A., "Current Approaches to Macromolecular Crystallization," European Journal of Biochemistry 189(1):1-23, Blackwell Science Ltd, England (Apr. 1990).

Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, England (Aug. 1990).

Morel, G.A., et al., "Monoclonal Antibodies to Bovine Serum Albumin: Affinity and Specificity Determinations," Molecular Immunology 25(1):7-15, Pergamon Press, England (Jan. 1988).

Morris, G.E., "Epitope Mapping by Chemical Fragmentation," Methods in Molecular Biology 66:121-127, Humana Press, United States (Jan. 1996).

Ram, J. and Agarwal, A., "The Challenge of Childhood Cataract Blindness," The Indian Journal of Medical Research 140(4):472-474, Medknow, India (Oct. 2014).

Roux, K.H., et al., "Comparisons of the Ability of Human IgG3 Hinge Mutants, IgM, IgE, and IgA2, to form Small Immune Complexes: A Role for Flexibility and Geometry," The Journal of Immunology 161(8):4083-4090, American Association of Immunologists, United States (Oct. 1998).

Roversi, P., et al., "Modelling Prior Distributions of Atoms for Macromolecular Refinement and Completion," Acta Crystallographica. Section D, Biological Crystallography 56(Pt10):1316-1323, International Union of Crystallography by Munksgaard, United States (Oct. 2000).

(56) References Cited

OTHER PUBLICATIONS

Sanes, J.R., et al., "The Types of Retinal Ganglion Cells: Current Status and Implications for Neuronal Classification," Annual Review of Neuroscience 38:221-246, Annual Reviews, inc., United States (Jul. 2015).

Sommer, A., et al., "Relationship Between Intraocular Pressure and Primary Open Angle Glaucoma Among White and Black Americans. The Baltimore Eye Survey," Archives of Ophthalmology 109(8):1090-1095, American Medical Association, United States (Aug. 1991).

Songsivilai, S. and Lachmann, P.J., "Bispecific Antibody: A Tool for Diagnosis and Treatment of Disease," Clinical and Experimental Immunology 79(3):315-321, Blackwell Scientific Publications, England (Mar. 1990).

Stahli, C., et al., "Distinction of Epitopes by Monoclonal Antibodies," Methods in Enzymology 92:242-253, Academic Press, United States (Jan. 1983).

Tang, T.Y., et al., "TAFA: A Novel Secreted Family With Conserved Cysteine Residues and Restricted Expression in the Brain," Genomics 83(4):727-734, Academic Press, United States (Apr. 2004).

Tezel, G., et al., "TNF-Alpha and TNF-Alpha Receptor-1 in the Retina of Normal and Glaucomatous Eyes," Investigative Ophthalmology & Visual Science 42(8):1787-1794, Association for Research in Vision and Ophthalmology, United States (Jul. 2001).

Vidarsson, G., et al., "IgG Subclasses and Allotypes: from Structure to Effector Functions," Frontiers in Immunology 5(Article 520):17 pages, Lausanne : Frontiers Research Foundation, Switzerland (Oct. 2014).

Vohra, R., et al., "The Role of Inflammation in the Pathogenesis of Glaucoma," Survey of Ophthalmology 58(4):311-320, Elsevier Science, United States (Jul.-Aug. 2013).

Wang, W.H., et al., "Increased Expression of Serum Amyloid a in Glaucoma and Its Effect on Intraocular Pressure," Investigative Ophthalmology & Visual Science 49(5):1916-1923, Association for Research in Vision and Ophthalmology, United States (May 2008).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

Wilsey, L.J. and Fortune, B., "Electroretinography in Glaucoma Diagnosis," Current Opinion in Ophthalmology 27(2):118-124, Lippincott Williams & Wilkins, United States (Mar. 2016).

\* cited by examiner

USE OF ANTI-FAMILY WITH SEQUENCE SIMILARITY 19, MEMBER A5 ANTIBODIES FOR THE TREATMENT OF GLAUCOMA

REFERENCE TO SEQUENCE LISTING SUBMITTED ELECTRONICALLY

The content of the electronically submitted sequence listing in ASCII text file (Name: 3763_0060002_SeqListing_ST25.txt; Size: 167,256 bytes; and Date of Creation: Mar. 9, 2022) filed with the application is incorporated herein by reference in its entirety.

FIELD OF THE DISCLOSURE

The present disclosure provides methods for the treatment of glaucoma in a subject (e.g., a human) using antibodies that specifically bind to family with sequence similarity 19, member A5 (FAM19A5), or an antigen binding fragment thereof, or a composition comprising such antibodies or antigen binding fragment thereof.

BACKGROUND OF THE DISCLOSURE

Glaucoma is an ocular disorder characterized by structural changes at the optic nerve head of the retina (e.g., progressive loss of retinal ganglion cells (RGC) and cupping of the disk), resulting in vision impairment. Vohra et al., *Surv Ophthalmol* 58(4): 311-20 (2013). If left untreated, glaucoma can lead to permanent blindness. While the elderly are generally at a greater risk, glaucoma can affect individuals of all ages, including newborns. Ram et al., *Indian J Med Res* 140(4): 472-474 (2014). By 2020, it is estimated that approximately 79.6 million individuals worldwide will have glaucoma, with more than 11 million individuals being bilaterally blind from glaucoma. Gupta et al., *Am Fam Physician* 93(8): 668-674 (2016).

A major risk factor for glaucoma is thought to be elevated intraocular pressure (IOP), resulting from increased fluid pressure within the eyes. Accordingly, many of the treatment options that are currently available (e.g., (i) eye drops: prostaglandins, beta blockers, alpha-adrenergic agonists, and miotic or cholinergic agents; (ii) oral medications: carbonic anhydrase inhibitor; or (iii) surgery: laser therapy) focus primarily on reducing the elevated intraocular pressure. Harasymowycz et al., *J Ophthalmol* 2016: 6509809 (2016). However, such treatment options have numerous undesirable side effects (e.g., irregular heart rate, abnormal blood pressure, blurred vision, impotence, fatigue, pain, and/or discomfort). Moreover, while elevated intraocular pressure is a risk factor for glaucoma, many glaucoma patients can have normal intraocular pressure (i.e., normal tension glaucoma). Sommer et al., *Arch Ophthalmol* 109(8): 1090-1095 (1991). Therefore, there is a need for a more effective and comprehensive treatment option for glaucoma.

The two most common forms of glaucoma are (1) open-angle glaucoma (OAG) and (2) closed-angle glaucoma, with OAG being approximately seven times more common. Gupta et al., *Am Fam Physician* 93(8): 668-674 (2016). While the exact causes of glaucoma have yet to be fully elucidated, animals studies have shown a strong link between inflammation and the structural damages associated with glaucoma (e.g., loss of retinal ganglion cells). Tezel et al., *Invest Ophthalmol Vis Sci* 42: 1787-1794 (2001); Wang et al., *Invest Ophthalmol Vis Sci* 49: 1916-1923 (2008).

Provided herein are methods of treating glaucoma in a subject in need thereof using an antagonist against the FAM19A5 protein. In a specific embodiment, the FAM19A5 antagonist treats the subject by reducing, ameliorating, or inhibiting inflammation associated with the glaucoma.

BRIEF SUMMARY OF THE DISCLOSURE

Provided herein is an antagonist against a family with sequence similarity 19, member A5 ("FAM19A5") protein ("FAM19A5 antagonist") for treating a glaucoma in a subject in need thereof. Also provided herein is an FAM19A5 antagonist for reducing, ameliorating, or inhibiting inflammation associated with a glaucoma in a subject in need thereof.

In some embodiments, the glaucoma is selected from the group consisting of an open-angle glaucoma, angle-closure glaucoma, normal-tension glaucoma ("NTG"), congenital glaucoma, secondary glaucoma, pigmentary glaucoma, pseudoexfoliative glaucoma, traumatic glaucoma, neovascular glaucoma, irido corneal endothelial syndrome, and uveitic glaucoma. In some embodiments, the glaucoma is associated with an optic nerve damage, a retinal ganglion cell ("RGC") loss, a high intraocular pressure ("IOP"), an impaired blood-retina barrier, and/or an increase in a level of microglia activity within a retina and/or optic nerve of the subject. In some embodiments, the glaucoma is caused by a mechanical damage to an optic nerve head and/or an increase in a level of inflammation within a retina and/or an optic nerve of the subject.

In some embodiments, the FAM19A5 antagonist disclosed herein (i) delays an onset of retinal nerve cell degeneration within the subject; (ii) reduces a level of inflammation within the retina and/or optic nerve of the subject; (iii) increases a frequency of reduces the loss of retinal ganglion cells or restores the number of retinal ganglion cells within a ganglion cell layer of the retina of the subject; or (iv) any combinations thereof.

In some embodiments, the FAM19A5 antagonist is an antisense oligonucleotide, siRNA, shRNA, miRNA, dsRNA targeting FAM19A5, aptamer, PNA, or a vector including the same.

In some embodiments, the FAM19A5 antagonist is an antibody, or an antigen-binding portion thereof, that specifically binds to the FAM19A5 protein ("anti-FAM19A5 antibody").

In some embodiments, the anti-FAM19A5 antibody comprises a heavy chain CDR1, CDR2, and CDR3, and a light chain CDR1, CDR2, and CDR3, wherein the heavy chain CDR1, CDR2, and CDR3 comprises SEQ ID NOs: 11, 12, and 13, respectively, and the light chain CDR1, CDR2, and CDR3 comprises SEQ ID NOs: 23, 24, and 25, respectively. In other embodiments, the anti-FAM19A5 antibody comprises a heavy chain CDR1, CDR2, and CDR3, and a light chain CDR1, CDR2, and CDR3, wherein the heavy chain CDR1, CDR2, and CDR3 comprises SEQ ID NOs: 14, 15, and 16, respectively, and the light chain CDR1, CDR2, and CDR3 comprises SEQ ID NOs: 26, 27, and 28, respectively. In further embodiments, the anti-FAM19A5 antibody comprises a heavy chain CDR1, CDR2, and CDR3, and a light chain CDR1, CDR2, and CDR3, wherein the heavy chain CDR1, CDR2, and CDR3 comprises SEQ ID NOs: 17, 18, and 19, respectively, and the light chain CDR1, CDR2, and CDR3 comprises SEQ ID NOs: 29, 30, and 31, respectively. In certain embodiments, the anti-FAM19A5 antibody comprises a heavy chain CDR1, CDR2, and CDR3, and a light chain CDR1, CDR2, and CDR3, wherein the heavy chain CDR1, CDR2, and CDR3 comprises SEQ ID NOs: 20, 21, and 22, respectively, and the light chain CDR1, CDR2, and CDR3 comprises SEQ ID NOs: 32, 33, and 34, respectively.

In some embodiments, the anti-FAM19A5 antibody comprises a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 35, 36, 37, or 38; and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 39, 40, 41, or 42.

In some embodiments, the anti-FAM19A5 antibody is a chimeric antibody, a human antibody, or a humanized antibody.

In some embodiments, the FAM19A5 antagonist is administered intravitreally. In some embodiments, the subject is a human.

EMBODIMENTS

Embodiment 1. A method for treating a glaucoma in a subject in need thereof comprising administering to the subject an antagonist against a family with sequence similarity 19, member A5 ("FAM19A5") protein.

Embodiment 2. A method of reducing, ameliorating, or inhibiting inflammation associated with a glaucoma in a subject in need thereof comprising administering to the subject an antagonist against a family with sequence similarity 19, member A5 ("FAM19A5") protein.

Embodiment 3. The method of Embodiment 1 or 2, wherein the glaucoma is selected from the group consisting of an open-angle glaucoma, angle-closure glaucoma, normal-tension glaucoma ("NTG"), congenital glaucoma, secondary glaucoma, pigmentary glaucoma, pseudoexfoliative glaucoma, traumatic glaucoma, neovascular glaucoma, irido corneal endothelial syndrome, and uveitic glaucoma.

Embodiment 4. The method of any one of Embodiments 1 to 3, wherein the glaucoma is associated with an optic nerve damage, a retinal ganglion cell ("RGC") loss, a high intraocular pressure ("TOP"), an impaired blood-retina barrier, and/or an increase in a level of microglia activity within a retina and/or optic nerve of the subject.

Embodiment 5. The method of any one of Embodiments 1 to 4, wherein the glaucoma is caused by a mechanical damage to an optic nerve head and/or an increase in a level of inflammation within a retina and/or an optic nerve of the subject.

Embodiment 6. The method of any one of Embodiments 1 to 5, wherein the antagonist delays an onset of retinal nerve cell degeneration within the subject.

Embodiment 7. The method of any one of Embodiments 1 to 6, wherein the antagonist reduces a level of inflammation within the retina and/or optic nerve of the subject.

Embodiment 8. The method of any one of Embodiments 1 to 7, wherein the antagonist increases a frequency of reduces the loss of retinal ganglion cells or restores the number of retinal ganglion cells within a ganglion cell layer of the retina of the subject.

Embodiment 9. The method of any one of Embodiments 1 to 8, wherein the antagonist is an antisense oligonucleotide, siRNA, shRNA, miRNA, dsRNA targeting FAM19A5, aptamer, PNA, or a vector including the same.

Embodiment 10. The method of any one of Embodiments 1 to 8, wherein the antagonist is an antibody, or an antigen-binding portion thereof, that specifically binds to the FAM19A5 protein ("an anti-FAM19A5 antibody or antigen-binding portion thereof"), a polynucleotide encoding the anti-FAM19A5 antibody or antigen-binding portion thereof, or a vector comprising the polynucleotide thereof.

Embodiment 11. The method of Embodiment 10, wherein the anti-FAM19A5 antibody or antigen-binding portion thereof exhibits a property selected from:
  (a) binds to soluble human FAM19A5 with a KD of 10 nM or less as measured by enzyme-linked immunosorbent assay (ELISA);
  (b) binds to membrane bound human FAM19A5 with a KD of 1 nM or less as measured by ELISA; and
  (c) both (a) and (b).

Embodiment 12. The method of Embodiment 10 or 11, wherein the anti-FAM19A5 antibody or antigen-binding portion thereof cross-competes for binding to a human FAM19A5 epitope with a reference antibody comprising heavy chain CDR1, CDR2, and CDR3 and light chain CDR1, CDR2, and CDR3,
  (i) wherein the heavy chain CDR1 comprises the amino acid sequence of SEQ ID NO: 11, the heavy chain CDR2 comprises the amino acid sequence of SEQ ID NO: 12, the heavy chain CDR3 comprises the amino acid sequence of SEQ ID NO: 13, the light chain CDR1 comprises the amino acid sequence of SEQ ID NO: 23, the light chain CDR2 comprises the amino acid sequence of SEQ ID NO: 24, and the light chain CDR3 comprises the amino acid sequence of SEQ ID NO: 25;
  (ii) wherein the heavy chain CDR1 comprises the amino acid sequence of SEQ ID NO: 14, the heavy chain CDR2 comprises the amino acid sequence of SEQ ID NO: 15, the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28;
  (iii) wherein the heavy chain CDR1 comprises the amino acid sequence of SEQ ID NO: 17, the heavy chain CDR2 comprises the amino acid sequence of SEQ ID NO: 18, the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; or
  (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34.

Embodiment 13. The method of any one of Embodiments 10 to 12, wherein the anti-FAM19A5 antibody or antigen-binding portion thereof specifically binds to the same FAM19A5 epitope as a reference antibody comprising heavy chain CDR1, CDR2, and CDR3 and light chain CDR1, CDR2, and CDR3,
  (i) wherein the heavy chain CDR1 comprises the amino acid sequence of SEQ ID NO: 11, the heavy chain CDR2 comprises the amino acid sequence of SEQ ID NO: 12, the heavy chain CDR3 comprises the amino acid sequence of SEQ ID NO: 13, the light chain CDR1 comprises the amino acid sequence of SEQ ID NO: 23, the light chain CDR2 comprises the amino acid sequence of SEQ ID NO: 24, and the light chain CDR3 comprises the amino acid sequence of SEQ ID NO: 25;

(ii) wherein the heavy chain CDR1 comprises the amino acid sequence of SEQ ID NO: 14, the heavy chain CDR2 comprises the amino acid sequence of SEQ ID NO: 15, the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28;

(iii) wherein the heavy chain CDR1 comprises the amino acid sequence of SEQ ID NO: 17, the heavy chain CDR2 comprises the amino acid sequence of SEQ ID NO: 18, the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; or (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34.

Embodiment 14. The method of any one of Embodiments 10 to 13, wherein the anti-FAM19A5 antibody or antigen-binding portion thereof specifically binds to at least one FAM19A5 epitope, which is SEQ ID NO: 6 or SEQ ID NO: 9.

Embodiment 15. The method of any one of Embodiments 10 to 13, wherein the anti-FAM19A5 antibody or antigen-binding portion thereof binds only to an FAM19A5 epitope, which is SEQ ID NO: 6 or SEQ ID NO: 9.

Embodiment 16. The method of any one of Embodiments 10 to 14, wherein the anti-FAM19A5 antibody or antigen-binding portion thereof further binds to an additional FAM19A5 epitope.

Embodiment 17. The method of Embodiment 16, wherein the additional FAM19A5 epitope is selected from the group consisting of SEQ ID NO: 5, SEQ ID NO: 6, SEQ ID NO: 7, SEQ ID NO: 8, SEQ ID NO: 9, SEQ ID NO: 10, and any combination thereof.

Embodiment 18. The method of any one of Embodiments 10 to 17, wherein the anti-FAM19A5 antibody or antigen-binding portion thereof comprises a heavy chain CDR1, CDR2, and CDR3 and a light chain CDR1, CDR2, and CDR3.

Embodiment 19. The method of Embodiment 18, wherein the heavy chain CDR3 of the anti-FAM19A5 antibody or antigen-binding portion thereof comprises the amino acid sequence of SEQ ID NO: 13, SEQ ID NO: 16, SEQ ID NO: 19, or SEQ ID NO: 22.

Embodiment 20. The method of Embodiment 18 or 19, wherein the heavy chain CDR1 of the anti-FAM19A5 antibody or antigen-binding portion thereof comprises the amino acid sequence of SEQ ID NO: 11, SEQ ID NO: 14, SEQ ID NO: 17, or SEQ ID NO: 20.

Embodiment 21. The method of any one of Embodiments 18 to 20, wherein the heavy chain CDR2 of the anti-FAM19A5 antibody or antigen-binding portion thereof comprises the amino acid sequence of SEQ ID NO: 12, SEQ ID NO: 15, SEQ ID NO: 18, or SEQ ID NO: 21.

Embodiment 22. The method of any one of Embodiments 18 to 21, wherein the light chain CDR1 of the anti-FAM19A5 antibody or antigen-binding portion thereof comprises the amino acid sequence of SEQ ID NO: 23, SEQ ID NO: 26, SEQ ID NO: 29, or SEQ ID NO: 32.

Embodiment 23. The method of any one of Embodiments 18 to 22, wherein the light chain CDR2 of the anti-FAM19A5 antibody or antigen binding portion thereof comprises the amino acid sequence of SEQ ID NO: 24, SEQ ID NO: 27, SEQ ID NO: 30, or SEQ ID NO: 33.

Embodiment 24. The method of any one of Embodiments 18 to 23, wherein the light chain CDR3 of the anti-FAM19A5 antibody or antigen binding portion thereof comprises the amino acid sequence of SEQ ID NO: 25, SEQ ID NO: 28, SEQ ID NO: 31, or SEQ ID NO: 34.

Embodiment 25. The method of any one of Embodiments 10 to 24, wherein the anti-FAM19A5 antibody or antigen-binding portion thereof comprises a heavy chain CDR1, CDR2, and CDR3, and a light chain CDR1, CDR2, and CDR3, wherein (i) the heavy chain CDR1, CDR2, and CDR3 comprises SEQ ID NOs: 11, 12, and 13, respectively, and the light chain CDR1, CDR2, and CDR3 comprises SEQ ID NOs: 23, 24, and 25, respectively;

(ii) the heavy chain CDR1, CDR2, and CDR3 comprises SEQ ID NOs: 14, 15, and 16, respectively, and the light chain CDR1, CDR2, and CDR3 comprises SEQ ID NOs: 26, 27, and 28, respectively;

(iii) the heavy chain CDR1, CDR2, and CDR3 comprises SEQ ID NOs: 17, 18, and 19, respectively, and the light chain CDR1, CDR2, and CDR3 comprises SEQ ID NOs: 29, 30, and 31, respectively; or (iv) the heavy chain CDR1, CDR2, and CDR3 comprises SEQ ID NOs: 20, 21, and 22, respectively, and the light chain CDR1, CDR2, and CDR3 comprises SEQ ID NOs: 32, 33, and 34, respectively.

Embodiment 26. The method of any one of Embodiments 10 to 25, wherein the anti-FAM19A5 antibody or antigen-binding portion thereof comprises a heavy chain variable domain comprising SEQ ID NO: 35, SEQ ID NO: 36, SEQ ID NO: 37, or SEQ ID NO: 38 and/or a light chain variable domain comprising SEQ ID NO: 39, SEQ ID NO: 40, SEQ ID NO: 41, or SEQ ID NO: 42.

Embodiment 27. The method of Embodiment 26, wherein the anti-FAM19A5 antibody or antigen-binding portion thereof comprises a heavy chain variable domain comprising SEQ ID NO: 35 and a light chain variable domain comprising SEQ ID NO: 39.

Embodiment 28. The method of Embodiment 26, wherein the anti-FAM19A5 antibody or antigen-binding portion thereof comprises a heavy chain variable domain comprising SEQ ID NO: 36 and a light chain variable domain comprising SEQ ID NO: 40.

Embodiment 29. The method of Embodiment 26, wherein the anti-FAM19A5 antibody or antigen-binding portion thereof comprises a heavy chain variable domain comprising SEQ ID NO: 37 and a light chain variable domain comprising SEQ ID NO: 41.

Embodiment 30. The method of Embodiment 31, wherein the anti-FAM19A5 antibody or antigen-binding portion thereof comprises a heavy chain variable domain comprising SEQ ID NO: 38 and a light chain variable domain comprising SEQ ID NO: 42.

Embodiment 31. The method of any one of Embodiments 10 to 25, wherein the anti-FAM19A5 antibody or antigen-binding portion thereof comprises a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 35, 36, 37, or 38.

Embodiment 32. The method of any one of Embodiments 10 to 25, wherein the anti-FAM19A5 antibody or antigen-binding portion thereof comprises a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 39, 40, 41, or 42.

Embodiment 33. The method of any one of Embodiments 10 to 25, wherein the anti-FAM19A5 antibody or antigen-binding portion thereof comprises a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 35, 36, 37, or 38; and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 39, 40, 41, or 42.

Embodiment 34. The method of any one of Embodiments 10 to 33, wherein the anti-FAM19A5 antibody is a chimeric antibody, a human antibody, or a humanized antibody.

Embodiment 35. The method of any one of Embodiments 10 to 33, wherein the antigen-binding portion thereof is an Fab, an Fab', an F(ab')2, an Fv, or a single chain Fv (scFv).

Embodiment 36. The method of any one of Embodiments 10 to 35, wherein the anti-FAM19A5 antibody or antigen-binding portion thereof is selected from the group consisting of an IgG1, an IgG2, an IgG3, an IgG4, and a variant thereof.

Embodiment 37. The method of Embodiment 36, wherein the anti-FAM19A5 antibody or antigen-binding portion thereof is an IgG2, an IgG4, or a combination thereof.

Embodiment 38. The method of Embodiment 36, wherein the anti-FAM19A5 antibody or antigen-binding portion thereof comprises an IgG2/IgG4 isotype antibody.

Embodiment 39. The method of any one of Embodiments 10 to 38, wherein the anti-FAM19A5 antibody or antigen-binding portion thereof further comprises a constant region without the Fc function.

Embodiment 40. The method of any one of Embodiments 10 to 39, wherein the anti-FAM19A5 antibody or antigen-binding portion thereof is linked to a molecule having a second binding moiety, thereby forming a bispecific molecule.

Embodiment 41. The method of any one of Embodiments 10 to 40, wherein the anti-FAM19A5 antibody or antigen-binding portion thereof is linked to an agent, thereby forming an immunoconjugate.

Embodiment 42. The method of any one of Embodiments 1 to 41, wherein the antagonist of the FAM19A5 protein is formulated with a pharmaceutically acceptable carrier.

Embodiment 43. The method of any one of Embodiments 1 to 42, wherein the antagonist of the FAM19A5 protein is administered intravitreally.

Embodiment 44. The method of any one of Embodiments 1 to 43, wherein the subject is a human.

BRIEF DESCRIPTION OF THE DRAWINGS

FIG. 3A shows the RGC cell count both as an absolute number (left panel) and as a percentage of the total number of cells observed (right panel). Data are expressed as mean±S.D. "*" above the bars indicates a statistically significant difference ($p<0.05$) compared to IgG1-treated animals. FIG. 3B shows the fluorescent imaging (at 100× magnification) of the retinal ganglion cell layer from a representative animal in each of the groups.

DETAILED DESCRIPTION OF THE DISCLOSURE

Figure 1:
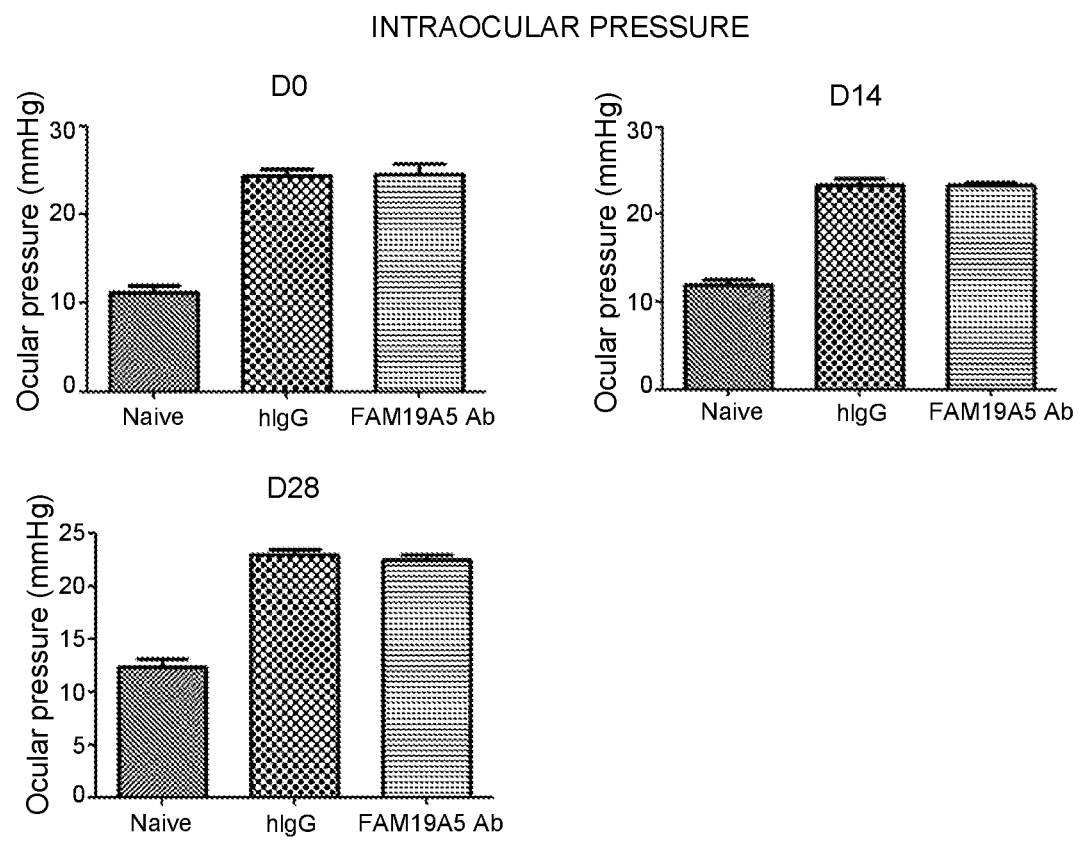
FIG. 1 shows a comparison of the intraocular pressure in glaucoma-induced animals treated with human IgG1 ("hIgG") or an anti-FAM19A5 antibody ("FAM19A5 Ab") against healthy animals (i.e., no glaucoma induction) ("naive"). The intraocular pressure was measured at day 0 ("D0"), day 14 ("D14"), and at day 28 ("D28") post glaucoma induction. Data are expressed as mean±S.D.

The present disclosure shows that glaucoma can be treated by administering to a subject in need thereof an antagonist (e.g., isolated monoclonal antibody, or antigen binding portion thereof), which specifically binds to human family with sequence similarity 19, member A5 (FAM19A5)

protein. Not being bound by any one theory, one possible mechanism of treatment is by reducing, ameliorating, or inhibiting inflammation associated with a glaucoma.

To facilitate an understanding of the disclosure disclosed herein, a number of terms and phrases are defined. Additional definitions are set forth throughout the detailed description.

I. Definitions

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "glaucoma" refers to a group of ocular-related diseases and/or disorders characterized by the progressive loss of retinal ganglion cell death and optic nerve atrophy. The glaucoma may be associated with an optic nerve damage, a retinal ganglion cell ("RGC") loss, a high intraocular pressure ("TOP"), an impaired blood-retina barrier, and/or an increase in a level of microglia activity within a retina and/or optic nerve of the subject. The glaucoma may be asymptomatic or may have any of the following symptoms associated with the eyes: burning or stinging sensation, tearing, dryness, tiredness, blurry/dim vision, tunnel vision, difficulty seeing in daylight, difficulty seeing in dark places, halos around lights and/or blindness. Lee et al., *Arch Ophthalmol* 116: 861-866 (1998). The term "glaucoma" includes any and all types of glaucoma regardless of the cause and any and all symptoms of glaucoma.

The term glaucoma includes but is not limited to the following types of glaucoma:

open-angle glaucoma, angle-closure glaucoma, normal-tension glaucoma ("NTG"), congenital glaucoma, secondary glaucoma, pigmentary glaucoma, pseudoexfoliative glaucoma, traumatic glaucoma, neovascular glaucoma, irido corneal endothelial syndrome, and/or and uveitic glaucoma. Some of the risk factors include: elevated intraocular pressure, genetic predisposition (e.g., family history of glaucoma, certain ethnicity), age, diabetes, high blood pressure, and/or physical injury to the eye.

The term "inflammation" refers to a complex reaction of the innate immune system in vascularized tissues that involves the accumulation and activation of immune cells (e.g., microglia) and plasma proteins at a site of an injury and/or damage. In healthy individuals, the blood-retina barrier provides a tight barrier that prevents the free flow of material from the blood to the retina and vice versa. However, in glaucoma patients, this barrier is damaged. This vascular dysregulation restricts the blood flow to the optic nerve head of the retinal and allows the production of various inflammatory mediators (e.g., TNF-$\alpha$, IL-6, IL-9, IL-10, and nitric oxide), which can freely move to the optic nerve head.

The term "optic nerve damage" refers to an alteration of the normal structure or function of the optic nerve. The alteration of the normal structure or function of the optic nerve can be the result of any disease, disorder, or injury, including glaucoma. An alteration of the normal function of the optic nerve includes any alteration of the ability of the optic nerve to function appropriately, such as transmit visual information from the retina to the brain. An alteration in function can manifest itself, for example, as loss of visual field, impaired central visual acuity, abnormal color vision, and so forth. Examples of alteration of structure include nerve fiber loss in the retina, abnormal cupping of the optic nerve, and/or loss of cells from the retinal ganglion cell layer of the retina. "Optic nerve damage" as used herein can include optic nerve damage to one or both optic nerves of a subject.

The term "retinal ganglion cells" (RGCs) refers to a specific type of neuron located near the innermost layer of the retina (i.e., the ganglion cell layer). These cells play a crucial role in conveying visual information gathered from the photoreceptors to the brain. Sanes et al., *Annu Rev Neurosci* 38:221-46 (2015). RGCs can vary significantly in terms of their size, connections, and responses to visual stimulation, but they all share the defining property of having a long axon that extends into the brain.

The term "intraocular pressure" (IOP) refers to the pressure that is maintained within the eye. The anterior chamber of the eye is bounded by the cornea, iris, pupil and lens. It is filled with aqueous humor, a watery fluid responsible for providing the cornea and lens with oxygen and nutrients. The aqueous humor provides the necessary pressure to help maintain the shape of the eye. When normal secretion of the aqueous humor is interrupted, intraocular pressure is affected.

The term "microglia" or "microglial cells" refers to a type of glial cells that are present within the retina. These cells behave like macrophages and are constantly surveying the surrounding microenvironment for foreign antigen and/or injury. Upon such recognition, the microglia become activated and quickly respond to the foreign antigen and/or injury by phagocytosing any potentially harmful debris to limit the damage, secreting inflammatory mediators, and interacting with other immune cells to generate an effective immune response. Kettenmann et al., *Physiol Rev* 91(2): 461-553 (2011). Activated microglia are distinguishable from those that are in a resting state by the increased surface expression of Iba-1. Microglial cells are also involved in programmed cell death in the developing retina, and nerve growth factor (NGF) released by microglia may induce retinal neuronal cell death. Ashwell et al., *Visual Neuroscience* 2(5): 437-448 (1989).

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, "administering" refers to the physical introduction of a therapeutic agent or a composition comprising a therapeutic agent to a subject, using any of the various methods and delivery systems known to those skilled in the art. The different routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravitreal, intravenous, intraperitoneal, intramuscular, intraarterial, intrathecal, intralymphatic, intralesional, intracapsular, intraorbital, intracardiac, intradermal, transtracheal, pulmonary, subcutaneous, subcuticular, intraarticular, subcapsular, subarachnoid, intraventricle, intravitreal, epidural, and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The term "therapeutically effective amount" as used herein refers to an amount of a drug, alone or in combination with another therapeutic agent, effective to "treat" a disease or disorder in a subject or reduce the risk, potential, possibility or occurrence of a disease or disorder (e.g., a glaucoma). A "therapeutically effective amount" includes an amount of a drug or a therapeutic agent that provides some improvement or benefit to a subject having or at risk of having a disease or disorder (e.g., a glaucoma disclosed herein). Thus, a "therapeutically effective" amount is an amount that reduces the risk, potential, possibility or occurrence of a disease or provides disorder or some alleviation, mitigation, and/or reduces at least one indicator (e.g., increased inflammation), and/or decrease in at least one clinical symptom of a disease or disorder.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

The term "family with sequence similarity 19, member A5" or "FAM19A5" refers to a protein that belongs to the TAFA family (also known as FAM19 family) of five highly homologous proteins and is predominantly expressed in brain and the spinal cord. Tang T. Y. et al., *Genomics* 83(4):727-34 (2004). These proteins contain conserved cysteine residues at fixed positions, and are distantly related to macrophage inflammatory protein 1-alpha (MIP-1-alpha), a member of the CC-chemokine family. The TAFA proteins are predominantly expressed in specific regions of the brain and the spinal cord. These proteins are believed to be generated and secreted by adult neural stem cells in neurogenesis processes. FAM19A5 is also known as TAFA5 or Chemokine-like protein TAFA-5.

FAM19A5 is predominantly expressed in the brain of vertebrates and it is believed that FAM19A5 is important for the development, differentiation, formation of a complete central nervous system. FAM19A5 also plays a significant role in the pathogenesis of many central nervous system damage and/or degenerative brain diseases (e.g., Huntington's disease, Parkinson's disease, Alzheimer's disease, cerebrospinal damage, strokes, and brain tumors). Upon damage to the central nervous system, neural stem cells produce FAM19A5, which induces the differentiation of normal astrocytes into reactive astrocytes. These reactive astrocytes (along with microglia) can express a wide array of ECMs (e.g., proteoglycans) and induce the formation of glial scars, which can surround the damaged region of the central nervous system like a net and prevent the regeneration of the neurons. Antibodies against FAM19A5 can be used in the prevention and/or treatment of central nervous system injuries and/or diseases. See U.S. Pat. No. 9,579,398.

In humans, the gene encoding FAM19A5 is located on chromosome 22. There are three human FAM19A5 (UniProt: Q7Z5A7) isoforms, which are believed to be produced by alternative splicing: isoform 1 (UniProt: Q7Z5A7-1), which consists of 132 amino acids; isoform 2 (UniProt: Q7Z5A7-2), which consists of 125 amino acids; and isoform 3 (UniProt: Q7Z5A7-3), which consists of 53 amino acids. Human FAM19A5 protein is believed to exist as both membrane bound and soluble (secreted) forms. Isoform 1 is believed to be a membrane protein with one transmembrane region. Isoform 2, which was reported in Tang T. Y. et al., *Genomics* 83(4):727-34 (2004) as a secreted protein (soluble), contains a signal peptide at amino acid positions 1-25. Isoform 3 is predicted based on EST data. Below are the amino acid sequences of the three known human FAM19A5 isoforms.

(I) Isoform 1 (UniProt: Q7Z5A7-1, transmembrane protein): this isoform has been chosen as the canonical sequence.

```
                                            (SEQ ID NO: 1)
MAPSPRTGSR QDATALPSMS STFWAFMILA SLLIAYCSQL

AAGTCEIVTL DRDSSQPRRT IARQTARCAC RKGQIAGTTR

ARPACVDARI IKTKQWCDML PCLEGEGCDL LINRSGWTCT

QPGGRIKTTT VS
```

(II) Isoform 2 (UniProt: Q7Z5A7-2, soluble protein):

(SEQ ID NO: 2)
MQLLKALWAL AGAALCCFLV LVIHAQFLKE GQLAAGTCEI

VTLDRDSSQP RRTIARQTAR CACRKGQIAG TTRARPACVD

ARIIKTKQWC DMLPCLEGEG CDLLINRSGW TCTQPGGRIK

TTTVS (III) Isoform 3 (UniProt: Q7Z5A7-3):

(SEQ ID NO: 3)
MYHHREWPAR IIKTKQWCDM LPCLEGEGCD LLINRSGWTC

TQPGGRIKTT TVS

The term "FAM19A5" includes any variants or isoforms of FAM19A5 which are naturally expressed by cells. Accordingly, antibodies described herein can cross-react with different isoforms in the same species (e.g., different isoforms of human FAM19A5), or cross-react with FAM19A5 from species other than human (e.g., mouse FAM19A5). Alternatively, the antibodies can be specific for human FAM19A5 and cannot exhibit any cross-reactivity with other species. FAM19A5, or any variants and isoforms thereof, can either be isolated from cells or tissues which naturally express them or be recombinantly produced. The polynucleotide encoding human FAM19A5 has the GenBank Accession No. BC039396 and the following sequence:

TABLE 1A

Polynucleotide sequence of human FAM19A5

Polynucleotide sequence (SEQ ID NO: 4)

| | |
|---|---|
| FAM19A5 | ggcggcggag gatggcgcgc gcggggcccg |
| (GenBank | cacgtggagg ccggcgcggg ggcgcgggca |
| Accession No. | gggccggctg ctgagacgcg ctgctgcccc |
| BC039396) | ccgcgcgggc gccgcggctt caatgcgccc |
| | atcgcccagg accggcagcc ggcaagatgc |
| | gaccgccctg cccagcatgt cctcaacttt |
| | ctgggcgttc atgatcctgg ccagcctgct |
| | catcgcctac tgcagtcagc tggccgccgg |
| | cacctgtgag attgtgacct tggaccggga |
| | cagcagccag cctcggagga cgatcgcccg |
| | gcagaccgcc cgctgtgcgt gtagaaaggg |
| | gcagatcgcc ggcaccacga gagcccggcc |
| | cgcctgtgtg gacgcaagaa tcatcaagac |
| | caagcagtgg tgtgacatgc ttccgtgtct |
| | ggaggggaa ggctgcgact tgttaatcaa |
| | ccggtcaggc tggacgtgca cgcagcccgg |
| | cgggaggata aagaccacca cggtctcctg |
| | acaaacacag cccctgaggg ggccccggga |
| | gtggccttgg ctccctggag agcccacgtc |
| | tcagccacag ttctccactc gcctcggact |
| | tcacccgttc tctgccgccc gcccactccg |
| | tttccctgtg gtccgtgaag gacggcctca |
| | ggccttggca tcctgagctt cggtctgtcc |
| | agccgacccg aggaggccgg actcagacac |
| | ataggcgggg ggcggcacct ggcatcagca |
| | atacgcagtc tgtgggagcc cggccgcgcc |
| | cagcccccgc cgaccgtggc gttggccctg |
| | ctgtcctcag aggaggagga ggaggaggca |
| | gctccggcag ccacagaagg ctgcagccca |
| | gcccgcctga gacacgacgc ctgcccagg |
| | ggactgtcag gcacagaagc ggcctcctcc |
| | cgtgccccag actgtccgaa ttgctttat |
| | tttcttatac tttcagtata ctccatagac |
| | caaagagcaa aatctatctg aacctggacg |
| | caccctcact gtcagggtcc ctggggtcgc |
| | ttgtgcgggc gggagggcaa tggtggcaga |
| | gacatgctgg tggccccggc ggagcggaga |

TABLE 1A-continued

Polynucleotide sequence of human FAM19A5

Polynucleotide sequence (SEQ ID NO: 4)

| |
|---|
| gggcggccgt ggtggaggcc tccaccccag |
| gagcaccccg cacaccctcg gaggacgggc |
| ttcggctgcg cggaggccgt ggcacacctg |
| cgggaggcag cgacggcccc cacgcagacg |
| ccgggaacgc aggccgcttt attcctctgt |
| acttagatca acttgaccgt actaaaatcc |
| ctttctgttt taaccagtta aacatgcctc |
| ttctacagct ccatttttga tagttggata |
| atccagtatc tgccaagagc atgttgggtc |
| tcccgtgact gctgcctcat cgataccca |
| tttagctcca gaaagcaaag aaaactcgag |
| taacacttgt ttgaaagaga tcattaaatg |
| tattttgcaa agcccaaaaa aaaaaaaaaa |
| a |

The term "antagonist against a FAM19A5 protein" refers to all antagonists that suppress the expression of the FAM19A5 protein. Such antagonist can be a peptide, nucleic acid, or a compound. More specifically, the antagonist can be an antisense-oligonucleotide, siRNA, shRNA, miRNA, dsRNA, aptamer, PNA (peptide nucleic acid) targeting FAM19A5, or a vector including the same. In some embodiments, the antagonist can be an antibody, or an antigen-binding portion thereof, that specifically binds to the FAM19A5 protein.

The terms "antibody" and "antibodies" are terms of art and can be used interchangeably herein and refer to a molecule with an antigen binding site that specifically binds an antigen. The terms as used to herein include whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen-binding portion thereof. In another embodiment, an "antibody" refers to a single chain antibody comprising a single variable domain, e.g., VHH domain. Each heavy chain is comprised of a heavy chain variable region (abbreviated herein as VH) and a heavy chain constant region. In certain naturally-occurring antibodies, the heavy chain constant region is comprised of three domains, CH1, CH2 and CH3. In certain naturally-occurring antibodies, each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "Kabat numbering" and like terms are recognized in the art and refer to a system of numbering amino acid residues in the heavy and light chain variable regions of an antibody, or an antigen-binding portion thereof In certain aspects, the CDRs of an antibody can be determined according to the Kabat numbering system (see, e.g., Kabat E A &

Wu T T (1971) *Ann NY Acad Sci* 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82. See TABLE 1B.

TABLE 1B

| Loop | Kabat | AbM | Clothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See, e.g., Lefranc, M. P. et al., *Dev. Comp. Immunol.* 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

For all heavy chain constant region amino acid positions discussed in the present disclosure, numbering is according to the EU index first described in Edelman et al., 1969, *Proc. Natl. Acad. Sci. USA* 63(1):78-85, describing the amino acid sequence of myeloma protein EU, which is the first human IgG1 sequenced. The EU index of Edelman et al. is also set forth in Kabat et al., 1991, Sequences of Proteins of Immunological Interest, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 EU antibody of Edelman et al. as set forth in Kabat 1991.

The numbering system used for the variable domains (both heavy chain and light chain) and light chain constant region amino acid sequence is that set forth in Kabat 1991.

Antibodies can be of any type (e.g., IgG, IgE, IgM, IgD, IgA, or IgY), any class (e.g., IgD, IgG2, IgG3, IgG4, IgA1, or IgA2), or any subclass (e.g., IgG1, IgG2, IgG3, and IgG4 in humans; and IgG1, IgG2a, IgG2b, and IgG3 in mice) of immunoglobulin molecule. Immunoglobulins, e.g., IgG1, exist in several allotypes, which differ from each other in at most a few amino acids. An antibody disclosed herein can be from any of the commonly known isotypes, classes, subclasses, or allotypes. In certain embodiments, the antibodies described herein are of the IgG1, IgG2, IgG3, or IgG4 subclass or any hybrid thereof. In certain embodiments, the antibodies are of the human IgG1 subclass or the human IgG2 or human IgG4 subclass.

"Antibody" includes, by way of example, both naturally-occurring and non-naturally-occurring antibodies; monoclonal and polyclonal antibodies; chimeric and humanized antibodies; human and non-human antibodies; wholly synthetic antibodies; single chain antibodies; monospecific antibodies; multispecific antibodies (including bispecific antibodies); tetrameric antibodies comprising two heavy chain and two light chain molecules; an antibody light chain monomer; an antibody heavy chain monomer; an antibody light chain dimer, an antibody heavy chain dimer; an antibody light chain-antibody heavy chain pair; intrabodies; heteroconjugate antibodies; monovalent antibodies; camelized antibodies; affybodies; anti-idiotypic (anti-Id) antibodies (including, e.g., anti- anti-Id antibodies), and single-domain antibodies (sdAbs), which include binding molecules consisting of a single monomeric variable antibody domain that are fully capable of antigen binding (e.g., a VH domain or a VL domain). Harmen M. M. and Haard H. J. *Appl Microbiol Biotechnol.* 77(1): 13-22 (2007)).

The term "antigen-binding portion" of an antibody, as used herein, refers to one or more fragments of an antibody that retain the ability to specifically bind to an antigen (e.g., human FAM19A5). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, e.g., an anti-FAM19A5 antibody described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv); (v) a dAb fragment (Ward et al., (1989) *Nature* 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see, e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR).

Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

As used herein, the term "heavy chain" when used in reference to an antibody can refer to any distinct type, e.g., alpha ($\alpha$), delta ($\delta$), epsilon ($\epsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

The terms "VL" and "VL domain" are used interchangeably to refer to the light chain variable region of an antibody.

The terms "VH" and "VH domain" are used interchangeably to refer to the heavy chain variable region of an antibody.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains C$\gamma$2 and C$\gamma$3 and the hinge between C$\gamma$1 and C$\gamma$2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a Cm domain in an Fc region, i.e., it extends from about amino acid 341 to about amino acid 447 of an IgG. As used herein, the Fc region can be a native sequence Fc, including any allotypic variant, or a variant Fc (e.g., a non-naturally-occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesion).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc includes the various allotypes of Fes (see, e.g., Jefferis et al. (2009) mAbs 1:1; Vidarsson G. et al. *Front Immunol.* 5:520 (published online Oct. 20, 2014)).

An "Fc receptor" or "FcR" is a receptor that binds to the Fc region of an immunoglobulin. FcRs that bind to an IgG antibody comprise receptors of the Fc$\gamma$R family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Human IgG1 binds to most human Fc receptors and elicits the strongest Fc effector functions. It is considered equivalent to murine IgG2a with respect to the types of activating Fc receptors that it binds to. Conversely, human IgG4 elicits the least Fc effector functions. Vidarsson G. et al. *Front Immunol.* 5:520 (published online Oct. 20, 2014).

The constant region can be manipulated, e.g., by recombinant technology, to eliminate one or more effector functions. An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

Effector functions of an antibody can be reduced or avoided by different approaches. Effector functions of an antibody can be reduced or avoided by using antibody fragments lacking the Fc region (e.g., such as a Fab, F(ab')$_2$, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). See, e.g., U.S. Pub. No. 20120100140. Another approach is to employ Fc regions from an IgG subclass that have reduced effector function, for example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. Vidarsson G. et al. *Front Immunol.* 5:520 (published online Oct. 20, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al. *J. Immunol.* 191:4769-4777 (2013)), or an Fc region with mutations that result in altered Fc effector functions, e.g., reduced or no Fc functions. Such Fc regions with mutations are known in the art. See, e.g., U.S. Pub. No. 20120100140 and U.S. and PCT applications cited therein and An et al. *mAbs* 1:6, 572-579 (2009); the disclosure of which are incorporated by reference to their entirety.

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. *J. Immunol.* 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 *J Immunol* 161:4083). The sequences of wild-type IgG1, IgG2, IgG3 and IgG4 hinges are known in the art. See, e.g., Kabat E A et al., (1991) Sequences of Proteins of Immunological Interest, Fifth Edition, U.S. Department of Health and Human Services, NIH Publication No. 91-3242; Vidarsson G. et al. *Front Immunol.* 5:520 (published online Oct. 20, 2014).

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art. See, e.g., Kabat E A et al, (1991) supra and Vidarsson G. et al. *Front Immunol.* 5:520 (published online Oct. 20, 2014). Exemplary CH1 domains include CH1 domains with mutations that modify a biological activity of an antibody, e.g., half-life, e.g., described in U.S. Pub. No. 20120100140 and U.S. patents and publications and PCT publications cited therein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH2 domains include CH2 domains with mutations that modify a biological activity of an antibody, e.g., half-life and/or reduced Fc effector function, e.g., described in U.S. Pub. No. 20120100140 and U.S. patents and publications and PCT publications cited therein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH3 domains include CH3 domains with mutations that modify a biological activity of an antibody, e.g., half-life, e.g., described in U.S. Pub. No. 20120100140 and U.S. patents and publications and PCT publications cited therein.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally-occurring variants within a specific isotype group, which variants differ in a few amino acids (see, e.g., Jefferis et al. (2009) mAbs 1:1). Antibodies described herein can be of any allotype. Allotypes of IgG1, IgG2, IgG3, and IgG4 are known in the art. See, e.g., Kabat E A et al., (1991) supra; Vidarsson G. et al. *Front Immunol.* 5:520 (published online Oct. 20, 2014); and Lefranc M P, mAbs 1:4, 1-7(2009).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to FAM19A5 is substantially free of antibodies that specifically bind antigens other than FAM19A5). An isolated antibody that specifically binds to an epitope of FAM19A5 can, however, have cross-reactivity to other FAM19A5 proteins from different species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$ and is expressed as a molar concentration (M), whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as immunoassays (e.g., enzyme-linked immunosorbent assay (ELISA)), BIACORE™ or kinetic exclusion assay (KINEXA®).

As used herein, the terms "specifically binds," "specifically recognizes," "specific binding," "selective binding," and "selectively binds," are analogous terms in the context of antibodies and refer to molecules (e.g., antibodies) that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIACORE™, KINEXA® 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $10^{-9}$ M or less, and most preferably between $10^{-8}$ M and $10^{-10}$ M or less, when determined by, e.g., immunoassays (e.g., ELISA) or surface plasmon resonance (SPR) technology in a BIACORE™ 2000 instrument using the predetermined antigen, but does not bind with high affinity to unrelated antigens.

As used herein, the term "antigen" refers to any natural or synthetic immunogenic substance, such as a protein, peptide, or hapten. An antigen can be FAM19A5 or a fragment thereof.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). Epitopes formed from contiguous amino acids are typically, but not always, retained on exposure to denaturing solvents, whereas epitopes formed by tertiary folding are typically lost on treatment with denaturing solvents. An epitope typically includes at least 1, 2, 3, 4, 5, 6, 7, 8, 9, 10, 11, 12, 13, 14, 15, or 20 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from FMAM19A5) are tested for reactivity with a given antibody (e.g., anti-FAM19A5 antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies can be accomplished using any method known to one of skill in the art. See, e.g., Champe M et al., (1995) *J Biol Chem* 270: 1388-1394 and Cunningham B C & Wells J A (1989) *Science* 244: 1081-1085 for a description of mutagenesis techniques, including alanine scanning mutagenesis techniques.

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on FAM19A5" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)).

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The term "cross-reacts," as used herein, refers to the ability of an antibody described herein to bind to FAM19A5 from a different species. For example, an antibody described herein that binds human FAM19A5 can also bind another species of FAM19A5 (e.g., mouse FAM19A5). As used herein, cross-reactivity can be measured by detecting a specific reactivity with purified antigen in binding assays (e.g., SPR, ELISA) or binding to, or otherwise functionally interacting with, cells physiologically expressing FAM19A5. Methods for determining cross-reactivity include standard binding assays as described herein, for example, by BIACORE™ surface plasmon resonance (SPR) analysis using a BIACORE™ 2000 SPR instrument (Biacore AB, Uppsala, Sweden), or flow cytometric techniques.

The term "naturally-occurring" as applied to an object herein refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

The term "therapeutically effective amount" as used herein refers to an amount of a drug, alone or in combination with another therapeutic agent, effective to "treat" a disease or disorder in a subject or reduce the risk, potential, possibility or occurrence of a disease or disorder (e.g., a glaucoma). A "therapeutically effective amount" includes an amount of a drug or a therapeutic agent that provides some improvement or benefit to a subject having or at risk of having a disease or disorder (e.g., a glaucoma). Thus, a "therapeutically effective" amount is an amount that reduces the risk, potential, possibility or occurrence of a disease or provides disorder or some alleviation, mitigation, and/or reduces at least one indicator (e.g., increased inflammation associated with a glaucoma), and/or decrease in at least one clinical symptom of a disease or disorder (e.g., a glaucoma).

II. Methods of Treating Glaucoma

Disclosed herein are methods of treating a glaucoma in a subject in need thereof, comprising administering to the subject an antagonist against FAM19A5. In one embodiment, the antagonist is an antibody, or an antigen-binding portion thereof, that specifically binds to the FAM19A5 protein ("an anti-FAM19A5 antibody or antigen-binding portion thereof"), a polynucleotide encoding the anti-FAM19A5 antibody or an antigen binding portion thereof, or a vector comprising the polynucleotide thereof. In one embodiment, the anti-FAM19A5 antibody or antigen-binding portion thereof binds to FAM19A5 protein and reduces FAM19A5 activity. In one embodiment, the reduced FAM19A5 activity reduces, ameliorates, or inhibits inflammation associated with a glaucoma.

In connection with the current disclosure, it has been shown that anti-FAM19A5 antibody can reduce and/or prevent the loss of retinal ganglion cells observed in glaucoma patients. See Example 8. Contrary to many of the current treatment options available for glaucoma, in one embodiment, the anti-FAM19A5 antibody may have no effect on reducing elevated intraocular pressure. See Example 6. Instead, the anti-FAM19A5 antibody appears to suppress inflammation around the optic nerve head of the retina by regulating the activation of microglial cells. See Example 9. Accordingly, the method disclosed herein can treat a glaucoma by reducing, alleviating, or preventing the loss of retinal ganglion cells within the optic nerve head. In a specific embodiment, the anti-FAM19A5 antibody treats glaucoma by regulating the activity of microglial cells within the retina and thereby, reducing the level of inflammatory mediators produced in the subject in need thereof.

In one embodiment, the glaucoma is selected from the group consisting of an open-angle glaucoma, angle-closure glaucoma, normal-tension glaucoma ("NTG"), congenital glaucoma, secondary glaucoma, pigmentary glaucoma, pseudoexfoliative glaucoma, traumatic glaucoma, neovascular glaucoma, irido corneal endothelial syndrome, and uveitic glaucoma. In one embodiment, the glaucoma is associated with an optic nerve damage, a retinal ganglion cell ("RGC") loss, a high intraocular pressure ("IOP"), an impaired blood-retina barrier, and/or an increase in a level of microglia activity within a retina and/or optic nerve of the subject.

In one embodiment, the subject being treated in the method is a nonhuman animal such as a rat or a mouse. In one embodiment, the subject being treated in the method is a human.

In some embodiments, an anti-FAM19A5 antibody or antigen-binding portion thereof, a bispecific molecule or an immunoconjugate, or a composition thereof disclosed herein is administered intravenously, orally, parenterally, intrathecally, intra-cerebroventricularly, pulmonarily, intramuscularly, subcutaneously, intravitreally, or intraventricularly.

For administration of an anti-FAM19A5 antibody or antigen-binding portion thereof, e.g., described herein, the dosage ranges from about 0.0001 to 100 mg/kg.

In some embodiments, an anti-FAM19A5 antibody or antigen-binding portion thereof, or a composition thereof can be administered in combination with one or more additional agent for treating a glaucoma (e.g., (i) prostaglandin analogs, such as XALATAN®, LUMIGAN®, TRAVATAN Z®; (ii) alpha agonists, such as ALPHAGAN® P and IOPIDINE®; and (iii) carbonic anhydrase inhibitors, such as TRUSOPT® and AZOPT®). Dose and administration of the one or more additional therapeutic drugs are known in the art, e.g., as instructed by the product label of the respective drug.

III. FAM19A5 Antagonists

In one embodiment, the FAM19A5 antagonist is an antisense oligonucleotide, siRNA, shRNA, miRNA, dsRNA, aptamer, PNA (peptide nucleic acid) that specifically targets FAM19A5, or a vector including the same. In another embodiment, the FAM19A5 antagonist is an antibody, or an antigen-binding portion thereof, that specifically binds to the FAM19A5 protein, a polynucleotide encoding the anti-FAM19A5 antibody or antigen-binding portion thereof, or a vector comprising the polynucleotide thereof.

Antibodies that are useful in the methods disclosed herein include monoclonal antibodies, which are characterized by particular functional features or properties. For example, the antibodies specifically bind human FAM19A5, including soluble FAM19A5 and membrane bound FAM19A5. In addition to binding specifically to soluble and/or membrane bound human FAM19A5, the antibodies described herein also (a) binds to soluble human FAM19A5 with a $K_D$ of 10 nM or less; (b) binds to membrane bound human FAM19A5 with a $K_D$ of 1 nM or less; or both (a) and (b).

In some embodiments, the anti-FAM19A5 antibody or antigen binding portion thereof specifically binds to soluble human FAM19A5 or membrane-bound human with high affinity, for example, with a $K_D$ of $10^{-7}$ M or less, $10^{-8}$ M or less, $10^{-9}$ M (1 nM) or less, $10^{-10}$ M (0.1 nM) or less, $10^{-11}$ M or less, or $10^{-12}$ M or less, e.g., $10^{-12}$ M to $10^{-7}$ M, $10^{-11}$ M to $10^{-7}$ M, $10^{-10}$ M to $10^{-7}$ M, or $10^{-9}$ M to $10^{-7}$ M, e.g., $10^{-12}$ M, $5\times10^{-12}$ M, $10^{-11}$ M, $5\times10^{-11}$ M, $10^{-10}$ M, $5\times10^{-10}$ M, $10^{-9}$ M, $5\times10^{-9}$ M, $10^{-8}$ M, $5\times10^{-8}$ M, $10^{-7}$ M, or $5\times10^{-7}$ M. Standard assays to evaluate the binding ability of the antibody toward human FAM19A5 of various species are known in the art, including for example, ELISAs, Western blots, and RIAs. Suitable assays are described in detail in the Examples. The binding kinetics (e.g., binding affinity) of the antibodies also can be assessed by standard assays known in the art, such as by ELISA, BIACORE™ analysis or KITNEXA®. Assays to evaluate the effects of the antibodies on functional properties of FAM19A5 (e.g., ligand binding) are described in further detail infra and in the Examples.

In some embodiments, the anti-FAM19A5 antibody or antigen binding portion thereof binds to soluble human FAM19A5 with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In some embodiments, the anti-FAM19A5 antibody or antigen binding portion thereof binds to soluble FAM19A5 with a $K_D$ of 10 nM or less, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody or antigen binding portion thereof specifically binds to soluble human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

In some embodiments, the anti-FAM19A5 antibody or antigen binding portion thereof binds to membrane-bound human with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In certain embodiments, the anti-FAM19A5 antibody or antigen binding portion thereof specifically binds to membrane-bound human FAM19A5 with a $K_D$ of 10 nM or less as determined by ELISA, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody or antigen binding portion thereof binds to membrane-bound human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

In certain embodiments, the anti-FAM19A5 antibody or antigen binding portion thereof of useful in the methods disclosed herewith thereof cross-competes for binding to (or inhibits binding of) a human FAM19A5 epitope with an anti-FAM19A5 antibody comprising CDRs or variable regions disclosed herein.

In certain embodiments, anti-FAM19A5 antibodies or antigen binding portions thereof inhibit binding of a reference antibody comprising heavy chain CDR1, CDR2, and CDR3, and light chain CDR1, CDR2, and CDR3, (i) wherein the heavy chain CDR1, CDR2, and CDR3 of the reference antibody comprise the amino acid sequence of SEQ ID NO: 11, SEQ ID NO: 12, and SEQ ID NO: 13, respectively, and light chain CDR1, CDR2, and CDR3 of the reference antibody comprise the amino acid sequence of SEQ ID NO: 23, SEQ ID NO: 24, and SEQ ID NO: 25; (ii) wherein the heavy chain CDR1 comprises the amino acid sequence of SEQ ID NO: 14, the heavy chain CDR2 comprises the amino acid sequence of SEQ ID NO: 15, and the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28; (iii) wherein the heavy chain CDR1 comprises the amino acid sequence of SEQ ID NO: 17, the heavy chain CDR2 comprises the amino acid sequence of SEQ ID NO: 18, and the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34; (v) wherein the heavy chain CDR1 comprises the amino acid sequence of SEQ ID NO: 89, the heavy chain CDR2 comprises the amino acid sequence of SEQ ID NO: 90, the heavy chain CDR3 comprises the amino acid sequence of SEQ ID NO: 91, the light chain CDR1 comprises the amino acid sequence of SEQ ID NO: 92, the light chain CDR2 comprises the amino acid sequence of SEQ ID NO: 93, and the light chain CDR3 comprises the amino acid sequence of SEQ ID NO: 94; (vi) wherein the heavy chain CDR1 comprises the amino acid sequence of SEQ ID NO: 95, the heavy chain CDR2 comprises the amino acid sequence of SEQ ID NO: 96, the heavy chain CDR3 comprises the amino acid sequence of SEQ ID NO: 97, the light chain CDR1 comprises the amino acid sequence of SEQ ID NO: 98, the light chain CDR2 comprises the amino acid sequence of SEQ ID NO: 99, and the light chain CDR3 comprises the amino acid sequence of SEQ ID NO: 100; (vii) wherein the heavy chain CDR1 comprises the amino acid sequence of SEQ ID NO: 101, the heavy chain CDR2 comprises the amino acid sequence of SEQ ID NO: 102, the heavy chain CDR3 comprises the amino acid sequence of SEQ ID NO: 103, the light chain CDR1 comprises the amino acid sequence of SEQ ID NO: 104, the light chain CDR2 comprises the amino acid sequence of SEQ ID NO: 105, and the light chain CDR3 comprises the amino acid sequence of SEQ ID NO: 106; (viii) wherein the heavy chain CDR1 comprises the amino acid sequence of SEQ ID NO: 107, the heavy chain CDR2 comprises the amino acid sequence of SEQ ID NO: 108, the heavy chain CDR3 comprises the amino acid sequence of SEQ ID NO: 109, the light chain CDR1 comprises the amino acid sequence of SEQ ID NO: 110, the light chain CDR2 comprises the amino acid sequence of SEQ ID NO: 111, and the light chain CDR3 comprises the amino acid sequence of SEQ ID NO: 112; (ix) wherein the heavy chain CDR1 comprises the amino acid sequence of SEQ ID NO: 113, the heavy chain CDR2 comprises the amino acid sequence of SEQ ID NO: 114, the heavy chain CDR3 comprises the amino acid sequence of SEQ ID NO: 115, the light chain CDR1 comprises the amino acid sequence of SEQ ID NO: 116, the light chain CDR2 comprises the amino acid sequence of SEQ ID NO: 117, and the light chain CDR3 comprises the amino acid sequence of SEQ ID NO: 118; (x) wherein the heavy chain CDR1 comprises the amino acid sequence of SEQ ID NO: 119, the heavy chain CDR2 comprises the amino acid sequence of SEQ ID NO: 120, the heavy chain CDR3 comprises the amino acid sequence of SEQ ID NO: 121, the light chain CDR1 comprises the amino acid sequence of SEQ ID NO: 122, the light chain CDR2 comprises the amino acid sequence of SEQ ID NO: 123, and the light chain CDR3 comprises the amino acid sequence of SEQ ID NO: 124; (xi) wherein the heavy chain CDR1 comprises the amino acid sequence of SEQ ID NO: 125, the heavy chain CDR2 comprises the amino acid sequence of SEQ ID NO: 126, the heavy chain CDR3 comprises the amino acid sequence of SEQ ID NO: 127, the light chain CDR1 comprises the amino acid sequence of SEQ ID NO: 128, the light chain CDR2 comprises the amino acid sequence of SEQ ID NO: 129, and the light chain CDR3 comprises the amino acid sequence of SEQ ID NO: 130; (xii) wherein the heavy chain CDR1 comprises the amino acid sequence of SEQ ID NO: 131, the heavy chain CDR2 comprises the amino acid sequence of SEQ ID NO: 132, the heavy chain CDR3 comprises the amino acid sequence of SEQ ID NO: 133, the light chain CDR1 comprises the amino acid sequence of SEQ ID NO: 134, the light chain CDR2 comprises the amino acid sequence of SEQ ID NO: 135, and the light chain CDR3 comprises the amino acid sequence of SEQ ID NO: 136; (xiii) wherein the heavy chain CDR1 comprises the amino acid sequence of SEQ ID NO: 137, the heavy chain CDR2 comprises the amino acid sequence of SEQ ID NO: 138, the heavy chain CDR3 comprises the amino acid sequence of SEQ ID NO: 139, the light chain CDR1 comprises the amino acid sequence of SEQ ID NO: 140, the light chain CDR2 comprises the amino acid sequence of SEQ ID NO: 141, and the light chain CDR3 comprises the amino acid sequence of SEQ ID NO: 142; (xiv) wherein the heavy chain CDR1 comprises the amino acid sequence of SEQ ID NO: 143, the heavy chain CDR2 comprises the amino acid sequence of SEQ ID NO: 144, the heavy chain CDR3 comprises the amino acid sequence of SEQ ID NO: 145, the light chain CDR1 comprises the amino acid sequence of SEQ ID NO: 146, the light chain CDR2 comprises the amino acid sequence of SEQ ID NO: 147, and the light chain CDR3 comprises the amino acid sequence of SEQ ID NO: 148; or (xv) wherein the heavy chain CDR1 comprises the amino acid sequence of SEQ ID NO: 149, the heavy chain CDR2 comprises the amino acid sequence of SEQ ID NO: 150, the heavy chain CDR3 comprises the amino acid sequence of SEQ ID NO: 151, the light chain CDR1 comprises the amino acid sequence of SEQ ID NO: 152, the light chain CDR2 comprises the amino acid sequence of SEQ ID NO: 153, and the light chain CDR3 comprises the amino acid sequence of SEQ ID NO: 154.

In some embodiments, the reference antibody comprises (a) heavy and light chain variable region sequences comprising SEQ ID NOs: 35 and 39, respectively; (b) heavy and light chain variable region sequences comprising SEQ ID NOs: 36 and 40, respectively; (c) heavy and light chain variable region sequences comprising SEQ ID NOs: 37 and 41, respectively; (d) heavy and light chain variable region sequences comprising SEQ ID NOs: 38 and 42, respectively; (e) heavy and light chain variable region sequences comprising SEQ ID NOs: 155 and 166, respectively; (f) heavy and light chain variable region sequences comprising SEQ ID NOs: 156 and 167, respectively; (g) heavy and light chain variable region sequences comprising SEQ ID NOs: 157 and 168, respectively; (h) heavy and light chain variable region sequences comprising SEQ ID NOs: 158 and 169, respectively; (i) heavy and light chain variable region sequences comprising SEQ ID NOs: 159 and 170, respectively; (j) heavy and light chain variable region sequences comprising SEQ ID NOs: 160 and 171, respectively; (k)

heavy and light chain variable region sequences comprising SEQ ID NOs: 161 and 172, respectively; (1) heavy and light chain variable region sequences comprising SEQ ID NOs: 162 and 173, respectively; (m) heavy and light chain variable region sequences comprising SEQ ID NOs: 163 and 174, respectively; (n) heavy and light chain variable region sequences comprising SEQ ID NOs: 164 and 175, respectively; or (o) heavy and light chain variable region sequences comprising SEQ ID NOs: 165 and 176, respectively.

In certain embodiments, the anti-FAM19A5 antibody or antigen binding portion thereof inhibits binding of such a reference antibody to human FAM19A5 by at least 10%, 20%, 30%, 40%, 50%, 60%, 70%, 80%, or 90% or by 100%. Competing antibodies bind to the same epitope, an overlapping epitope or to adjacent epitopes (e.g., as evidenced by steric hindrance). Whether two antibodies compete with each other for binding to a target can be determined using competition experiments known in the art such as RIA and EIA.

In certain embodiments, the anti-FAM19A5 antibody or antigen binding portions thereof bind to the same FAM19A5 epitope as a reference antibody disclosed herein comprising heavy chain CDR1, CDR2, and CDR3 and light chain CDR1, CDR2, and CDR3, (i) wherein the heavy chain CDR1 comprises the amino acid sequence of SEQ ID NO: 11, the heavy chain CDR2 comprises the amino acid sequence of SEQ ID NO: 12, the heavy chain CDR3 comprises the amino acid sequence of SEQ ID NO: 13, the light chain CDR1 comprises the amino acid sequence of SEQ ID NO: 23, the light chain CDR2 comprises the amino acid sequence of SEQ ID NO: 24, and the light chain CDR3 comprises the amino acid sequence of SEQ ID NO: 25; (ii) wherein the heavy chain CDR1 comprises the amino acid sequence of SEQ ID NO: 14, the heavy chain CDR2 comprises the amino acid sequence of SEQ ID NO: 15, the heavy chain CDR3 comprises the amino acid sequence of SEQ ID NO: 16, the light chain CDR1 comprises the amino acid sequence of SEQ ID NO: 26, the light chain CDR2 comprises the amino acid sequence of SEQ ID NO: 27, and the light chain CDR3 comprises the amino acid sequence of SEQ ID NO: 28; (iii) wherein the heavy chain CDR1 comprises the amino acid sequence of SEQ ID NO: 17, the heavy chain CDR2 comprises the amino acid sequence of SEQ ID NO: 18, the heavy chain CDR3 comprises the amino acid sequence of SEQ ID NO: 19, the light chain CDR1 comprises the amino acid sequence of SEQ ID NO: 29, the light chain CDR2 comprises the amino acid sequence of SEQ ID NO: 30, and the light chain CDR3 comprises the amino acid sequence of SEQ ID NO: 31; (iv) wherein the heavy chain CDR1 comprises the amino acid sequence of SEQ ID NO: 20, the heavy chain CDR2 comprises the amino acid sequence of SEQ ID NO: 21, the heavy chain CDR3 comprises the amino acid sequence of SEQ ID NO: 22, the light chain CDR1 comprises the amino acid sequence of SEQ ID NO: 32, the light chain CDR2 comprises the amino acid sequence of SEQ ID NO: 33, and the light chain CDR3 comprises the amino acid sequence of SEQ ID NO: 34; (v) wherein the heavy chain CDR1 comprises the amino acid sequence of SEQ ID NO: 89, the heavy chain CDR2 comprises the amino acid sequence of SEQ ID NO: 90, the heavy chain CDR3 comprises the amino acid sequence of SEQ ID NO: 91, the light chain CDR1 comprises the amino acid sequence of SEQ ID NO: 92, the light chain CDR2 comprises the amino acid sequence of SEQ ID NO: 93, and the light chain CDR3 comprises the amino acid sequence of SEQ ID NO: 94; (vi) wherein the heavy chain CDR1 comprises the amino acid sequence of SEQ ID NO: 95, the heavy chain CDR2 comprises the amino acid sequence of SEQ ID NO: 96, the heavy chain CDR3 comprises the amino acid sequence of SEQ ID NO: 97, the light chain CDR1 comprises the amino acid sequence of SEQ ID NO: 98, the light chain CDR2 comprises the amino acid sequence of SEQ ID NO: 99, and the light chain CDR3 comprises the amino acid sequence of SEQ ID NO: 100; (vii) wherein the heavy chain CDR1 comprises the amino acid sequence of SEQ ID NO: 101, the heavy chain CDR2 comprises the amino acid sequence of SEQ ID NO: 102, the heavy chain CDR3 comprises the amino acid sequence of SEQ ID NO: 103, the light chain CDR1 comprises the amino acid sequence of SEQ ID NO: 104, the light chain CDR2 comprises the amino acid sequence of SEQ ID NO: 105, and the light chain CDR3 comprises the amino acid sequence of SEQ ID NO: 106; (viii) wherein the heavy chain CDR1 comprises the amino acid sequence of SEQ ID NO: 107, the heavy chain CDR2 comprises the amino acid sequence of SEQ ID NO: 108, the heavy chain CDR3 comprises the amino acid sequence of SEQ ID NO: 109, the light chain CDR1 comprises the amino acid sequence of SEQ ID NO: 110, the light chain CDR2 comprises the amino acid sequence of SEQ ID NO: 111, and the light chain CDR3 comprises the amino acid sequence of SEQ ID NO: 112; (ix) wherein the heavy chain CDR1 comprises the amino acid sequence of SEQ ID NO: 113, the heavy chain CDR2 comprises the amino acid sequence of SEQ ID NO: 114, the heavy chain CDR3 comprises the amino acid sequence of SEQ ID NO: 115, the light chain CDR1 comprises the amino acid sequence of SEQ ID NO: 116, the light chain CDR2 comprises the amino acid sequence of SEQ ID NO: 117, and the light chain CDR3 comprises the amino acid sequence of SEQ ID NO: 118; (x) wherein the heavy chain CDR1 comprises the amino acid sequence of SEQ ID NO: 119, the heavy chain CDR2 comprises the amino acid sequence of SEQ ID NO: 120, the heavy chain CDR3 comprises the amino acid sequence of SEQ ID NO: 121, the light chain CDR1 comprises the amino acid sequence of SEQ ID NO: 122, the light chain CDR2 comprises the amino acid sequence of SEQ ID NO: 123, and the light chain CDR3 comprises the amino acid sequence of SEQ ID NO: 124; (xi) wherein the heavy chain CDR1 comprises the amino acid sequence of SEQ ID NO: 125, the heavy chain CDR2 comprises the amino acid sequence of SEQ ID NO: 126, the heavy chain CDR3 comprises the amino acid sequence of SEQ ID NO: 127, the light chain CDR1 comprises the amino acid sequence of SEQ ID NO: 128, the light chain CDR2 comprises the amino acid sequence of SEQ ID NO: 129, and the light chain CDR3 comprises the amino acid sequence of SEQ ID NO: 130; (xii) wherein the heavy chain CDR1 comprises the amino acid sequence of SEQ ID NO: 131, the heavy chain CDR2 comprises the amino acid sequence of SEQ ID NO: 132, the heavy chain CDR3 comprises the amino acid sequence of SEQ ID NO: 133, the light chain CDR1 comprises the amino acid sequence of SEQ ID NO: 134, the light chain CDR2 comprises the amino acid sequence of SEQ ID NO: 135, and the light chain CDR3 comprises the amino acid sequence of SEQ ID NO: 136; (xiii) wherein the heavy chain CDR1 comprises the amino acid sequence of SEQ ID NO: 137, the heavy chain CDR2 comprises the amino acid sequence of SEQ ID NO: 138, the heavy chain CDR3 comprises the amino acid sequence of SEQ ID NO: 139, the light chain CDR1 comprises the amino acid sequence of SEQ ID NO: 140, the light chain CDR2 comprises the amino acid sequence of SEQ ID NO: 141, and the light chain CDR3 comprises the amino acid sequence of SEQ ID NO: 142; (xiv) wherein the heavy chain CDR1 comprises the amino acid sequence of SEQ ID NO: 143, the heavy chain CDR2 comprises the amino acid sequence of SEQ ID NO: 144, the heavy chain CDR3 comprises the amino acid sequence of SEQ ID NO: 145, the light chain CDR1 comprises the amino acid sequence of SEQ ID NO: 146, the light chain CDR2 comprises the amino acid sequence of SEQ ID NO: 147, and the light chain CDR3 comprises the amino acid sequence of SEQ ID NO: 148; or (xv) wherein the heavy chain CDR1 comprises the amino acid sequence of SEQ ID NO: 149, the heavy chain CDR2 comprises the amino acid sequence of SEQ ID NO: 150, the heavy chain CDR3 comprises the amino acid sequence of SEQ ID NO: 151, the light chain CDR1 comprises the amino acid sequence of SEQ ID NO: 152, the light chain CDR2 comprises the amino acid sequence of SEQ ID NO: 153, and the light chain CDR3 comprises the amino acid sequence of SEQ ID NO: 154.

In some embodiments, the reference antibody comprises (a) heavy and light chain variable region sequences comprising SEQ ID NOs: 35 and 39, respectively; (b) heavy and light chain variable region sequences comprising SEQ ID NOs: 36 and 40, respectively; (c) heavy and light chain variable region sequences comprising SEQ ID NOs: 37 and 41, respectively; (d) heavy and light chain variable region sequences comprising SEQ ID NOs: 38 and 42, respectively; (e) heavy and light chain variable region sequences comprising SEQ ID NOs: 155 and 166, respectively; (f) heavy and light chain variable region sequences comprising SEQ ID NOs: 156 and 167, respectively; (g) heavy and light chain variable region sequences comprising SEQ ID NOs: 157 and 168, respectively; (h) heavy and light chain variable region sequences comprising SEQ ID NOs: 158 and 169, respectively; (i) heavy and light chain variable region sequences comprising SEQ ID NOs: 159 and 170, respectively; (j) heavy and light chain variable region sequences comprising SEQ ID NOs: 160 and 171, respectively; (k) heavy and light chain variable region sequences comprising SEQ ID NOs: 161 and 172, respectively; (l) heavy and light chain variable region sequences comprising SEQ ID NOs: 162 and 173, respectively; (m) heavy and light chain variable region sequences comprising SEQ ID NOs: 163 and 174, respectively; (n) heavy and light chain variable region sequences comprising SEQ ID NOs: 164 and 175, respectively; or (o) heavy and light chain variable region sequences comprising SEQ ID NOs: 165 and 176, respectively.

Techniques for determining whether two antibodies bind to the same epitope include, e.g., epitope mapping methods, such as, x-ray analyses of crystals of antigen:antibody complexes which provides atomic resolution of the epitope and hydrogen/deuterium exchange mass spectrometry (HDX-MS), methods monitoring the binding of the antibody to antigen fragments or mutated variations of the antigen, where loss of binding due to a modification of an amino acid residue within the antigen sequence is often considered an indication of an epitope component, computational combinatorial methods for epitope mapping.

An anti-FAM19A5 antibody or antigen binding portion thereof that would be useful in the methods disclosed herewith can bind to at least one epitope of mature human FAM19A5, as determined, e.g., by binding of the antibodies to fragments of human FAM19A5. In some embodiments, anti-FAM19A5 antibodies or antigen binding portions thereof bind to a fragment located within the amino acid sequence of TLDRDSSQPRRTIARQTARC (SEQ ID NO: 6 or amino acid residues 42 to 61 of SEQ ID NO: 2), e.g., an epitope having at least 3, 4, 5, 6, 7, 8, 9, 10, 11, 12, 13, 14, 15, 16, 17, 18, 19, or 20 amino acids of SEQ ID NO: 6. In some embodiments, anti-FAM19A5 antibodies or antigen binding portion thereof bind to SEQ ID NO: 6 at one or more amino acids corresponding to amino acid residues 46 to 51 (i.e., DSSQPR), e.g., amino acid residues 46, 50, and 52 (i.e., D-P-R), e.g., amino acid residues 46, 47, 48, and 50 (i.e., DSS-P) of SEQ ID NO: 2. In some embodiments, anti-FAM19A5 antibodies or antigen binding portions thereof bind to a fragment located within the amino acid sequence of CDMLPCLEGEGCDLLINRSG (SEQ ID NO: 9 or amino acids 90 to 109 of SEQ ID NO: 2), e.g., an epitope having at least 3, 4, 5, 6, 7, 8, 9, 10, 11, 12, 13, 14, 15, 16, 17, 18, 19, or 20 amino acids of SEQ ID NO: 9. In certain embodiments, anti-FAM19A5 antibodies or antigen binding portion thereof bind to SEQ ID NO: 9 at one or more amino acids residues 99 to 107 (i.e., EGCDLLINR), e.g., amino acid residues 102, 103, 105, and 107 (i.e., DL-I-R), e.g., amino acid residues 99, 100, 102, 103, 105, and 107 (i.e., EG-DL-I-R), e.g., amino acid residues 99, 100, and 107 (i.e., EG-R) of SEQ ID NO: 4.

In some embodiments, the at least one epitope has the amino acid sequence that is at least 90%, at least about 95%, at least about 96%, at least about 97%, at least about 98%, at least about 99%, or about 100% identical to SEQ ID NO: 6. In some embodiments, the at least one epitope has the amino acid sequence that is at least 90%, at least about 95%, at least about 96%, at least about 97%, at least about 98%, at least about 99%, or about 100% identical to SEQ ID NO: 9.

In some embodiments, the anti-FAM19A5 antibody or antigen binding portion thereof binds to a human FAM19A5 epitope only, which is SEQ ID NO: 5, 6, 7, 8, 9, or 10, or a fragment located within the amino acid sequence of SEQ ID NO: 5, 6, 7, 8, 9, or 10, e.g., an epitope having 1, 2, 3, 4, 5, 6, 7, 8, 9, 10, 11, 12, 13, 14, 15, 16, 17, 18, 19, or 20 amino acids of SEQ ID NO: 5, 6, 7, 8, 9, or 10.

In some embodiments, the anti-FAM19A5 antibody or antigen binding portion thereof of the present disclosure binds to SEQ ID NO: 6 or a fragment thereof in its native conformation (i.e., un-denatured). In some embodiments, the anti-FAM19A5 antibody or antigen binding portion thereof of the present disclosure binds to SEQ ID NO: 9 or a fragment thereof in its native conformation (i.e., un-denatured). In other embodiments, the at least one epitope has the amino acid sequence that is at least 90%, at least about 95%, at least about 96%, at least about 97%, at least about 98%, at least about 99%, or about 100% identical to SEQ ID NO: 5. epitope has the amino acid sequence that is at least 90%, at least about 95%, at least about 96%, at least about 97%, at least about 98%, at least about 99%, or about 100% identical to SEQ ID NO: 10. In some embodiments, the anti-FAM19A5 antibody or antigen binding portion thereof binds to both glycosylated and unglycosylated human FAM19A5.

In some embodiments, the anti-FAM19A5 antibody or antigen binding portion thereof further binds to one or more additional FAM19A5 epitopes. Therefore, certain anti-FAM19A5 antibodies or antigen binding portions thereof bind to an epitope of SEQ ID NO: 6 and an additional epitope or an epitope of SEQ ID NO: 9 and an additional epitope. Other anti-FAM19A5 antibodies or antigen binding portions thereof can bind to an epitope of SEQ ID NO: 5, SEQ ID NO: 9, and an additional epitope. In some embodiments, anti-FAM19A5 antibodies or antigen binding portions thereof bind to an epitope of SEQ ID NO: 6, an epitope of SEQ ID NO: 10, and an additional epitope. In some embodiments, the one or more additional FAM19A5 epitopes are selected from QLAAGTCEIVTLDR (SEQ ID NO: 5, epitope F1), TLDRDSSQPRRTIARQTARC (SEQ ID NO: 6, epitope F2), TARCACRKGQIAGTTRARPA (SEQ ID NO: 7, epitope F3), ARPACVDARIIKTKQWCDML (SEQ ID NO: 8, epitope F4), CDMLPCLEGEGCDLLINRSG (SEQ ID NO: 9, epitope F5), or NRSGWTCTQPGGRIKTTTVS (SEQ ID NO: 10, epitope F6), or a fragment located within the amino acid sequence of SEQ ID NO: 5, SEQ ID NO: 6, SEQ ID NO: 7, SEQ ID NO: 8, SEQ ID NO: 9, or SEQ ID NO: 10, or any combination thereof. A fragment located within the amino acid sequence of SEQ ID NO: 5, SEQ ID NO: 6, SEQ ID NO: 7, SEQ ID NO: 8, SEQ ID NO: 9, or SEQ ID NO: 10, includes a fragment having 1, 2, 3, 4, 5, 6, 7, 8, 9, 10, 11, 12, 13, 14, 15, 16, 17, 18, 19, or 20 amino acids of any of SEQ ID NO: 5, SEQ ID NO: 6, SEQ ID NO: 7, SEQ ID NO: 8, SEQ ID NO: 9, or SEQ ID NO: 10. In some embodiments, the one or more additional FAM19A5 epitopes are selected from SEQ ID NO: 5, 6, 7, 8, 9, or 10, a fragment located within the amino acid sequence of SEQ ID NO: 5, 6, 7, 8, 9, or 10, e.g., a fragment having 1, 2, 3, 4, 5, 6, 7, 8, 9, 10, 11, 12, 13, 14, 15, 16, 17, 18, 19, or 20 amino acids of SEQ ID NO: 5, 6, 7, 8, 9, or 10, or any combination thereof. In some embodiments, the anti-FAM19A5 antibody or antigen binding portion thereof of the disclosure binds to any of the one or more additional epitopes in their native conformation (i.e., un-denatured). In some embodiments, the anti-FAM19A5 antibody or antigen binding portion thereof binds to both glycosylated and unglycosylated of the one or more additional FAM19A5 epitopes.

In some embodiments, anti-FAM19A5 antibodies or antigen binding portions thereof bind to at least one FAM19A5 epitope identified as EP2, EP4, and/or EP8, wherein EP2 comprises, consists essentially of, or consists of the amino acids DSSQP (SEQ ID NO: 66), wherein EP4 comprises, consists essentially of, or consists of the amino acids ARCACRK (SEQ ID NO: 68), and wherein EP8 comprises, consists essentially of, or consists of the amino acids TCTQPGGR (SEQ ID NO: 72). In some embodiments, the at least one epitope has the amino acid sequence that is at least 90%, at least about 95%, at least about 96%, at least about 97%, at least about 98%, at least about 99%, or about 100% identical to EP2, EP4, or EP8. In some embodiments, anti-FAM19A5 antibodies or antigen binding portion thereof only bind to EP2 In some embodiments, anti-FAM19A5 antibodies or antigen binding portion thereof bind to EP4 and EP8.

In some embodiments, the anti-FAM19A5 antibody, or antigen binding portion thereof, binds to at least one FAM19A5 epitope identified as EP6, EP7, or EP8, wherein EP6 comprises the amino acids KTKQWCDML (SEQ ID NO: 70), wherein EP7 comprises the amino acids GCDLLINR (SEQ ID NO: 71), and wherein EP8 comprises the amino acids TCTQPGGR (SEQ ID NO: 72). In some embodiments, the at least one epitope has the amino acid sequence that is at least 90%, at least about 95%, at least about 96%, at least about 97%, at least about 98%, at least about 99%, or about 100% identical to EP6, EP7, or EP8. In some embodiments, the anti-FAM19A5 antibody, or antigen binding portion thereof, only binds to EP6, EP7, or EP8. In some embodiments, the anti-FAM19A5 antibody, or antigen binding portion thereof, binds to EP6, EP7, and EP8. In some embodiments, the anti-FAM19A5 antibody, or antigen binding portion thereof, binds to EP7 and EP8. In some embodiments, the anti-FAM19A5 antibody, or antigen binding portion thereof, binds to EP7.

In some embodiments, anti-FAM19A5 antibodies or antigen binding portion thereof bind to one or more FAM19A5 epitopes selected from the group consisting of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, and any combinations thereof.

In certain embodiments, provided herein is an antibody or antigen binding portion thereof that binds to FAM19A5 (e.g., human FAM19A5) with a 20%, 25%, 30%, 35%, 40%, 45%, 50%, 55%, 60%, 65%, 70%, 75%, 80%, 85%, 90%, 95% or higher affinity than to another protein in the FAM19A family as measured by, e.g., a immunoassay (e.g., ELISA), surface plasmon resonance, or kinetic exclusion assay. In a specific embodiment, provided herein is an antibody or antigen binding portion thereof that binds to FAM19A5 (e.g., human FAM19A5) with no cross reactivity with another protein in the FAM19A family as measured by, e.g., an immunoassay.

In certain embodiments, the anti-FAM19A5 antibodies are not native antibodies or are not naturally-occurring antibodies. For example, the anti-FAM19A5 antibodies have post-translational modifications that are different from those of antibodies that are naturally-occurring, such as by having more, less or a different type of post-translational modification.

IV. Exemplary Anti-FAM19A5 Antibodies

Particular antibodies that can be used in the methods disclosed herein are antibodies, e.g., monoclonal antibodies, having the CDR and/or variable region sequences disclosed herein, as well as antibodies having at least 80% identity (e.g., at least 85%, at least 90%, at least 95%, or at least 99% identity) to their variable region or CDR sequences. The VH and VL amino acid sequences of different anti-FAM19A5 antibodies of the present disclosure are provided in Tables 4 and 5, respectively.

TABLE 2

Variable heavy chain CDR amino acid sequences (according to Kabat system)

| Antibody | VH-CDR1 | VH-CDR2 | VH-CDR3 |
|---|---|---|---|
| Anti-FAM19A5 ("2-13") | SHGMF (SEQ ID NO: 11) | EITNDGSGTNYGSAVKG (SEQ ID NO: 12) | STYECPGGFSCWGDTGQIDA (SEQ ID NO: 13) |
| Anti-FAM19A5 ("3-2") | SFNMF (SEQ ID NO: 14) | QISSSGSSTNYAPAVRG (SEQ ID NO: 15) | SSYDCPYGHCSSGVDSAGEIDA (SEQ ID NO: 16) |
| Anti-FAM19A5 ("1-65") | SYQMG (SEQ ID NO: 17) | VINKSGSDTS (SEQ ID NO: 18) | GSASYITAATIDA (SEQ ID NO: 19) |

TABLE 2-continued

Variable heavy chain CDR amino acid sequences (according to Kabat system)

| Antibody | VH-CDR1 | VH-CDR2 | VH-CDR3 |
|---|---|---|---|
| Anti-FAM19A5 ("1-28") | GFDFSDYG (SEQ ID NO: 20) | IRSDGSNP (SEQ ID NO: 21) | AKDGNGYCALDAYRSGGYSCGVYPGSIDA (SEQ ID NO: 22) |
| Anti-FAM19A5 ("P2-C12") | TYAVT (SEQ ID NO: 89) | YINWRGGTSYANWAKG (SEQ ID NO: 90) | DASSGAAFGSYGMDP (SEQ ID NO: 91) |
| Anti-FAM19A5 ("13B4") | SSNWWS (SEQ ID NO: 95) | EIYHGGTTNYNPSLKG (SEQ ID NO: 96) | WQLVGGLDV (SEQ ID NO: 97) |
| Anti-FAM19A5 ("13F7") | GYSWT (SEQ ID NO: 101) | EISHFGSANYNPSLKS (SEQ ID NO: 102) | ALRGTYSRFYYGMDV (SEQ ID NO: 103) |
| Anti-FAM19A5 ("15A9") | SYYWS (SEQ ID NO: 107) | YIYPSGSTNYNPSLKS (SEQ ID NO: 108) | VNPFGYYYAMDV (SEQ ID NO: 109) |
| Anti-FAM19A5 ("P1-A03") | SDYMS (SEQ ID NO: 113) | IIYPSTITYYASWAKG (SEQ ID NO: 114) | GSNWSSGMNL (SEQ ID NO: 115) |
| Anti-FAM19A5 ("P1-A08") | TYYMS (SEQ ID NO: 119) | IVYPSGTTYYANWAKG (SEQ ID NO: 120) | GDSFGYGL (SEQ ID NO: 121) |
| Anti-FAM19A5 ("P1-F02") | NYYMG (SEQ ID NO: 125) | IIYASGSTYYASWAKG (SEQ ID NO: 126) | IDIGVGDYGWAYDRLDL (SEQ ID NO: 127) |
| Anti-FAM19A5 ("P2-A01") | GYYMS (SEQ ID NO: 131) | IIYPSGSTDYASWAKG (SEQ ID NO: 132) | VAGYVGYGYETFEDI (SEQ ID NO: 133) |
| Anti-FAM19A5 ("P2-A03") | NYDMS (SEQ ID NO: 137) | FMDTDGSAYYATWAKG (SEQ ID NO: 138) | RGSSYYGGIDI (SEQ ID NO: 139) |
| Anti-FAM19A5 ("P2-F07") | SYYMN (SEQ ID NO: 143) | IIYPSGTTYYAGWAKG (SEQ ID NO: 144) | TVSGYFDI (SEQ ID NO: 145) |
| Anti-FAM19A5 ("P2-F11") | SYGVS (SEQ ID NO: 149) | YIANNYNPHYASWAKG (SEQ ID NO: 150) | DNYGMDP (SEQ ID NO: 151) |

TABLE 3

Variable light chain CDR amino acid sequences (according to Kabat system)

| Antibody | VL-CDR1 | VL-CDR2 | VL-CDR3 |
|---|---|---|---|
| Anti-FAM19A5 ("2-13") | SGGSYSYG (SEQ ID NO: 23) | WDDERPS (SEQ ID NO: 24) | GTEDISGTAGV (SEQ ID NO: 25) |
| Anti-FAM19A5 ("3-2") | SGGGSYAGSYYYG (SEQ ID NO: 26) | ESNKRPS (SEQ ID NO: 27) | GSWDSSNGGI (SEQ ID NO: 28) |
| Anti-FAM19A5 ("1-65") | SGGGSSGYGYG (SEQ ID NO: 29) | WNDKRPS (SEQ ID NO: 30) | GNDDYSSDSGYVGV (SEQ ID NO: 31) |
| Anti-FAM19A5 ("1-28") | GYGYG (SEQ ID NO: 32) | QND (SEQ ID NO: 33) | GSEDSSTLAGI (SEQ ID NO: 34) |
| Anti-FAM19A5 ("P2-C12") | QASQSISSYLS (SEQ ID NO: 92) | EASKLAS (SEQ ID NO: 93) | QQGYSSTNVWNA (SEQ ID NO: 94) |
| Anti-FAM19A5 ("13B4") | SGDKLGNVYAS (SEQ ID NO: 98) | QDNKRPS (SEQ ID NO: 99) | QAWDSSTAV (SEQ ID NO: 100) |
| Anti-FAM19A5 ("13F7") | RSSQSLLHSNGYNYLD (SEQ ID NO: 104) | LGSNRAS (SEQ ID NO: 105) | MQARQTPLT (SEQ ID NO: 106) |
| Anti-FAM19A5 ("15A9") | RASQSISTSLN (SEQ ID NO: 110) | GASTLQS (SEQ ID NO: 111) | QESASIPRT (SEQ ID NO: 112) |
| Anti-FAM19A5 ("P1-A03") | LASEDIYSGIS (SEQ ID NO: 116) | GASNLES (SEQ ID NO: 117) | LGGYSYSSTGLT (SEQ ID NO: 118) |
| Anti-FAM19A5 ("P1-A08") | TADTLSRSYAS (SEQ ID NO: 122) | RDTSRPS (SEQ ID NO: 123) | ATSDGSGSNYQYV (SEQ ID NO: 124) |

TABLE 3-continued

Variable light chain CDR amino acid sequences (according to Kabat system)

| Antibody | VL-CDR1 | VL-CDR2 | VL-CDR3 |
|---|---|---|---|
| Anti-FAM19A5 ("P1-F02") | LASEDIYSGIS (SEQ ID NO: 128) | GASNLES (SEQ ID NO: 129) | LGGYSYSSIT (SEQ ID NO: 130) |
| Anti-FAM19A5 ("P2-A01") | LASEDIYSGIS (SEQ ID NO: 134) | GASNLES (SEQ ID NO: 135) | LGGVTYSSTGTHLT (SEQ ID NO: 136) |
| Anti-FAM19A5 ("P2-A03") | QASQSIGGNLA (SEQ ID NO: 140) | RASTLAS (SEQ ID NO: 141) | QSPAYDPAAYVGNA (SEQ ID NO: 142) |
| Anti-FAM19A5 ("P2-F07") | LASEDIYSALA (SEQ ID NO: 146) | GTSNLES (SEQ ID NO: 147) | QGYSSYPLT (SEQ ID NO: 148) |
| Anti-FAM19A5 ("P2-F11") | QASQSVYNNKNLA (SEQ ID NO: 152) | AASTLAS (SEQ ID NO: 153) | QGEFSCSSADCNA (SEQ ID NO: 154) |

TABLE 4

Variable heavy chain amino acid sequence

| Antibody | VH Amino Acid Sequence (SEQ ID NO) |
|---|---|
| Anti-FAM19A5 ("2-13") | AVTLDESGGGLQTPGGALSLVCKASGFTFSSHGMFWVRQTPGKGLEYVAEITNDGSGTNYGSAVKGRATISRDNGQSTVRLQLNNLRAEDTGTYFCARSTYECPGGFSCWGDTGQIDAWGHGTEVIVSS (SEQ ID NO: 35) |
| Anti-FAM19A5 ("3-2") | AVTLDESGGGLQTPGGALSLVCKASGFTFSSFNMFWVRQAPGKGLEYVAQISSSGSSTNYAPAVRGRATISRDNGQSTVRLQLNNPGAEDTGTYYCAKSSYDCPYGHCSSGVDSAGEIDAWGHGTEVIVSS (SEQ ID NO: 36) |
| Anti-FAM19A5 ("1-65") | AVTLDESGGGLQTPGGALSLVCKASGFTFSSYQMGWVRQAPGKGLEWVGVINKSGSDTSYGSAVKGRATISRDNGQSTVRLQLNNLRAEDTGTYFCAKGSASYITAATIDAWGHGTEVIVSS (SEQ ID NO: 37) |
| Anti-FAM19A5 ("1-28") | AVTLDESGGGLQTPGGALSLVCKASGFDFSDYGMGWVRQAPGKGLEWVAAIRSDGSNPSYGSAVKGRATISKDNGRSTVRLQLNNLRAEDTATYYCAKDGNGYCALDAYRSGGYSCGVYPGSIDAWGHGTEVIVSS (SEQ ID NO: 38) |
| Anti-FAM19A5 ("P2-C12") | QSLEESGGRLVTPGTPLTLTCTVSGFSLSTYAVTWVRQAPGKGLEWIGYINWRGGTSYANWAKGRFTISKTSSTTVDLKMTSPTTEDTATYFCARDASSGAAFGSYGMDPWGPGTLVTVSS (SEQ ID NO: 155) |
| Anti-FAM19A5 ("13B4") | QVQLQESGPGLVKPSGTLSLNCAVSGGSISSSNWWSWVRQPPGKGLEWIGEIYHGGTTNYNPSLKGRVTMSVDKTKNQFSLRLSSVTAVDTAVYYCARWQLVGGLDVWGQGTTVTVSS (SEQ ID NO: 156) |
| Anti-FAM19A5 ("13F7") | QVQLQEWGAGLLKPSETLSLTCAINAESFNGYSWTWIRQTPGKGLEWIGEISHFGSANYNPSLKSRATISADKSKNQFSLKLTSVTAVDTAVYYCARALRGTYSRFYYGMDVWGQGTTVTVSS (SEQ ID NO: 157) |
| Anti-FAM19A5 ("15A9") | QVQLQESGPGLVKPSETLSLTCTVSGGSISSYYWSWIRQPPGKGLEWIGYIYPSGSTNYNPSLKSRVTISVDTSKNQFSLNLKSVTAVDTAVYYCARVNPFGYYYAMDVWGQGTTVTVSS (SEQ ID NO: 158) |
| Anti-FAM19A5 ("P1-A03") | QSVEESGGRLVTPGTPLTLTCTVSGFSLSSDYMSWVRQAPGEGLEWIGIIYPSTTTYYASWAKGRFTISKTSSTTVELKMTSLTTEDTATYFCARGSNWSSGMNLWGPGTLVTVSS (SEQ ID NO: 159) |
| Anti-FAM19A5 ("P1-A08") | QSLEESGGRLVTPGTPLTLTCTASGFSLSTYYMSWVRQAPGKGLEWIGIVYPSGTTYYANWAKGRFTISTASTTVDLMITSPTTEDTATYFCARGDSFGYGLWGPGTLVTVSS (SEQ ID NO: 160) |
| Anti-FAM19A5 ("P1-F02") | QSLEESGGRLVTPGTPLTLTCTASGFSLSNYYMGWVRQAPGEGLEWIGIIYASGSTYYASWAKGRFTISKTSTTVDLKMTSLTTEDTATYFCARIDIGVGDYGWAYDRLDLWGQGTLVTVSS (SEQ ID NO: 161) |
| Anti-FAM19A5 ("P2-A01") | QEQLVESGGRLVTPGTPLTLSCTASGFFLSGYYMSWVRQAPGKGLEWIGIIYPSGSTDYASWAKGRFTISKTSTTVDLKITTPTTEDTATYFCARVAGYVGYETFFDIWGPGTLVTVSL (SEQ ID NO: 162) |
| Anti-FAM19A5 ("P2-A03") | QSVEESGGRLVTPGTPLTLTCTVSGFSLNNYDMSWVRQAPGKGLEYIGFMDTDGSAYYATWAKGRFTISRTSTTVDLKMTSPTTEDTATYFCARRGSSYYGGIDIWGPGTPVTVSL (SEQ ID NO: 163) |

TABLE 4-continued

Variable heavy chain amino acid sequence

| Antibody | VH Amino Acid Sequence (SEQ ID NO) |
|---|---|
| Anti-FAM19A5 ("P2-F07") | QSLEESGGRLVTPGTPLTLTCTASGFSLSSYYMNWVRQAPGKGLEWIGIIYPSGTTYYAG WAKGRFTISKTSTTVDLKITSPTSEDTATYFCARTVSGYFDIWGPGTLVTVSL (SEQ ID NO: 164) |
| Anti-FAM19A5 ("P2-F11") | QEQLVESGGRLVTPGTTLTLTCTVSGFSLSSYGVSWVRQAPGKGLEWIGYIANNYNPHYA SWAKGRFTISKTSSTTVDLKMTSLTTEDTATYFCARDNYGMDPWGPGTLVTVSS (SEQ ID NO: 165) |

TABLE 5

Variable light chain amino acid sequence

| Antibody | VL Amino Acid Sequence (SEQ ID NO) |
|---|---|
| Anti-FAM19A5 ("2-13") | ALTQPSSVSANPGETVKITCSGGSYSYGWFQQKSPGSALVTVIYWDDERPSDIPSRFSGA LSGSTNTLTITGVQADDEAVYFCGTEDISGTAGVFGAGTTLTVL (SEQ ID NO: 39) |
| Anti-FAM19A5 ("3-2") | ALTQPSSVSANPGETVKITCSGGGSYAGSYYYGWYQQKAPGSAPVTLIYESNKRPSDIPS RFSGSTSGSTATLTITGVQADDEAIYYCGSWDSSNGGIFGAGTTLTVL (SEQ ID NO: 40) |
| Anti-FAM19A5 ("1-65") | ALTQPSSVSANPGETVKITCSGGGSSGYGYGWYQQKSPSSAPLTVIYWNDKRPSDIPSRF SGSKSGSTHTLTITGVQAEDEAVYFCGNDDYSSDSGYVGVFGAGTTLTVL (SEQ ID NO: 41) |
| Anti-FAM19A5 ("1-28") | ALTQPSSVSANLEGTVEITCSGSGYGYGWYQQKSPGSAPVTVIYQNDKRPSDIPSRFSGS KSGSTGTLTITGVQVEDEAVYYCGSEDSSTLAGIFGAGTTLTVL (SEQ ID NO: 42) |
| Anti-FAM19A5 ("P2-C12") | ELDMTQTPSSVSAAVGGTVTIKCQASQSISSYLSWYQQKPGQPPKLLIYEASKLASGVPS RFSGSGYGTEFTLTISDLECADAATYYCQQGYSSTNVWNAFGGGTNVEIK (SEQ ID NO: 166) |
| Anti-FAM19A5 ("13B4") | SYELTQPLSVSVSPGQTASITCSGDKLGNVYASWYQQKPGQSPTLVIYQDNKRPSGIPER FSGSNSGKTATLTISGTQALDEADYYCQAWDSSTAVFGGGTKLTVL (SEQ ID NO: 167) |
| Anti-FAM19A5 ("13F7") | DIVMTQTPLSLPVAPGEPASISCRSSQSLLHSNGYNYLDWYVQKPGQPPQLLIYLGSNRA SGVPDRFSGSGSGTDFTLKISRVEAEDVGVYYCMQARQTPLTFGGGTKVEIK (SEQ ID NO: 168) |
| Anti-FAM19A5 ("15A9") | DIQMTQSPSSLSASVGDRITISCRASQSISTSLNWYQQTPGKAPRLLIYGASTLQSGVPS RFSGGGSGTDFSLTITSLQPEDFATYYCQESASIPRTFGQGTKLDIK (SEQ ID NO: 169) |
| Anti-FAM19A5 ("P1-A03") | ELVMTQTPPSLSASVGETVRIRCLASEDIYSGISWYQQKPEKPPTLLISGASNLESGVPP RFSGSGSGTDYTLTIGGVQAEDAATYYCLGGYSYSSTGLTFGAGTNVEIK (SEQ ID NO: 170) |
| Anti-FAM19A5 ("P1-A08") | ELVLTQSPSVQVNLGQTVSLTCTADTLSRSYASWYQQKPGQAPVLLIYRDTSRPSGVPDR FSGSSSGNTATLTISGAQAGDEADYYCATSDGSGSNYQYVFGGGTQLTVT (SEQ ID NO: 171) |
| Anti-FAM19A5 ("P1-F02") | ELDMTQTPPSLSASVGETVRIRCLASEDIYSGISWYQQKPGKPPTLLIYGASNLESGVPP RFSGSGSGTDYTLTIGGVQAEDAATYYCLGGYSYSSITFGAGTNVEIK (SEQ ID NO: 172) |
| Anti-FAM19A5 ("P2-A01") | ELVMTQTPPSLSASVGETVRIRCLASEDIYSGISWYQQKPGKPPTLLIYGASNLESGVPP RFSGSGSGSDYTLTIGGVQAEDAATYYCLGGVTYSSTGTHLTFGAGTNVEIK (SEQ ID NO: 173) |
| Anti-FAM19A5 ("P2-A03") | ELDLTQTPASVSEPVGGTVTIKCQASQSIGGNLAWYQQKPGQPPKLLIYRASTLASGVPS RFKGSGSGTDFTLTISDLECADAATYYCQSPAYDPAAYVGNAFGGGTELEIL (SEQ ID NO: 174) |

TABLE 5-continued

Variable light chain amino acid sequence

| Antibody | VL Amino Acid Sequence (SEQ ID NO) |
|---|---|
| Anti-FAM19A5 ("P2-F07") | ELDLTQTPPSLSASVGGTVTINCLASEDIYSALAWYQQKPGKPPTLLISGTSNLESGVPP RFSGSGSGTDYTLTIGGVQAEDAATYFCQGYSSYPLTFGAGTNVEIK (SEQ ID NO: 175) |
| Anti-FAM19A5 ("P2-F11") | ELDLTQTPSSVSAAVGGTVTINCQASQSVYNNKNLAWYQQKPGQPPKLLIYAASTLASGV SSRFKGSGSGTQFTLTISDVQCDDAATYYCQGEFSCSSADCNAFGGGTELEIL (SEQ ID NO: 176) |

Accordingly, provided herein is an isolated anti-FAM19A5 antibody, or an antigen-binding portion thereof, comprising heavy and light chain variable regions, wherein the heavy chain variable region comprises the amino acid sequence of SEQ ID NOs: 35-38 or 155-165. In other embodiments, the isolated anti-FAM19A5 antibody, or an antigen binding portion thereof, comprises the CDRs of the heavy chain variable region selected from the group consisting of SEQ ID NOs: 35-38 or 155-165.

Also provided is an isolated anti-FAM19A5 antibody, or an antigen-binding portion thereof, comprising heavy and light chain variable regions, wherein the light chain variable region comprises the amino acid sequence of SEQ ID NOs: 39-42 or 166-176. In other embodiments, the isolated anti-FAM19A5 antibody, or an antigen binding portion thereof, comprises the CDRs of the light chain variable region selected from the group consisting of SEQ ID NOs: 39-42 or 166-176.

In certain embodiments, the isolated anti-FAM19A5 antibody, or an antigen binding portion thereof, comprises the CDRs of the heavy chain variable region selected from the group consisting of SEQ ID NOs: 35-38 or 155-165 and the CDRs of the light chain variable region selected from the group consisting of SEQ ID NOs: 39-42 or 166-176.

Also provided is an isolated anti-FAM19A5 antibody, or an antigen-binding portion thereof, comprising heavy and light chain variable regions, (i) wherein the heavy chain variable region comprises the amino acid sequence of SEQ ID NO: 35 and wherein the light chain variable region comprises the amino acid sequence of SEQ ID NO: 39; (ii) wherein the heavy chain variable region comprises the amino acid sequence of SEQ ID NO: 36 and wherein the light chain variable region comprises the amino acid sequence of SEQ ID NO: 40; (iii) wherein the heavy chain variable region comprises the amino acid sequence of SEQ ID NO: 37 and wherein the light chain variable region comprises the amino acid sequence of SEQ ID NO: 41; (iv) wherein the heavy chain variable region comprises the amino acid sequence of SEQ ID NO: 38 and wherein the light chain variable region comprises the amino acid sequence of SEQ ID NO: 42; (v) wherein the heavy chain variable region comprises the amino acid sequence of SEQ ID NO: 155 and wherein the light chain variable region comprises the amino acid sequence of SEQ ID NO: 166; (vi) wherein the heavy chain variable region comprises the amino acid sequence of SEQ ID NO: 156 and wherein the light chain variable region comprises the amino acid sequence of SEQ ID NO: 167; (vii) wherein the heavy chain variable region comprises the amino acid sequence of SEQ ID NO: 157 and wherein the light chain variable region comprises the amino acid sequence of SEQ ID NO: 168; (viii) wherein the heavy chain variable region comprises the amino acid sequence of SEQ ID NO: 158 and wherein the light chain variable region comprises the amino acid sequence of SEQ ID NO: 169; (ix) wherein the heavy chain variable region comprises the amino acid sequence of SEQ ID NO: 159 and wherein the light chain variable region comprises the amino acid sequence of SEQ ID NO: 170; (x) wherein the heavy chain variable region comprises the amino acid sequence of SEQ ID NO: 160 and wherein the light chain variable region comprises the amino acid sequence of SEQ ID NO: 171; (xi) wherein the heavy chain variable region comprises the amino acid sequence of SEQ ID NO: 161 and wherein the light chain variable region comprises the amino acid sequence of SEQ ID NO: 172; (xii) wherein the heavy chain variable region comprises the amino acid sequence of SEQ ID NO: 162 and wherein the light chain variable region comprises the amino acid sequence of SEQ ID NO: 173; (xiii) wherein the heavy chain variable region comprises the amino acid sequence of SEQ ID NO: 163 and wherein the light chain variable region comprises the amino acid sequence of SEQ ID NO: 174; (xiv) wherein the heavy chain variable region comprises the amino acid sequence of SEQ ID NO: 164 and wherein the light chain variable region comprises the amino acid sequence of SEQ ID NO: 175; and (xv) wherein the heavy chain variable region comprises the amino acid sequence of SEQ ID NO: 165 and wherein the light chain variable region comprises the amino acid sequence of SEQ ID NO: 176.

Provided herein is an isolated anti-FAM19A5 antibody, or an antigen-binding portion thereof, comprising a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 35-38 or 155-165.

Also provided herein is an isolated anti-FAM19A5 antibody, or an antigen-binding portion thereof, comprising a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 39-42 or 166-176.

Also provided is an isolated anti-FAM19A5 antibody, or an antigen-binding portion thereof, comprising heavy and light chain variable regions, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 35-38 or 155-165, and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 39-42 or 166-176.

In some embodiments, the disclosure provides an isolated anti-FAM19A5 antibody, or an antigen-binding portion thereof, comprising:

(a) heavy and light chain variable region sequences comprising SEQ ID NOs: 35 and 39, respectively;

(b) heavy and light chain variable region sequences comprising SEQ ID NOs: 36 and 40, respectively;

(c) heavy and light chain variable region sequences comprising SEQ ID NOs: 37 and 41, respectively;

(d) heavy and light chain variable region sequences comprising SEQ ID NOs: 38 and 42, respectively;

(e) heavy and light chain variable region sequences comprising SEQ ID NOs: 155 and 166, respectively;

(f) heavy and light chain variable region sequences comprising SEQ ID NOs: 156 and 167, respectively;

(g) heavy and light chain variable region sequences comprising SEQ ID NOs: 157 and 168, respectively;

(h) heavy and light chain variable region sequences comprising SEQ ID NOs: 158 and 169, respectively;

(i) heavy and light chain variable region sequences comprising SEQ ID NOs: 159 and 170, respectively;

(j) heavy and light chain variable region sequences comprising SEQ ID NOs: 160 and 171, respectively;

(k) heavy and light chain variable region sequences comprising SEQ ID NOs: 161 and 172, respectively;

(l) heavy and light chain variable region sequences comprising SEQ ID NOs: 162 and 173, respectively;

(m) heavy and light chain variable region sequences comprising SEQ ID NOs: 163 and 174, respectively;

(n) heavy and light chain variable region sequences comprising SEQ ID NOs: 164 and 175, respectively; or (o) heavy and light chain variable region sequences comprising SEQ ID NOs: 165 and 176, respectively.

In certain embodiments, the anti-FAM19A5 antibody or antigen-binding portion thereof of the present disclosure comprises (i) the heavy chain CDR1, CDR2 and CDR3 of 2-13, or combinations thereof, and/or the light chain CDR1, CDR2, and CDR3 of 2-13, or any combinations thereof; (ii) the heavy chain CDR1, CDR2 and CDR3 of 3-2, or combinations thereof, and/or the light chain CDR1, CDR2, and CDR3 of 3-2, or any combinations thereof; (iii) the heavy chain CDR1, CDR2 and CDR3 of 1-65, or combinations thereof, and/or the light chain CDR1, CDR2, and CDR3 of 1-65, or any combinations thereof; (iv) the heavy chain CDR1, CDR2 and CDR3 of 1-28, or combinations thereof, and/or the light chain CDR1, CDR2, and CDR3 of 1-28, or any combinations thereof; (v) the heavy chain CDR1, CDR2, and CDR3 of P2-C12, or combinations thereof, and/or the light chain CDR1, CDR2, and CDR3 of P2-C12, or any combinations thereof; (vi) the heavy chain CDR1, CDR2, and CDR3 of 13B4, or combinations thereof, and/or the light chain CDR1, CDR2, and CDR3 of 13B4, or any combinations thereof; (vii) the heavy chain CDR1, CDR2, and CDR3 of 13F7, or combinations thereof, and/or the light chain CDR1, CDR2, and CDR3 of 13F7, or any combinations thereof; (viii) the heavy chain CDR1, CDR2, and CDR3 of 15A9, or combinations thereof, and/or the light chain CDR1, CDR2, and CDR3 of 15A9, or any combinations thereof; (ix) the heavy chain CDR1, CDR2, and CDR3 of P1-A03, or combinations thereof, and/or the light chain CDR1, CDR2, and CDR3 of P1-A03, or any combinations thereof; (x) the heavy chain CDR1, CDR2, and CDR3 of P1-A08, or combinations thereof, and/or the light chain CDR1, CDR2, and CDR3 of P1-A08, or any combinations thereof; (xi) the heavy chain CDR1, CDR2, and CDR3 of P1-F02, or combinations thereof, and/or the light chain CDR1, CDR2, and CDR3 of P1-F02, or any combinations thereof; (xii) the heavy chain CDR1, CDR2, and CDR3 of P2-A01, or combinations thereof, and/or the light chain CDR1, CDR2, and CDR3 of P2-A01, or any combinations thereof; (xiii) the heavy chain CDR1, CDR2, and CDR3 of P2-A03, or combinations thereof, and/or the light chain CDR1, CDR2, and CDR3 of P2-A03, or any combinations thereof; (xiv) the heavy chain CDR1, CDR2, and CDR3 of P2-F07, or combinations thereof, and/or the light chain CDR1, CDR2, and CDR3 of P2-F07, or any combinations thereof; or (xv) the heavy chain CDR1, CDR2, and CDR3 of P2-F11, or combinations thereof, and/or the light chain CDR1, CDR2, and CDR3 of F2-F11, or any combinations thereof. The amino acid sequences of the VH CDR1, CDR2, and CDR3 for the different anti-FAM19A5 antibodies disclosed herein are provided in Table 2. The amino acid sequences of the VL CDR1, CDR2, and CDR3 for the different anti-FAM19A5 antibodies disclosed herein are provided in Table 3.

In some embodiments, the anti-FAM19A5 antibody or antigen-binding portion thereof of the disclosure, which specifically binds to human FAM19A5, comprises:

(a) a VH CDR1 comprising the amino acid sequence of SEQ ID NO: 11; and/or (b) a VH CDR2 comprising the amino acid sequence of SEQ ID NO: 12; and/or (c) a VH CDR3 comprising the amino acid sequence of SEQ ID NO: 13.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:

(a) a VL CDR1 comprising the amino acid sequence of SEQ ID NO: 23; and/or (b) a VL CDR2 comprising the amino acid sequence of SEQ ID NO: 24; and/or (c) a VL CDR3 comprising the amino acid sequence of SEQ ID NO: 25.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:

(a) a VH CDR1 comprising the amino acid sequence of SEQ ID NO: 11;

(b) a VH CDR2 comprising the amino acid sequence of SEQ ID NO: 12;

(c) a VH CDR3 comprising the amino acid sequence of SEQ ID NO: 13;

(d) a VL CDR1 comprising the amino acid sequence of SEQ ID NO: 23;

(e) a VL CDR2 comprising the amino acid sequence of SEQ ID NO: 24; and/or (f) a VL CDR3 comprising the amino acid sequence of SEQ ID NO: 25.

In some embodiments, the anti-FAM19A5 antibody or antigen-binding portion thereof of the disclosure, which specifically binds to human FAM19A5, comprises:

(a) a VH CDR1 comprising the amino acid sequence of SEQ ID NO: 14; and/or (b) a VH CDR2 comprising the amino acid sequence of SEQ ID NO: 15; and/or (c) a VH CDR3 comprising the amino acid sequence of SEQ ID NO: 16.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:

(a) a VL CDR1 comprising the amino acid sequence of SEQ ID NO: 26; and/or (b) a VL CDR2 comprising the amino acid sequence of SEQ ID NO: 27; and/or (c) a VL CDR3 comprising the amino acid sequence of SEQ ID NO: 28.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:

(a) a VH CDR1 comprising the amino acid sequence of SEQ ID NO: 14;

(b) a VH CDR2 comprising the amino acid sequence of SEQ ID NO: 15;

(c) a VH CDR3 comprising the amino acid sequence of SEQ ID NO: 16;

(d) a VL CDR1 comprising the amino acid sequence of SEQ ID NO: 26;

(e) a VL CDR2 comprising the amino acid sequence of SEQ ID NO: 27; and/or (f) a VL CDR3 comprising the amino acid sequence of SEQ ID NO: 28.

In some embodiments, the anti-FAM19A5 antibody or antigen-binding portion thereof of the disclosure, which specifically binds to human FAM19A5, comprises:

(a) a VH CDR1 comprising the amino acid sequence of SEQ ID NO: 17; and/or (b) a VH CDR2 comprising the amino acid sequence of SEQ ID NO: 18; and/or (c) a VH CDR3 comprising the amino acid sequence of SEQ ID NO: 19.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:

(a) a VL CDR1 comprising the amino acid sequence of SEQ ID NO: 29; and/or (b) a VL CDR2 comprising the amino acid sequence of SEQ ID NO: 30; and/or (c) a VL CDR3 comprising the amino acid sequence of SEQ ID NO: 31.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:

(a) a VH CDR1 comprising the amino acid sequence of SEQ ID NO: 17;

(b) a VH CDR2 comprising the amino acid sequence of SEQ ID NO: 18;

(c) a VH CDR3 comprising the amino acid sequence of SEQ ID NO: 19;

(d) a VL CDR1 comprising the amino acid sequence of SEQ ID NO: 29;

(e) a VL CDR2 comprising the amino acid sequence of SEQ ID NO: 30; and/or (f) a VL CDR3 comprising the amino acid sequence of SEQ ID NO: 31.

In some embodiments, the anti-FAM19A5 antibody or antigen-binding portion thereof of the disclosure, which specifically binds to human FAM19A5, comprises:

(a) a VH CDR1 comprising the amino acid sequence of SEQ ID NO: 20; and/or (b) a VH CDR2 comprising the amino acid sequence of SEQ ID NO: 21; and/or (c) a VH CDR3 comprising the amino acid sequence of SEQ ID NO: 22.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:

(a) a VL CDR1 comprising the amino acid sequence of SEQ ID NO: 32; and/or (b) a VL CDR2 comprising the amino acid sequence of SEQ ID NO: 33; and/or (c) a VL CDR3 comprising the amino acid sequence of SEQ ID NO: 34.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:

(a) a VH CDR1 comprising the amino acid sequence of SEQ ID NO: 20;

(b) a VH CDR2 comprising the amino acid sequence of SEQ ID NO: 21;

(c) a VH CDR3 comprising the amino acid sequence of SEQ ID NO: 22;

(d) a VL CDR1 comprising the amino acid sequence of SEQ ID NO: 32;

(e) a VL CDR2 comprising the amino acid sequence of SEQ ID NO: 33; and/or (f) a VL CDR3 comprising the amino acid sequence of SEQ ID NO: 34.

In specific embodiments, the anti-FAM19A5 antibody or antigen-binding portion thereof comprises one, two, three, four, five, or six of the CDRs above.

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain and full length light chain combine to form a full length antibody.

Accordingly, in specific embodiments, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which specifically binds to an FAM19A5 polypeptide (e.g., human FAM19A5) comprises a light chain which comprises any VL or VL CDR amino acid sequences described herein, and wherein the constant region of the light chain comprises the amino acid sequence of a human kappa light chain constant region. In a particular embodiment, an antibody described herein, which specifically binds to an FAM19A5 polypeptide (e.g., human FAM19A5) comprises a light chain which comprises a VL or VL CDR amino acid sequences described herein, and wherein the constant region of the light chain comprises the amino acid sequence of a human lambda light chain constant region. Non-limiting examples of human constant region sequences have been described in the art, e.g., see U.S. Pat. No. 5,693,780 and Kabat E A et al, (1991) supra.

With respect to the heavy chain, in some embodiments, the heavy chain of an antibody described herein can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In one embodiment, an antibody described herein, which specifically binds to FAM19A5 (e.g., human FAM19A5), comprises a heavy chain which comprises a VH or VH CDR amino acid sequence described herein, and wherein the constant region of the heavy chain comprises the amino acid sequence of a human gamma (γ) heavy chain constant region. In another embodiment, an antibody described herein, which specifically binds to FAM19A5 (e.g., human FAM19A5), comprises a heavy chain which comprises a VH or VH CDR amino acid sequence disclosed herein, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In some embodiments, an antibody described herein, which specifically binds to FAM19A5 (e.g., human FAM19A5) comprises a VL domain and a VH domain comprising the VH or VH CDRs and VL and VL CDRs described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which specifically binds to FAM19A5 (e.g., human FAM19A5) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any subclass (e.g., IgG1, IgG2, IgG3, IgG4, IgA1 and IgA2) of immunoglobulin molecule. In some embodiments, the constant regions comprise the amino acid sequences of the constant regions of a human IgG, which are naturally-occurring, including subclasses (e.g., IgG1, IgG2, IgG3 or IgG4), and allotypes (e.g., G1m, G2m, G3m, and nG4m) and variants thereof. See, e.g., Vidarsson G. et al. *Front Immunol.* 5:520 (published online Oct. 20, 2014) and Jefferis R. and Lefranc M P, mAbs 1:4, 1-7(2009). In some embodiments, the constant regions comprise the amino acid sequences of the constant regions of a human IgG1, IgG2, IgG3, or IgG4, or variants thereof.

In certain embodiments, the anti-FAM19A5 antibody or antigen-binding portion thereof disclosed herein does not have Fc effector functions, e.g., complement-dependent cytotoxicity (CDC) and/or antibody-dependent cellular phagocytosis (ADCP). Effector functions are mediated by the Fc region and the residues most proximal to the hinge region in the CH2 domain of the Fc region are responsible for effector functions of antibodies as it contains a largely overlapping binding site for C1q (complement) and IgG-Fc receptors (FcγR) on effector cells of the innate immune system. Also, IgG2 and IgG4 antibodies have lower levels of Fc effector functions than IgG1 and IgG3 antibodies. Effector functions of an antibody can be reduced or avoided by different approaches known in the art, including (1) using antibody fragments lacking the Fc region (e.g., such as a Fab, F(ab')$_2$, single chain Fv (scFv), or a sdAb consisting of a monomeric VH or VL domain); (2) generating aglycosylated antibodies, which can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells, see, e.g., U.S. Pub. No. 20120100140); (3) employing Fc regions from an IgG subclass that have reduced effector function (e.g., an Fc region from IgG2 or IgG4 antibodies or a chimeric Fc region comprising a CH2 domain from IgG2 or IgG4 antibodies, see, e.g., U.S. Pub. No. 20120100140 and Lau C. et al. *J. Immunol.* 191:4769-4777 (2013)); and (4) generating an Fc region with mutations that result in reduced or no Fc functions. See e.g., U.S. Pub. No. 20120100140 and U.S. and PCT applications cited therein and An et al. mAbs 1:6, 572-579 (2009).

Thus, in some embodiments, the anti-FAM19A5 antibody or antigen-binding portion thereof disclosed herein is an Fab, an Fab', an F(ab')2, an Fv, a single chain Fv (scFv), or a sdAb consisting of a monomeric VH or VL domain. Such antibody fragments are well known in the art and are described supra.

In some embodiments, the anti-FAM19A5 antibody or antigen-binding portion thereof disclosed herein comprises an Fc region with reduced or no Fc effector function. In some embodiments, the constant regions comprise the amino acid sequences of the Fc region of a human IgG2 or IgG4, in some embodiments, the anti-FAM19A5 antibody is of an IgG2/IgG4 isotype. In some embodiments, the anti-FAM19A5 antibody comprises a chimeric Fc region which comprises a CH2 domain from an IgG antibody of the IgG4 isotype and a CH3 domain from an IgG antibody of the IgG1 isotype, or a chimeric Fc region which comprises a hinge region from IgG2 and a CH2 region from IgG4, or an Fc region with mutations that result in reduced or no Fc functions. Fc regions with reduced or no Fc effector function include those known in the art. See e.g., Lau C. et al. *J. Immunol.* 191:4769-4777 (2013); An et al., mAbs 1:6, 572-579 (2009); and U.S. Pub. No. 20120100140 and the U.S. patents and publications and PCT publications cited therein. Also Fc regions with reduced or no Fc effector function can be readily made by a person of ordinary skill in the art.

V. Nucleic Acid Molecules

Another aspect described herein pertains to one or more nucleic acid molecules that encode any one of the antibodies or antigen-binding portions thereof described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Certain nucleic acids molecules described herein are those encoding the VH and VL sequences of the various anti-FAM19A5 antibodies of the present disclosure. Exemplary DNA sequences encoding the VH sequence of such antibodies are set forth in SEQ ID NOs: 43-46 and 177. Exemplary DNA sequences encoding the VL sequences of such antibodies are set forth in SEQ ID NOs: 47-50 and 178.

TABLE 6

Variable heavy chain polynucleotide sequence

| Antibody | Variable Heavy Chain Polynucleotide Sequence (SEQ ID NO) |
| --- | --- |
| Anti-FAM19A5 (2-13) | GCCGTGACGTTGGACGAGTCCGGGGGCGGCCTCCAGACGCCCGGAGGAGCGCTCAGCCTC GTCTGCAAGGCCTCCGGGTTCACCTTCAGCAGCCATGGCATGTTCTGGGTGCGACAGACG CCCGGCAAGGGGTTGGAATATGTCGCTGAAATTACCAATGATGGTAGTGGCACAAACTAC GGGTCGGCGGTGAAGGGCCGTGCCACCATCTCGAGGGACAACGGCCAGAGCACAGTGAGG CTGCAGCTGAACAACCTCAGGGCTGAGGACACCGGCACCTACTTCTGCGCCAGATCTACT TATGAATGTCCTGGTGGTTTTAGTTGTTGGGGTGATACTGGTCAAATAGACGCATGGGGC CACGGGACCGAAGTCATCGTCTCCTCCA (SEQ ID NO: 43) |
| Anti-FAM19A5 (3-2) | GCCGTGACGTTGGACGAGTCCGGGGGCGGCCTCCAGACGCCCGGAGGAGCGCTCAGCCTC GTCTGCAAGGCCTCCGGGTTCACCTTCAGCAGCTTCAACATGTTCTGGGTGCGACAGGCG CCCGGCAAGGGGCTGGAATACGTCGCTCAAATTAGCAGCAGTGGTAGTAGCACAAACTAC GCACCCGCGGTGAGGGGCCGTGCCACCATCTCGAGGGACAACGGGCAGAGCACAGTGAGG CTGCAGCTGAACAACCCCGGGGCTGAAGACACCGGCACCTACTACTGCGCCAAAAGTAGT TATGACTGTCCTTACGGTCATTGTAGTAGTGGTGTTGATAGTGCTGGTGAGATCGACGCA TGGGGCCACGGGACCGAAGTCATCGTCTCCTCCA (SEQ ID NO: 44) |
| Anti-FAM19A5 (1-65) | GCCGTGACACTGGACGAATCTGGGGGAGGGCTGCAGACTCCAGGCGGAGCTCTGAGCCTG GTGTGCAAGGCATCCGGGTTCACCTTTAGCTCCTACCAGATGGGATGGGTGCGGCAGGCA CCAGGGAAGGGCCTGGAGTGGGTCGGAGTGATCAACAAATCTGGGAGTGACACAAGCTAC GGCAGCGCCGTGAAGGGAAGGGCCACCATCAGCAGGGACAATGGCCAGAGTACCGTGCGG CTGCAGCTGAACAATCTGCGCGCTGAGGACACTGGCACCTACTTCTGTGCTAAGGGATCA GCAAGCTATATCACAGCCGCTACTATTGATGCATGGGGACACGGGACAGAAGTCATCGTG TCTAGT (SEQ ID NO: 45) |
| Anti-FAM19A5 (1-28) | GCCGTGACGTTGGACGAGTCCGGGGGCGGCCTCCAGACGCCCGGAGGAGCGCTCAGCCTC GTCTGCAAGGCCTCCGGGTTCGACTTCAGCGATTATGGCATGGGTTGGGTGCGACAGGCT CCAGGCAAGGGGCTGGAGTGGGTTGCTGCTATTAGAAGTGATGGTAGTAACCCATCATAC GGGTCGGCGGTGAAGGGCCGTGCCACCATCTCGAAGGACAACGGGCGAAGCACAGTGAGG CTGCAGCTGAACAACCTCAGGGCTGAGGACACCGCCACCTACTACTGCGCCAAGGATGGT AATGGTTACTGTGCTCTCGATGCTTATCGTAGTGGTGGTTATAGTTGTGGTGTTTATCCT GGTAGCATCGACGCATGGGGCCACGGGACCGAAGTCATCGTCTCCTCC (SEQ ID NO: 46) |
| Anti-FAM19A5 (P2-C12) | CAGTCGCTGGAGGAGTCCGGGGGTCGCCTGGTCACGCCTGGGACACCCCTGACACTCACC TGCACCGTCTCTGGATTCTCCCTCAGTACCTATGCAGTGACCTGGGTCCGCCAGGCTCCA GGGAAGGGGCTGGAATGGATCGGATACATTAATTGGCGTGGTGGGACATCCTACGCGAAC TGGGCGAAAGGCCGATTCACCATCTCCAAAACCTCGTCGACCACGGTGGATCTGAAAATG ACCAGTCCGACAACCGAGGACACGGCCACCTATTTCTGTGCCAGAGATGCTAGTAGTGGT GCTGCTTTTGGGTCTTACGGCATGGACCCCTGGGGCCCAGGGACCCTCGTCACCGTCTCT TCA (SEQ ID NO: 177) |

TABLE 7

Variable light chain polynucleotide sequence

| Antibody | Variable Light Chain Polynucleotide Sequence (SEQ ID NO) |
| --- | --- |
| Anti-FAM19A5 (2-13) | GGCCCTGACTCAGCCGTCCTCGGTGTCAGCAAACCCAGGAGAAACCGTCAAGATAACCTG CTCCGGGGGTAGCTATAGCTATGGCTGGTTCCAGCAGAAGTCTCCTGGCAGTGCCCTTGT CACTGTGATCTACTGGGATGATGAGAGACCCTCGGACATCCCTTCACGATTCTCCGGTGC CCTATCCGGCTCCACAAACACATTAACCATCACTGGGGTCCAAGCCGACGACGAGGCTGT CTATTTCTGTGGGACTGAAGACATCAGCGGCACTGCTGGTGTATTTGGGCCGGGACAAC CCTGACCGTCCTGGG (SEQ ID NO: 47) |

TABLE 7-continued

Variable light chain polynucleotide sequence

| Antibody | Variable Light Chain Polynucleotide Sequence (SEQ ID NO) |
|---|---|
| Anti-FAM19A5 (3-2) | GGCCCTGACTCAGCCGTCCTCGGTGTCAGCAAACCCAGGAGAAACCGTCAAGATCACCTG CTCCGGGGGTGGCAGCTATGCTGGAAGTTACTATTATGGCTGGTACCAGCAGAAGGCACC TGGCAGTGCCCCTGTCACTCTGATCTATGAAAGCAACAAGAGACCCTCGGACATCCCTTC ACGATTCTCCGGTTCCACATCTGGCTCCACAGCCACACTAACCATCACTGGGGTCCAAGC CGATGACGAGGCTATCTATTACTGTGGGAGCTGGGACAGTAGCAATGGTGGTATATTTGG GGCCGGGACAACCCTGACCGTCCTAGG (SEQ ID NO: 48) |
| Anti-FAM19A5 (1-65) | GCCCTGACTCAGCCCTCTTCCGTGTCAGCCAACCCTGGAGAAACTGTGAAGATCACCTGC AGCGGAGGAGGGAGCTCCGGATACGGATATGGGTGGTATCAGCAGAAATCCCCATCTAGT GCCCCCCTGACTGTGATCTATTGGAACGACAAGAGGCCTAGTGATATTCCATCAAGATTC AGTGGATCAAAAAGCGGGTCCACTCACACCCTGACAATCACTGGCGTGCAGGCAGAGGAC GAAGCCGTCTACTTCTGCGGAAATGACGATTACTCAAGCGATTCTGGCTATGTGGGCGTC TTTGGCGCAGGAACCACACTGACAGTGCTG (SEQ ID NO: 49) |
| Anti-FAM19A5 (1-28) | GCCCTGACTCAGCCGTCCTCGGTGTCAGCAAACCTGGAAGGAACCGTCGAGATCACCTGC TCCGGGAGTGGCTATGGTTATGGCTGGTATCAGCAGAAGTCTCCTGGCAGTGCCCCTGTC ACTGTGATCTATCAGAACGACAAGAGACCCTCGGACATCCCTTCACGATTCTCCGGTTCC AAATCCGGCTCCACGGGCACATTAACCATCACTGGGGTCCAAGTCGAGGACGAGGCTGTC TATTACTGTGGGAGTGAAGACAGCAGCACTCTTGCTGGTATATTTGGGGCCGGGACAACC CTGACCGTCCTA (SEQ ID NO: 50) |
| Anti-FAM19A5 (P2-C12) | GAGCTCGATATGACCCAGACTCCATCCTCCGTGTCTGCAGCTGTGGGAGGCACAGTCACC ATCAAGTGCCAGGCCAGTCAGAGCATTAGTAGCTACTTATCCTGGTATCAGCAGAAACCA GGGCAGCCTCCCAAGCTCCTGATCTATGAAGCATCCAAACTGGCCTCTGGGGTCCCATCG CGGTTCAGCGGCAGTGGATATGGGACAGAGTTCACTCTCACCATCAGCGACCTGGAGTGT GCCGATGCTGCCACTTACTACTGTCAACAGGGTTATAGTAGTACTAATGTTTGGAATGCT TTCGGCGGAGGCACCAATGTGGAAATCAAA (SEQ ID NO: 178) |

A method for making an anti-FAM19A5 antibody as disclosed herewith can comprise expressing the relevant heavy chain and light chain of the antibody in a cell line comprising the nucleotide sequences encoding the heavy and light chains with a signal peptide, e.g., SEQ ID NOs: 43 and 47, SEQ ID NOs: 44 and 48, SEQ ID NOs: 45 and 49, SEQ ID NOs: 46 and 50, SEQ ID NOs: 177 and 178, respectively. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG2 and/or IgG 4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see, e.g., Bird et al. (1988) Science 242:423-426; Huston et al. (1988) Proc. Natl. Acad. Sci. USA 85:5879-5883; McCafferty et al., (1990) Nature 348:552-554).

In some embodiments, the present disclosure provides a vector comprising an isolated nucleic acid molecule comprising a nucleotide sequence encoding an antibody or antigen-binding portion thereof. In other embodiments, the vectors can be used for gene therapy.

Suitable vectors for the disclosure include expression vectors, viral vectors, and plasmid vectors. In one embodiment, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure can include polynucleotides encoding the antibody or antigen-binding portion thereof described herein. In one embodiment, the coding sequences for the antibody or antigen-binding portion thereof is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody or antigen-binding portion thereof.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In other embodiments, the vector is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The disclosure provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the disclosure comprising the FVIII nucleotide sequence described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, WO9712622, WO9817815, WO9817816, and WO9818934, which are incorporated herein by reference in their entireties.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

VI. Antibody Production

Antibodies or fragments thereof that immunospecifically bind to FAM19A5 (e.g., human FAM19A5) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

VII. Pharmaceutical Compositions

Provided herein are compositions comprising an antibody or antigen-binding portion thereof described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an antibody or antigen-binding portion thereof, a bispecific molecule, or a immunoconjugate described herein, and optionally one or more additional prophylactic or therapeutic agents, in a pharmaceutically acceptable carrier. In a specific embodiment, pharmaceutical compositions comprise an effective amount of an antibody or antigen-binding portion thereof described herein, and optionally one or more additional prophylactic of therapeutic agents, in a pharmaceutically acceptable carrier. In some embodiments, the antibody is the only active ingredient included in the pharmaceutical composition. Pharmaceutical compositions described herein can be useful in reducing a FAM19A5 activity and thereby treat an ocular disease, disorder, or condition, such as a glaucoma.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition can be formulated for any route of administration to a subject. Specific examples of routes of administration include intranasal, oral, parenterally, intrathecally, intra-cerebroventricularly, pulmonarily, subcutaneously, or intraventricularly. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody or antigen-binding portion thereof described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflations, alone or in combination with an inert carrier such as lactose. In such a case, the particles of the formulation will, in one embodiment, have diameters of less than 50 microns, in one embodiment less than 10 microns.

An antibody or antigen-binding portion thereof described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody or antigen-binding portion thereof described herein is a lyophilized powder, which can be reconstituted for administration as solutions, emulsions and other mixtures. It can also be reconstituted and formulated as solids or gels. The lyophilized powder is prepared by dissolving an antibody or antigen-binding portion thereof described herein, or a pharmaceutically acceptable derivative thereof, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The antibodies or antigen-binding portions thereof, the bispecific molecule, or the immunoconjugate described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In a specific embodiment, the anti-FAM19A5 antibody or antigen-binding portion thereof described herein can be used to treat a glaucoma and/or reduce, ameliorate, or inhibit inflammation associated with a glaucoma.

The compositions to be used for in vivo administration can be sterile. This is readily accomplished by filtration through, e.g., sterile filtration membranes.

VIII. Kits

Provided herein are kits comprising one or more antibodies described herein, or antigen-binding portions thereof, bispecific molecules, or immunoconjugates thereof. In a specific embodiment, provided herein is a pharmaceutical pack or kit comprising one or more containers filled with one or more of the ingredients of the pharmaceutical compositions described herein, such as one or more antibodies provided herein or an antigen-binding portion thereof, optional an instructing for use. In some embodiments, the kits contain a pharmaceutical composition described herein and any prophylactic or therapeutic agent, such as those described herein.

EXAMPLES

The following experimental methods and details are referenced in the Examples that follow.

Example 1

Expression and Purification of Human FAM19A5 Protein

Recombinant human FAM19A5 protein was produced and purified as described below and the purified protein was used in an antibody screening assay based on binding affinity analysis. First, LPS-hT plasmid expressing the FAM19A5 gene was transformed into bacteria and protein over-expression was induced. Once produced, the FAM19A5 protein was purified using an Ni-NTA affinity chromatography (Qiagen, Valencia, Calif., USA)). Using gradually higher concentration of imidazole, we removed the His-tagged FAM19A5 protein from the Ni-column. The protein expression in the solution is measured using Coomassie Brilliant Blue R-250 Dye. Taking only the FAM19A5 immidazole containing solution, we concentrated the FAM19A5 protein using PBS. When the concentration was complete, both the purity and concentration of the FAM19A5 protein were measured using a Western Blot assay. The concentrated protein was subsequently used to screen for FAM19A5-specific antibodies.

Example 2

Production of Antibody Libraries FAM19A5

1. Immunization

A FAM19A5 peptide was synthesized, conjugated at the C-terminal end to KLH (Anygen), and used as antigen for immunization of a chicken. 50 µg of the synthetic peptide KLH conjugate (KLH-VTLDRDSSQPRRTIARQT) (SEQ ID NO: 201) was mixed in 750 µL phosphate buffered saline (PBS) and incubated at 37° C. for 30 minutes. Afterwards, the toxin is removed in a 2% squalene endotoxin MPL (monophosphorylate lipid A species) and mycobacteria (mycobacteria) of the cell wall components of TDW and CWS containing a water-in-oil emulsion adjuvant (RIBI+MPL+TDM+CWS adjuvant, Sigma, St. Louis, Mo, USA) in emulsified, which was then subcutaneously injected into three chickens. The chickens were immunized for a total of three times, approximately 2-3 weeks apart between immunization. The titer of the antibodies obtained from the immunized chickens was measured via immune blotting using lysates of HEK293T cells which overexpressed the FAM19A5 protein. Sera from chickens that received the three immunizations were used as primary antibody. The secondary antibody used was anti-chicken IgG(Y) polyclonal antibody conjugated to HRP (Horseradish peroxidase) (Rabbit anti-chicken IgG (Y)-HRP, Millipore corporation, Billeria, Mass., USA).

2. Preparing of Single-Chain Variable Fragment (scFv) Library from Immunized Chicken Using TRI reagent (Invitrogen, Carlsbad, Calif. USA), we extracted RNAs from the spleen, bone marrow, and synovial sac of the immunized chickens described above. Oligo-dT primers and SUPERSCRIPT™ III First-Strand Synthesis System (Invitrogen) were used to synthesize the first strand cDNA. For the cDNA obtained from the immune system of chickens, Expand High Fidelity PCR System (Roche Molecular Systems, Ind., USA) was used to produce a single chain variable region library. In each reaction, 1 µL of cDNA, 60 pmol of each primer, 10 µL of 10× reaction buffer solution, 8 µL of 2.5 mM dNTP (Promega, Madison, Wis., USA), and 0.5 µL of Taq DNA polymerase were mixed with water. The final volume was 100 µL. PCR reaction was performed using the following conditions: 30 cycles of (i) 15 seconds at 94° C. (ii) 30 seconds at 56° C., and (iii) 90 seconds at 72° C., followed by a final extension for 10 minutes at 72° C. The PCR products comprising a fragment having a length of about 350 bp where loaded onto a 1.5% agarose gel and after electrophoresis, QIAGEN Gel II Extraction Kit (QIAGEN, Valencia, Calif., USA) was used to purify the nucleotide fragment. The purified PCR product was quantified by reading at OD 260 nm. (1 unit OD=50 µg/ml).

Two VH and VL first product from the second PCR was connected randomly by the overlap extension PCR (Overlap extension PCR). Each PCR reaction was mixed with 100 ng of the purified VL and VH product, 60 pmol of each primer, 10 µL 10× rection buffer, 8 µL of 2.5 mM dNTP, 0.5 µL of Taq DNA polymerase, and water in a final volume of 100 of. PCR was performed under the following conditions: 25 cycles of (i) 15 seconds at 94° C., (ii) 30 seconds at 56° C., and (iii) 2 minutes at 72° C., followed by final extension for 10 minutes at 72° C. The PCR products comprising a single chain variable region fragment having a length of about 700 bp were loaded onto a 1.5% agarose gel and after electrophoresis, QIAGEN II Gel Extraction Kit (QIAGEN) was used to purify the nucleotide fragment. The purified PCR product was quantified by reading at OD 260 nm. (1 unit OD=50/ml).

3. Library, Ligation and Transformation

The scFv fragment of the PCR product and vector pComb3X-SS (The Scripps Research Institute, Calif., USA) were digested with a Sfi I restriction enzyme. 10 µg of the purified overlapping PCT product was mixed with 360 units of Sif I, (µg DNA per 16 units, Roche Molecular Systems, Pleasanton, Calif., USA), 20 µL of a 10× reaction buffer, and water to the final volume with 200 µL. 20 µg of the pComb3X-SS vector was mixed with 120 units of Sfi I (µg DNA per 6 units), 20 µL of a 10× reaction buffer solution, and water to the final volume to 200 µL. The mixture was digested at 50° C. for 8 hours. Afterwards, the digested product comprising the scFv fragment (about 700 bp) and the vector (about 3400 bp) was loaded onto a 1% agarose gel and purified using a Gel Extraction Kit II QIAGEN (QIAGEN, Valencia, Calif., USA). 1400 ng of the Sfi I-restricted pComb3X vector and 700 ng of the digested scFv fragments were mixed with 5× a ligase buffer, 10 µL of T4 DNA ligase (Invitrogen, Carlsbad, Calif., USA), and water to a final volume of 200 µL. The mixture was incubated at 16° C. for 16 hours to perform the ligation.

After precipitation with ethanol, the DNA pellet was dissolved in 15 µL of water. To produce a library, the ligation sample was transformed into *E. coli* strain ER2738 (New England Biolabs Inc, Hitchin, Hertfordshine, SG4 OTY, England, UK) via electroporation using the vibrator gene (Gene pulser: Bio-Rad Laboratories, Hercules, Calif., USA). Cells were mixed in a 5 ml Super Broth (SB) medium and incubated while stirring at 250 rpm for one hour at 37° C. Then, 3 µL of 100 mg/mL kanamycin was added to 10 mL of SB medium. To determine the library size, 0.1 µL, 1 µL and 10 µL of the culture sample were smeared onto Luria Broth (LB) agar plates containing 50 µg/ml of kanamycin. After stirring for 1 hour, 4.5 µL of 100 mg/mL kanamycin was added to the LB culture and further stirred for an additional 1 hour. Then, 2 ml of the VCM13 helper phage in water (>$10^{11}$ cfu/ml) was added to the LB medium, along with pre-heated LB (183 mL) containing 92.5 µL of 100 mg/mL kanamycin. This mixture was stirred at 250 rpm at 37° C. for an additional 2 hours. Next, 280 µL (50 mg/mL) of kanamycin was added to the culture and stirred overnight at 37° C. The next day, the bacteria pellet was centrifuged using a high-speed centrifuge (Beckman, JA-10 rotor) at 3,000 g, 4° C. Afterwards, the bacterial pellet was used to extract phagemid DNA, while the supernatant was transferred to sterile centrifuge bottles. Next 8 grams of polyethylene glycol –8000 (PEG-8000, Sigma) and 6 grams of sodium chloride was added (NaCl, Merck) to the supernatant, and then kept for 30 minutes in ice. Afterwards, the supernatant was centrifuged 15 minutes at 15,000 g, 4° C. The supernatant was then discarded, and the phage pellet Tris containing 1% BSA-reproduction was suspended in buffered saline (TBS).

Example 3

Library Panning (Bio-Panning) on an Immobilized Antigen

Bio-panning was performed using magnetic beads (Dynabeads M-270 Epoxy, Invitrogen). At room temperature, approximately $1\times10^7$ beads were coated with 5 µg of recombinant FAM19A5 protein by stirring, while rotating, the beads and the protein together for 20 hours at room temperature. Once the coating was done, the beads were washed 4 times with phosphate buffered saline (PBS) and blocked for one hour in PBS containing 3% BSA at room temperature. Then, the coated beads were cultured for two hours at room temperature with Phage-displayed scFv described above. To remove any phage that was not bound to the antigen coated beads, the beads were washed with 0.05% Tween20/PBS. Then the bound phages were eluted with 50 µL of 0.1M glycine/hydrogen chloride (0.1M Glycine-HCl, pH 2.2) and neutralized with 3 µL of 2M Tris with hydrogen chloride (tris-HCl, pH 9.1). This phage-containing supernatants were used to infect *E. coli* ER2738 cells and VCSM13 helper phage was used to amplify and rescue overnight. Also the input (input) and production (output) by phage titers from the phage-infected cultures were determined by blotting the phage-infected cultures on LB agar plates containing 50 µg/ml of kanamycin. The next day, PEG-8000 and NaCl were used to precipitate phages, which were used subsequently for bio-panning. Bio-panning was performed up to a total of five different times by repeating the above process. With each amplification, the phages were screened and selected for high affinity to the FAM19A5 protein.

Example 4

Selection of Clone by Phage ELISA

To analyze the clones selected from the bio-panning, we randomly selected individual clones from the phase-displayed scFv and confirmed using ELISA that the clones bind to the FAM19A5 recombinant protein. The FAM19A5 recombinant protein was diluted in 0.1M $NaHCO_3$ buffer, and 100 ng/well of the protein was used to coat 96-well microtiter plates at 4° C. for 16 hours. Next day, the plates were blocked with 3% BSA/PBS at 37° C. for 1 hour. Then, the phage supernatant was mixed with 6% BSA/PBS and was cultured for 2 hours at 37° C. The plates containing the supernatant were then washed with 0.05% Tween20/PBS. The HRP-conjugated M13 antibody (a-M13-HRP, Pierce Chemical Co, Rockford, Ill., USA) was diluted to 1/5000. 50 µl of the diluted antibody was added to the plates and incubated for 1 hour at 37° C. After the incubation and washing, the plates were added with 0.05M citrate buffer solution, 1 µg/ml of 2,2'-azino-bis (3-ethylbenzothiazoline-6-sulphonic acid) (ABTS, Amresco, Solon, Ohio, USA), and 0.1% $H_2O_2$ for color development. The absorbance for each well was measured at 405 nm.

In total, we analyzed 24 clones that bind to the FAM19A5 recombinant protein and show high absorbance and from the 24 clones, we obtained 13 scFv clones having unique sequences. After further selecting the clones, we obtained clone 1-65, 2-13, and 3-2 having the highest affinity.

Example 5

Production of Anti-FAM19A5-IgG2/4 Antibody

1. Sub-Cloning of Anti-FAM19A5 scFv into a Mammalian Expression Vector

In the FAM19A5 scFv gene sequence, a human Cκ gene was connected to the light chain variable domain, and human immunoglobulin isotype IgG2/4 of CH1, CH2, and CH3 genes were connected to the heavy chain variable region. The antibody having each light chain and each heavy chain was synthesized by adding restriction sites (Genscript, USA). The synthesized gene was inserted into the mammalian cell expression vector having a modified restriction site to facilitate cloning. First, the light chain gene was inserted into the vector using Hind III and Xba I (New England Biolabs, UK) restriction enzymes and then adding the heavy chain gene to the vector by using NheI and BamHI (New England Biolabs, UK) restriction enzymes.

2. Purification of the anti-FAM19A5 Antibody

In order to express and purify an anti-FAM19A5-IgG2/4 antibody, we used a mammalian cell transfection and overexpression injection system. We mixed 2 µg/ml of the mammalian expression vector with 4 µg of polyethyleneimine (PEI, Polysciences, Warrington, Pa., USA) in 150 mM sodium chloride (NaCl, Merck) corresponding to 1/10 of the cell culture volume. The mixture was allowed to stand for 15 minutes at room temperature. The mixture was added to HEK293F cells ($2\times10^6$ cells/ml, Invitrogen), which were then incubated in the FREESTYLE™ 293 expression culture medium containing 100 U/ml of penicillin and streptomycin (Invitrogen) at 7% $CO^2$ and 37° C. and in a stirring condition of 135 rpm for six days. To purify the expressed anti-FAM19A5 IgG2/4 antibodies from the cell culture supernatant, we used Protein A bead (RepliGen, Waltham, Mass., USA) affinity gel chromatography. The protein A chromatography purified antibody was run on 4~12% Bis-Tris gradient gel electrophoresis. The size and yield of the protein was confirmed by the Coomassie Brilliant Blue staining.

Example 6

Evaluation of Intraocular Pressure after In Vivo Administration of Anti-FAM19A5 Antibody In order to assess whether the neutralization of FAM19A5 activity in vivo could relieve elevated intraocular pressure often associated with glaucoma, a rabbit model of glaucoma was used. Briefly, New Zealand White rabbits (male, 2-2.5 kg in weight) (Hanlim Experiment Animal Research Institute, Kyonggi-Do, South Korea) were deeply anesthetized with Zoletil 50 (VIRBAC, France) and zylazine (Rompun®, Bayer AG, Germany). Then, the orbital cavity was exposed by raising the rabbit's eyes from the orbit. For each eye, the episcleral vein located above and below the exposed eye was cauterized using an electrocautery machine at a depth sufficient to occlude the episcleral vein without affecting the sclera and other adjacent vessels.

Approximately two weeks after glaucoma induction (i.e., day 0), the rabbits received either normal human IgG immunoglobulin (control) or anti-FAM19A5 antibody in each eye via intravitreal injection (100 μg/eye in 50 μL volume). The animals received the antibodies once a week for a total of 4 weeks. Naïve (i.e., no glaucoma and no antibody injection) rabbits were used as additional control. At days 0, 14, and 28 post glaucoma induction, the intraocular pressure was measured using a TonoVet®. As shown in FIG. 1, for all time points measured, the anti-FAM19A5 antibody had no effect on the intraocular pressure of the rabbits. Rabbits receiving the IgG control antibody or the anti-FAM19A5 antibody had similarly elevated intraocular pressure as compared to the naïve animals.

Example 7

Evaluation of the Retinal Potential Difference after In Vivo Administration of Anti-FAM19A5 Antibody Electroretinogram (ERG) is a diagnostic test that measures the electrical activity generated by various cells in the retina, including the photoreceptors (rods and cones), inner retinal cells (bipolar and amacrine cells), and the ganglion cells. Generally, upon a bright stimulus flash, the ERG of a healthy eye will exhibit a complex waveform consisting of an initial negative deflection ("A-wave") followed by a B-wave with an increasingly steeper rise and faster peak upon which are superimposed higher-frequency oscillations known as "oscillatory potentials" (OPs). The A-wave is dominated by the collective response of the rods and the scotopic B-wave by the response of rod bipolar neurons. The OPs arise within the inner plexiform layer, where the bipolar, amacrine, and ganglion cells interact. Wilsey et al., *Curr Opin Ophthalmol* 27(2): 118-124 (2016). By assessing these values, it may be possible to assess the health of the different cells found within the retina.

As detailed above in Example 6, glaucoma was induced in New Zealand White rabbits and the animals were injected in each eye with either the human IgG control antibody or the anti-FAM19A5 antibody. At 4 weeks after the initial administration of the anti-FAM19A5 antibody, the following values were measured to assess the electrical activity (i.e., "retinal potential difference") within the animals' eyes: (i) the reaction time (time to peak amplitude) for the A wave ("A-time") and (ii) the oscillatory potential.

Figure 2:
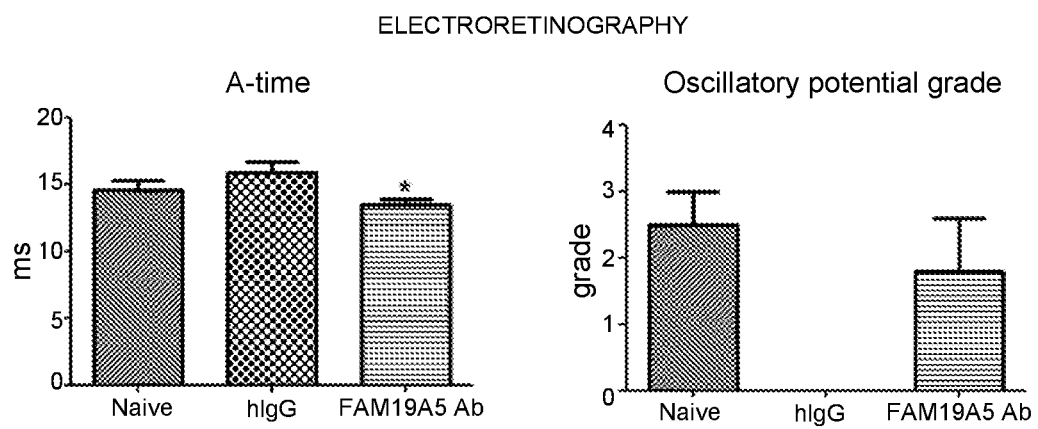
FIG. 2 shows a comparison of the results from the electroretinography (ERG) measurements in glaucoma-induced animals treated with human IgG1 ("hIgG") or an anti-FAM19A5 antibody ("FAM19A5 Ab") against healthy animals ("naive"). At day 28 post glaucoma induction, the retinal potential difference in the different animals was assessed by analyzing the A-time (left panel) and the oscillatory potential grade (right panel). Data are expressed as mean±S.D. "*" above the bars indicates a statistically significant difference ($p<0.001$) compared to IgG1-treated animals.

As shown in FIG. 2, in animals that received the anti-FAM19A5 antibody, there was marked improvement in the A-time as compared to those animals that received the control antibody (left panel). The A-time for animals that received the anti-FAM19A5 antibody was more comparable to that of the naïve (i.e., healthy) animals. Similarly, administration of the anti-FAM19A5 antibody significantly improved the oscillatory potential measured in the glaucoma-induced rabbits (right panel). In the animals that received the IgG control antibody, no detectable oscillatory potential was measured. In contrast, the oscillatory potential in the animals that received the FAM19A5-specific antibody were comparable to that of the naïve animals. Collectively, these results suggest that the administration of the anti-FAM19A5 antibody to glaucoma-induced rabbits can improve retinal damage associated with glaucoma.

Example 8

Evaluation of the Retinal Ganglion Cell Frequency after In Vivo Administration of Anti-FAM19A5 Antibody To confirm the results from the ERG analysis above, glaucoma was again induced in New Zealand White rabbits and the animals were injected in each eye with either the human IgG control antibody or the anti-FAM19A5 antibody as described in Example 6. Then, at 4 weeks after the initial administration of the anti-FAM19A5 antibody, the animals were sacrificed. Both eyes from each of the animals were harvested and fixed in 10% neutral buffered formalin solution for approximately 24 hours. Afterwards, the eyes were washed with PBS and then, the cornea, lens, and the vitreous membrane were separated. Then, the eyes were made into a cup-shape and fixed in 50% methanol for 30 minutes. The eyes were next washed with sterile distilled water, and each eye was placed in a well of a 12-well plate. Approximately 0.5 mL of 0.1% ethidium bromide was added to each of the wells, and the eyes were incubated in this solution for 30 minutes. After the incubation, the eyes were washed with sterile distilled water and mounted onto a 60 mm dish. The number of cells in the retinal ganglion cell layer was measured using a fluorescence microscope.

Figure 3A:
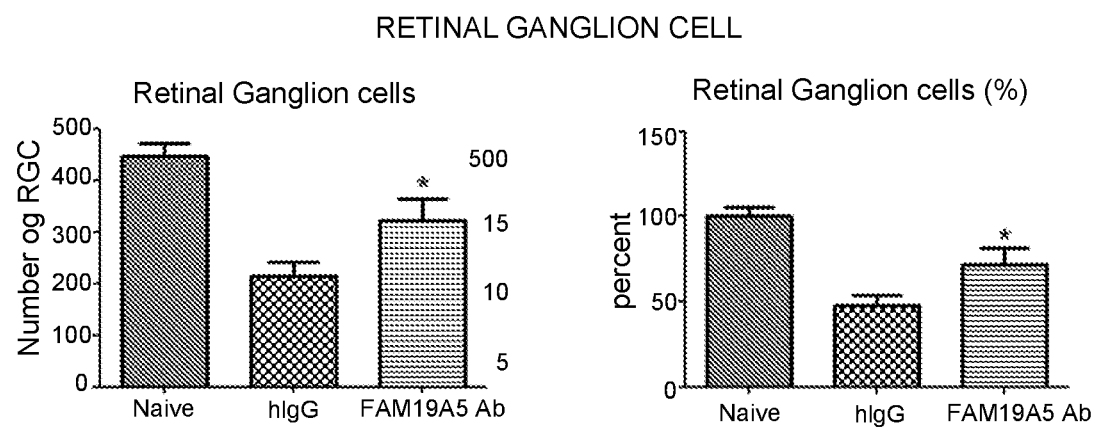
FIGS. 3A and 3B show a comparison of the number of retinal ganglion cells ("RGC") observed in the retinal ganglion cell layer of glaucoma-induced animals treated with human IgG1 ("hIgG") or an anti-FAM19A5 ("G4") antibody against healthy animals ("naive").
Figure 3B:
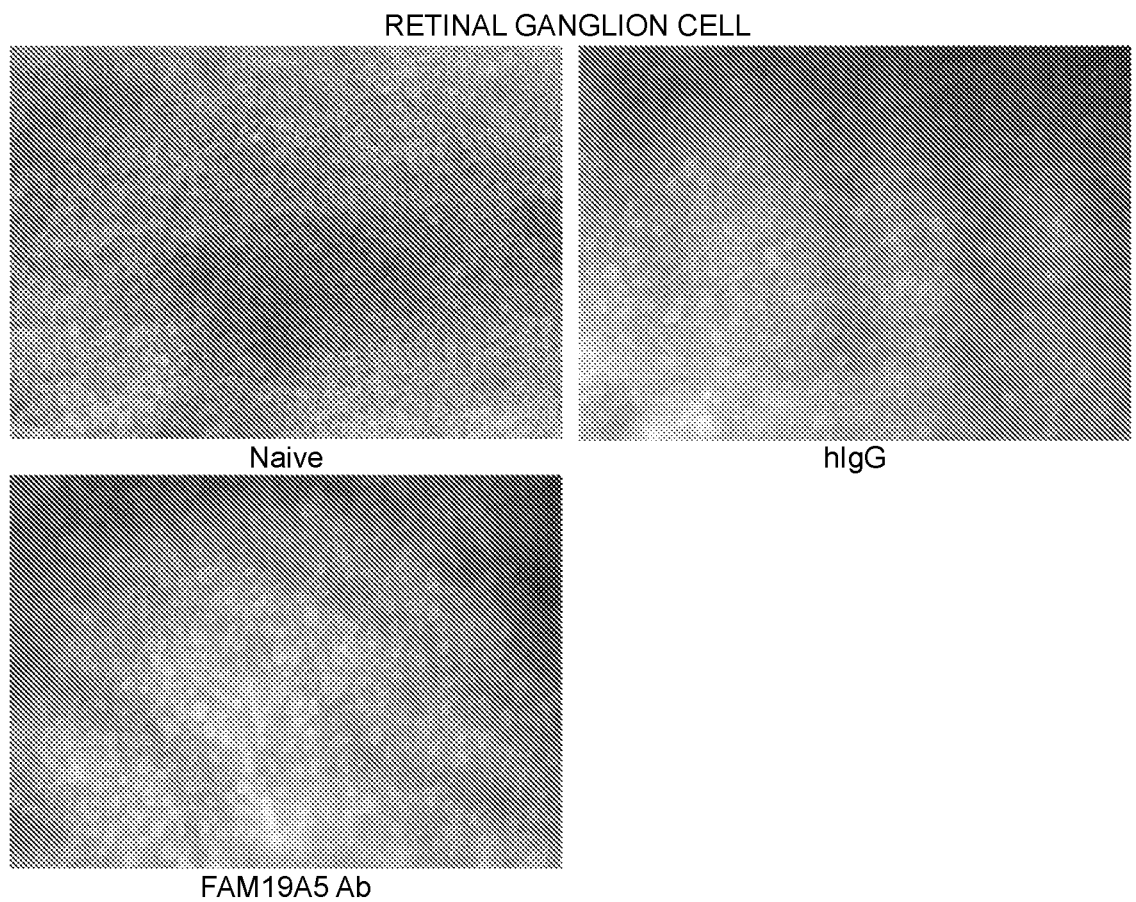

As shown in FIGS. 3A and 3B, the number of retinal ganglion cells in the glaucoma-induced rabbits that received the IgG control antibody was significantly lower than that of the naïve control rabbits (both in absolute number and percentage of total cells in the retinal ganglion cell layer). However, in animals that received the anti-FAM19A5 antibody, there was a marked increase in the number of retinal ganglion cells observed in the retinal ganglion cell layer. Such results suggest that the administration of the anti-FAM19A5 antibody can reduce the loss of retinal ganglion cell observed with glaucoma and protect the nerve connections of the inner plexiform layer and the retinal nerve cells.

Example 9

Anti-Inflammatory Effects of In Vivo Administration of Anti-FAM19A5 Antibody

While the exact causes of glaucoma have yet to be fully elucidated, animals studies have shown a strong link between inflammation and the structural damages associated with glaucoma (e.g., loss of retinal ganglion cells). Tezel et al., *Invest Ophthalmol Vis Sci* 42: 1787-1794 (2001); Wang et al., *Invest Ophthalmol Vis Sci* 49: 1916-1923 (2008).

To assess whether the increased retinal ganglion cell frequency observed in Example 3 is due to anti-inflammatory properties of anti-FAM19A5 antibody, glaucoma was induced in New Zealand White rabbits as described in the above Examples. At about 2 weeks post glaucoma induction, the animals received either human IgG (control) or FAM19A5-specific antibodies 100 μg in each eye via intravitreal injection. The animals received the antibodies once a week for a total of four weeks. After the last antibody administration, the rabbits were sacrificed and the eyes were excised and fixed in 4% paraformaldehyde (pH 7.4). The eyes were embedded in OCT cryostat sectioning medium and stored at −80° C. until ready for sectioning. When ready, the eyes were cut in to 5 μm thick sections, which were then mounted onto glass slides for staining.

The anti-inflammatory properties of the anti-FAM19A5 antibody were assessed by staining for Iba-1, which is a calcium-binding protein that is specifically expressed on microglia activation. Bosco et al., *J Comp Neurol* 519(4): 599-620 (2011). Briefly, after deparafiinization, the tissue sections were blocked with 10% normal horse serum (Vector laboratories, Cat #S-2000, Lot #ZC0621) for approximately 1 hour. Then, the tissue sections were stained overnight at 4° C. with the rabbit anti-Iba-1 antibody (Wako, Cat #019-19741, Lot #LKG5732) ("primary antibody") at 1:250 concentration in a buffer containing 0.1% triton X-100 and 3% normal horse serum ("dilution buffer"). The next morning, the tissue sections were washed and stained with biotinylated goat anti-rabbit IgG (Vector laboratories, Cat #BA-1000, Lot #ZB0318) at 1:500 concentration in the dilution buffer for approximately 1 hour. Afterwards, the tissue sections were washed and treated with avidin-biotin peroxidase complex solution (Vector laboratories, Cat #6200) for an additional 1 hour. Next, the tissue sections were washed and treated with the DAB substrate solution (1 drop of DAB chromogen to every 1 mL of DAB buffer) (Vector laboratories, Cat #SK-4100, Lot #ZC1214). Once the desired color intensity was achieved (approximately 1 minutes), the tissue sections were washed and analyzed under a bright-field light microscope.

Figure 4:
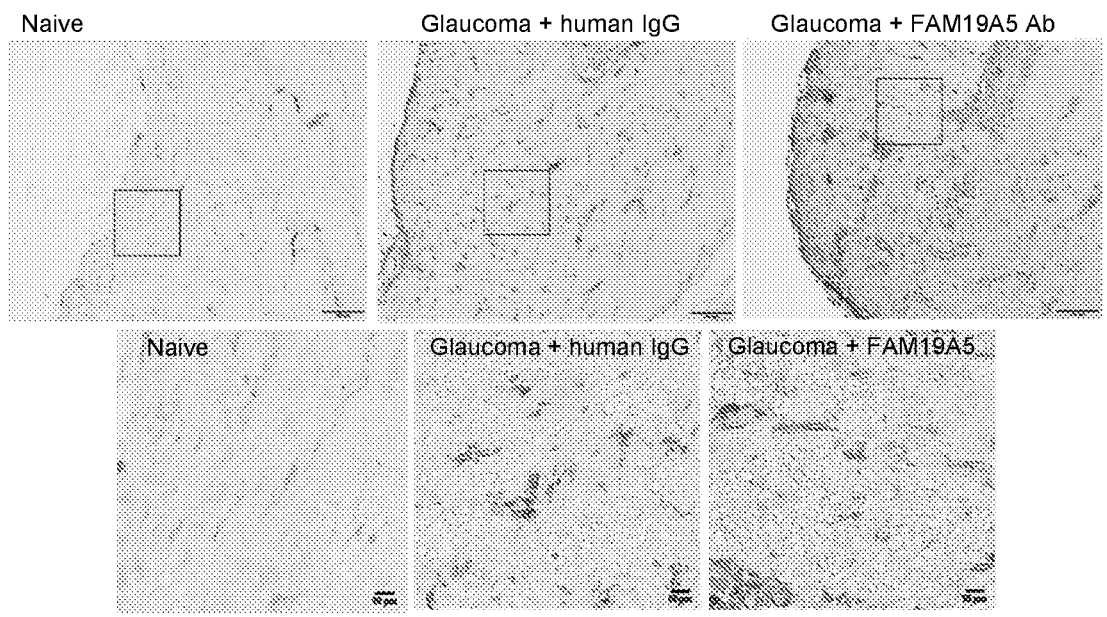
FIG. 4 shows the anti-inflammatory effects of FAM19A5 antibody treatment in a rabbit model of glaucoma induced by cauterization of the episcleral veins. As a marker for inflammation, at day 28 post glaucoma induction (i.e., animals received a total of 4 antibody administration at a weekly interval), Iba-1 expression was assessed in the eyes of glaucoma-induced rabbits treated with FAM19A5 antibody ("Glaucoma+FAM19A5 Ab"), human IgG1 control antibody ("Glaucoma+human IgG"), or no treatment at all ("Naïve") (i.e., healthy animal controls). The upper panels show representative immunohistochemical images from each of the groups. The lower panels show the boxed region from the upper panels at a higher magnification.

As shown in FIG. 4, compared to the naïve animals, the glaucoma induced animals (both the IgG control group and the anti-FAM19A5 antibody group) expressed significantly higher level of Iba-1 expression within the optic nerve head region. However, as between the two antibody treated groups, the FAM19A5 antibody treated animals had significantly less Iba-1 positive staining than those animals that received the IgG control antibody. This result suggests that the FAM19A5 antibody treats glaucoma by suppressing the inflammation-mediated activation of microglia within the optic nerve head.

It is to be appreciated that the Detailed Description section, and not the Summary and Abstract sections, is intended to be used to interpret the claims. The Summary and Abstract sections can set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

This PCT application claims the priority benefit of U.S. Provisional Application Nos. 62/525,639, filed Jun. 27, 2017, and 62/582,889, filed Nov. 7, 2017, both of which are incorporated herein by reference in their entireties.

What is claimed is:

1. A method for treating a glaucoma in a subject in need thereof comprising administering to the subject an antibody, or an antigen-binding portion thereof, that specifically binds to a family with sequence similarity 19, member A5 ("FAM19A5") protein ("anti-FAM19A5 antibody"), wherein the anti-FAM19A5 antibody comprises a heavy chain CDR1, CDR2, and CDR3, and a light chain CDR1, CDR2, and CDR3, and wherein:
   (i) the heavy chain CDR1, CDR2, and CDR3 comprises the amino acid sequences set forth in SEQ ID NOs: 11, 12, and 13, respectively, and the light chain CDR1, CDR2, and CDR3 comprises the amino acid sequences set forth in SEQ ID NOs: 23, 24, and 25, respectively;
   (ii) the heavy chain CDR1, CDR2, and CDR3 comprises the amino acid sequences set forth in SEQ ID NOs: 14, 15, and 16, respectively, and the light chain CDR1, CDR2, and CDR3 comprises the amino acid sequences set forth in SEQ ID NOs: 26, 27, and 28, respectively;
   (iii) the heavy chain CDR1, CDR2, and CDR3 comprises the amino acid sequences set forth in SEQ ID NOs: 17, 18, and 19, respectively, and the light chain CDR1, CDR2, and CDR3 comprises the amino acid sequences set forth in SEQ ID NOs: 29, 30, and 31, respectively; or
   (iv) the heavy chain CDR1, CDR2, and CDR3 comprises the amino acid sequences set forth in SEQ ID NOs: 20, 21, and 22, respectively, and the light chain CDR1, CDR2, and CDR3 comprises the amino acid sequences set forth in SEQ ID NOs: 32, 33, and 34, respectively.

2. A method for reducing, ameliorating, or inhibiting inflammation associated with a glaucoma in a subject in need thereof comprising administering to the subject an antibody, or an antigen-binding portion thereof, that specifically binds to a family with sequence similarity 19, member A5 ("FAM19A5") protein ("anti-FAM19A5 antibody"), wherein the anti-FAM19A5 antibody comprises a heavy chain CDR1, CDR2, and CDR3, and a light chain CDR1, CDR2, and CDR3, and wherein:
   (i) the heavy chain CDR1, CDR2, and CDR3 comprises the amino acid sequences set forth in SEQ ID NOs: 11, 12, and 13, respectively, and the light chain CDR1, CDR2, and CDR3 comprises the amino acid sequences set forth in SEQ ID NOs: 23, 24, and 25, respectively;
   (ii) the heavy chain CDR1, CDR2, and CDR3 comprises the amino acid sequences set forth in SEQ ID NOs: 14, 15, and 16, respectively, and the light chain CDR1, CDR2, and CDR3 comprises the amino acid sequences set forth in SEQ ID NOs: 26, 27, and 28, respectively;
   (iii) the heavy chain CDR1, CDR2, and CDR3 comprises the amino acid sequences set forth in SEQ ID NOs: 17, 18, and 19, respectively, and the light chain CDR1, CDR2, and CDR3 comprises the amino acid sequences set forth in SEQ ID NOs: 29, 30, and 31, respectively; or
   (iv) the heavy chain CDR1, CDR2, and CDR3 comprises the amino acid sequences set forth in SEQ ID NOs: 20, 21, and 22, respectively, and the light chain CDR1, CDR2, and CDR3 comprises the amino acid sequences set forth in SEQ ID NOs: 32, 33, and 34, respectively.

3. The method of claim 1, wherein the glaucoma:
   (i) is selected from the group consisting of an open-angle glaucoma, angle-closure glaucoma, normal-tension glaucoma ("NTG"), congenital glaucoma, secondary glaucoma, pigmentary glaucoma, pseudoexfoliative glaucoma, traumatic glaucoma, neovascular glaucoma, irido corneal endothelial syndrome, and uveitic glaucoma;
   (ii) is associated with an optic nerve damage, retinal ganglion cell ("RGC") loss, high intraocular pressure ("TOP"), impaired blood-retina barrier, and/or increase in a level of microglia activity within a retina and/or optic nerve of the subject;
   (iii) is caused by a mechanical damage to an optic nerve head, increase in a level of inflammation within a retina, and/or optic nerve of the subject; or
   (iv) any combination thereof.

4. The method of claim 1, wherein the anti-FAM19A5 antibody is capable of: (i) delaying an onset of retinal nerve cell degeneration within the subject; (ii) reducing a level of inflammation within the retina and/or optic nerve of the subject; (iii) increasing a frequency of or reduces the loss of retinal ganglion cells or restores the number of retinal ganglion cells within a ganglion cell layer of the retina of the subject; or (iv) any combination thereof.

5. The method of claim 1, wherein the anti-FAM19A5 antibody is a chimeric antibody, or a humanized antibody.

6. The method of claim 1, wherein the anti-FAM19A5 antibody is administered intravitreally.

7. The method of claim 1, wherein the subject is a human.

8. The method of claim 1, wherein the anti-FAM19A5 antibody comprises a heavy chain variable region (VH) and a light chain variable region (VL), and wherein:
   (i) the VH comprises the amino acid sequence set forth in SEQ ID NO: 35, and the VL comprises the amino acid sequence set forth in SEQ ID NO: 39;
   (ii) the VH comprises the amino acid sequence set forth in SEQ ID NO: 36, and the VL comprises the amino acid sequence set forth in SEQ ID NO: 40;
   (iii) the VH comprises the amino acid sequence set forth in SEQ ID NO: 37, and the VL comprises the amino acid sequence set forth in SEQ ID NO: 41; or
   (iv) the VH comprises the amino acid sequence set forth in SEQ ID NO: 38, and the VL comprises the amino acid sequence set forth in SEQ ID NO: 42.

9. The method of claim 2, wherein the glaucoma:
   (i) is selected from the group consisting of an open-angle glaucoma, angle-closure glaucoma, normal-tension glaucoma ("NTG"), congenital glaucoma, secondary glaucoma, pigmentary glaucoma, pseudoexfoliative glaucoma, traumatic glaucoma, neovascular glaucoma, irido corneal endothelial syndrome, and uveitic glaucoma;

(ii) is associated with an optic nerve damage, a retinal ganglion cell ("RGC") loss, a high intraocular pressure ("TOP"), an impaired blood-retina barrier, and/or an increase in a level of microglia activity within a retina and/or optic nerve of the subject;

(iii) is caused by a mechanical damage to an optic nerve head and/or an increase in a level of inflammation within a retina and/or an optic nerve of the subject; or (iv) any combination thereof.

10. The method of claim 2, wherein the anti-FAM19A5 antibody comprises a heavy chain variable region (VH) and a light chain variable region (VL), and wherein:

(i) the VH comprises the amino acid sequence set forth in SEQ ID NO: 35, and the VL comprises the amino acid sequence set forth in SEQ ID NO: 39;

(ii) the VH comprises the amino acid sequence set forth in SEQ ID NO: 36, and the VL comprises the amino acid sequence set forth in SEQ ID NO: 40;

(iii) the VH comprises the amino acid sequence set forth in SEQ ID NO: 37, and the VL comprises the amino acid sequence set forth in SEQ ID NO: 41; or (iv) the VH comprises the amino acid sequence set forth in SEQ ID NO: 38, and the VL comprises the amino acid sequence set forth in SEQ ID NO: 42.

11. The method of claim 2, wherein the anti-FAM19A5 antibody is a chimeric antibody, or a humanized antibody.

12. The method of claim 2, wherein the anti-FAM19A5 antibody is administered intravitreally.

13. The method of claim 2, wherein the subject is a human.

14. The method of claim 2, wherein the anti-FAM19A5 antibody is capable of: (i) delaying an onset of retinal nerve cell degeneration within the subject; (ii) reducing a level of inflammation within the retina and/or optic nerve of the subject; (iii) increasing a frequency of or reduces the loss of retinal ganglion cells or restores the number of retinal ganglion cells within a ganglion cell layer of the retina of the subject; or (iv) any combination thereof.

15. The method of claim 1, wherein the anti-FAM19A5 antibody is capable of specifically binding to one or more amino acids corresponding to amino acid residues 46 to 51 (DSSQPR) of SEQ ID NO: 2.

16. The method of claim 2, wherein the anti-FAM19A5 antibody is capable of specifically binding to one or more amino acids corresponding to amino acid residues 46 to 51 (DSSQPR) of SEQ ID NO: 2.

17. The method of claim 1, wherein the anti-FAM19A5 antibody comprise a Fab, Fab', F(ab')2, Fv, or single chain Fv (scFv).

18. The method of claim 2, wherein the anti-FAM19A5 antibody comprise a Fab, Fab', F(ab')2, Fv, or single chain Fv (scFv).

19. The method of claim 1, wherein the anti-FAM19A5 antibody is formulated with a pharmaceutically acceptable carrier.

20. The method of claim 2, wherein the anti-FAM19A5 antibody is formulated with a pharmaceutically acceptable carrier.

* * * * *

SEQUENCE LISTING

```
<160> NUMBER OF SEQ ID NOS: 201

<210> SEQ ID NO 1
<211> LENGTH: 132
<212> TYPE: PRT
<213> ORGANISM: Homo Sapiens
```

-continued

<400> SEQUENCE: 1

Met Ala Pro Ser Pro Arg Thr Gly Ser Arg Gln Asp Ala Thr Ala Leu
1               5                   10                  15

Pro Ser Met Ser Ser Thr Phe Trp Ala Phe Met Ile Leu Ala Ser Leu
            20                  25                  30

Leu Ile Ala Tyr Cys Ser Gln Leu Ala Ala Gly Thr Cys Glu Ile Val
        35                  40                  45

Thr Leu Asp Arg Asp Ser Ser Gln Pro Arg Arg Thr Ile Ala Arg Gln
    50                  55                  60

Thr Ala Arg Cys Ala Cys Arg Lys Gly Gln Ile Ala Gly Thr Thr Arg
65                  70                  75                  80

Ala Arg Pro Ala Cys Val Asp Ala Arg Ile Ile Lys Thr Lys Gln Trp
                85                  90                  95

Cys Asp Met Leu Pro Cys Leu Glu Gly Glu Gly Cys Asp Leu Leu Ile
            100                 105                 110

Asn Arg Ser Gly Trp Thr Cys Thr Gln Pro Gly Gly Arg Ile Lys Thr
            115                 120                 125

Thr Thr Val Ser
    130

<210> SEQ ID NO 2
<211> LENGTH: 125
<212> TYPE: PRT
<213> ORGANISM: Homo Sapiens

<400> SEQUENCE: 2

Met Gln Leu Leu Lys Ala Leu Trp Ala Leu Ala Gly Ala Ala Leu Cys
1               5                   10                  15

Cys Phe Leu Val Leu Val Ile His Ala Gln Phe Leu Lys Glu Gly Gln
            20                  25                  30

Leu Ala Ala Gly Thr Cys Glu Ile Val Thr Leu Asp Arg Asp Ser Ser
        35                  40                  45

Gln Pro Arg Arg Thr Ile Ala Arg Gln Thr Ala Arg Cys Ala Cys Arg
    50                  55                  60

Lys Gly Gln Ile Ala Gly Thr Thr Arg Ala Arg Pro Ala Cys Val Asp
65                  70                  75                  80

Ala Arg Ile Ile Lys Thr Lys Gln Trp Cys Asp Met Leu Pro Cys Leu
                85                  90                  95

Glu Gly Glu Gly Cys Asp Leu Leu Ile Asn Arg Ser Gly Trp Thr Cys
            100                 105                 110

Thr Gln Pro Gly Gly Arg Ile Lys Thr Thr Thr Val Ser
            115                 120                 125

<210> SEQ ID NO 3
<211> LENGTH: 53
<212> TYPE: PRT
<213> ORGANISM: Homo Sapiens

<400> SEQUENCE: 3

Met Tyr His His Arg Glu Trp Pro Ala Arg Ile Ile Lys Thr Lys Gln
1               5                   10                  15

Trp Cys Asp Met Leu Pro Cys Leu Glu Gly Glu Gly Cys Asp Leu Leu
            20                  25                  30

Ile Asn Arg Ser Gly Trp Thr Cys Thr Gln Pro Gly Gly Arg Ile Lys
            35                  40                  45

Thr Thr Thr Val Ser

<210> SEQ ID NO 4
<211> LENGTH: 1501
<212> TYPE: DNA
<213> ORGANISM: Homo Sapiens

<400> SEQUENCE: 4

| | | | | | |
|---|---|---|---|---|---|
| ggcggcggag | gatggcgcgc | gcggggcccg | cacgtggagg | ccggcgcggg | ggcgcgggca | 60 |
| gggccggctg | ctgagacgcg | ctgctgcccc | ccgcgcgggc | gccgcggctt | caatggcgcc | 120 |
| atcgcccagg | accggcagcc | ggcaagatgc | gaccgccctg | cccagcatgt | cctcaacttt | 180 |
| ctgggcgttc | atgatcctgg | ccagcctgct | catcgcctac | tgcagtcagc | tggccgccgg | 240 |
| cacctgtgag | attgtgacct | ggacccggga | cagcagccag | cctcggagga | cgatcgcccg | 300 |
| gcagaccgcc | cgctgtgcgt | gtagaaaggg | gcagatcgcc | ggcaccacga | gagcccggcc | 360 |
| cgcctgtgtg | gacgcaagaa | tcatcaagac | caagcagtgg | tgtgacatgc | ttccgtgtct | 420 |
| ggaggggaa | ggctgcgact | tgttaatcaa | ccggtcaggc | tggacgtgca | cgcagcccgg | 480 |
| cgggaggata | aagaccacca | cggtctcctg | acaaacacag | ccctgagggg | gccccggga | 540 |
| gtggccttgg | ctccctggag | agcccacgtc | tcagccacag | ttctccactc | gcctcggact | 600 |
| tcacccgttc | tctgccgccc | gcccactccg | tttccctgtg | gtccgtgaag | acggcctca | 660 |
| ggccttggca | tcctgagctt | cggtctgtcc | agccgacccg | aggaggccgg | actcagacac | 720 |
| ataggcgggg | ggcggcacct | ggcatcagca | atacgcagtc | tgtgggagcc | cggccgcgcc | 780 |
| cagccccgc | cgaccgtggc | gttggccctg | ctgtcctcag | aggaggagga | ggaggaggca | 840 |
| gctccggcag | ccacagaagg | ctgcagccca | gcccgcctga | cacgacgc | ctgccccagg | 900 |
| ggactgtcag | gcacagaagc | ggcctcctcc | cgtgccccag | actgtccgaa | ttgcttttat | 960 |
| tttcttatac | tttcagtata | ctccatagac | caaagagcaa | atctatctg | aacctggacg | 1020 |
| caccctcact | gtcagggtcc | ctggggtcgc | ttgtgcgggc | gggagggcaa | tggtggcaga | 1080 |
| gacatgctgg | tggccccggc | ggagcggaga | gggcggccgt | ggtggaggcc | tccaccccag | 1140 |
| gagcaccccg | cacaccctcg | gaggacgggc | ttcggctgcg | cggaggccgt | ggcacacctg | 1200 |
| cgggaggcag | cgacggcccc | cacgcagacg | ccgggaacgc | aggccgcttt | attcctctgt | 1260 |
| acttagatca | acttgaccgt | actaaaatcc | ctttctgttt | taaccagtta | acatgcctc | 1320 |
| ttctacagct | ccattttga | tagttggata | atccagtatc | tgccaagagc | atgttgggtc | 1380 |
| tcccgtgact | gctgcctcat | cgatacccca | tttagctcca | gaaagcaaag | aaaactcgag | 1440 |
| taacacttgt | ttgaaagaga | tcattaaatg | tattttgcaa | agcccaaaaa | aaaaaaaaaa | 1500 |
| a | | | | | | 1501 |

<210> SEQ ID NO 5
<211> LENGTH: 14
<212> TYPE: PRT
<213> ORGANISM: Artificial Sequence
<220> FEATURE:
<223> OTHER INFORMATION: Epitope F1

<400> SEQUENCE: 5

Gln Leu Ala Ala Gly Thr Cys Glu Ile Val Thr Leu Asp Arg
1               5                   10

<210> SEQ ID NO 6
<211> LENGTH: 20
<212> TYPE: PRT

```
<213> ORGANISM: Artificial Sequence
<220> FEATURE:
<223> OTHER INFORMATION: Epitope F2

<400> SEQUENCE: 6

Thr Leu Asp Arg Asp Ser Ser Gln Pro Arg Arg Thr Ile Ala Arg Gln
1               5                   10                  15

Thr Ala Arg Cys
            20

<210> SEQ ID NO 7
<211> LENGTH: 20
<212> TYPE: PRT
<213> ORGANISM: Artificial Sequence
<220> FEATURE:
<223> OTHER INFORMATION: Epitope F3

<400> SEQUENCE: 7

Thr Ala Arg Cys Ala Cys Arg Lys Gly Gln Ile Ala Gly Thr Thr Arg
1               5                   10                  15

Ala Arg Pro Ala
            20

<210> SEQ ID NO 8
<211> LENGTH: 20
<212> TYPE: PRT
<213> ORGANISM: Artificial Sequence
<220> FEATURE:
<223> OTHER INFORMATION: Epitope F4

<400> SEQUENCE: 8

Ala Arg Pro Ala Cys Val Asp Ala Arg Ile Ile Lys Thr Lys Gln Trp
1               5                   10                  15

Cys Asp Met Leu
            20

<210> SEQ ID NO 9
<211> LENGTH: 20
<212> TYPE: PRT
<213> ORGANISM: Artificial Sequence
<220> FEATURE:
<223> OTHER INFORMATION: Epitope F5

<400> SEQUENCE: 9

Cys Asp Met Leu Pro Cys Leu Glu Gly Glu Gly Cys Asp Leu Leu Ile
1               5                   10                  15

Asn Arg Ser Gly
            20

<210> SEQ ID NO 10
<211> LENGTH: 20
<212> TYPE: PRT
<213> ORGANISM: Artificial Sequence
<220> FEATURE:
<223> OTHER INFORMATION: Epitope F6

<400> SEQUENCE: 10

Asn Arg Ser Gly Trp Thr Cys Thr Gln Pro Gly Gly Arg Ile Lys Thr
1               5                   10                  15

Thr Thr Val Ser
            20

<210> SEQ ID NO 11
<211> LENGTH: 5
```

```
<212> TYPE: PRT
<213> ORGANISM: Artificial Sequence
<220> FEATURE:
<223> OTHER INFORMATION: 2-13 Antibody VH-CDR1

<400> SEQUENCE: 11

Ser His Gly Met Phe
1               5

<210> SEQ ID NO 12
<211> LENGTH: 17
<212> TYPE: PRT
<213> ORGANISM: Artificial Sequence
<220> FEATURE:
<223> OTHER INFORMATION: 2-13 Antibody VH-CDR2

<400> SEQUENCE: 12

Glu Ile Thr Asn Asp Gly Ser Gly Thr Asn Tyr Gly Ser Ala Val Lys
1               5                   10                  15

Gly

<210> SEQ ID NO 13
<211> LENGTH: 20
<212> TYPE: PRT
<213> ORGANISM: Artificial Sequence
<220> FEATURE:
<223> OTHER INFORMATION: 2-13 Antibody VH-CDR3

<400> SEQUENCE: 13

Ser Thr Tyr Glu Cys Pro Gly Gly Phe Ser Cys Trp Gly Asp Thr Gly
1               5                   10                  15

Gln Ile Asp Ala
            20

<210> SEQ ID NO 14
<211> LENGTH: 5
<212> TYPE: PRT
<213> ORGANISM: Artificial Sequence
<220> FEATURE:
<223> OTHER INFORMATION: 3-2 Antibody VH-CDR1

<400> SEQUENCE: 14

Ser Phe Asn Met Phe
1               5

<210> SEQ ID NO 15
<211> LENGTH: 17
<212> TYPE: PRT
<213> ORGANISM: Artificial Sequence
<220> FEATURE:
<223> OTHER INFORMATION: 3-2 Antibody VH-CDR2

<400> SEQUENCE: 15

Gln Ile Ser Ser Ser Gly Ser Ser Thr Asn Tyr Ala Pro Ala Val Arg
1               5                   10                  15

Gly

<210> SEQ ID NO 16
<211> LENGTH: 22
<212> TYPE: PRT
<213> ORGANISM: Artificial Sequence
<220> FEATURE:
<223> OTHER INFORMATION: 3-2 Antibody VH-CDR3

<400> SEQUENCE: 16
```

-continued

```
Ser Ser Tyr Asp Cys Pro Tyr Gly His Cys Ser Ser Gly Val Asp Ser
1               5                   10                  15

Ala Gly Glu Ile Asp Ala
            20

<210> SEQ ID NO 17
<211> LENGTH: 5
<212> TYPE: PRT
<213> ORGANISM: Artificial Sequence
<220> FEATURE:
<223> OTHER INFORMATION: 1-65 Antibody VH-CDR1

<400> SEQUENCE: 17

Ser Tyr Gln Met Gly
1               5

<210> SEQ ID NO 18
<211> LENGTH: 10
<212> TYPE: PRT
<213> ORGANISM: Artificial Sequence
<220> FEATURE:
<223> OTHER INFORMATION: 1-65 Antibody VH-CDR2

<400> SEQUENCE: 18

Val Ile Asn Lys Ser Gly Ser Asp Thr Ser
1               5                   10

<210> SEQ ID NO 19
<211> LENGTH: 13
<212> TYPE: PRT
<213> ORGANISM: Artificial Sequence
<220> FEATURE:
<223> OTHER INFORMATION: 1-65 Antibody VH-CDR3

<400> SEQUENCE: 19

Gly Ser Ala Ser Tyr Ile Thr Ala Ala Thr Ile Asp Ala
1               5                   10

<210> SEQ ID NO 20
<211> LENGTH: 8
<212> TYPE: PRT
<213> ORGANISM: Artificial Sequence
<220> FEATURE:
<223> OTHER INFORMATION: 1-28 Antibody VH-CDR1

<400> SEQUENCE: 20

Gly Phe Asp Phe Ser Asp Tyr Gly
1               5

<210> SEQ ID NO 21
<211> LENGTH: 8
<212> TYPE: PRT
<213> ORGANISM: Artificial Sequence
<220> FEATURE:
<223> OTHER INFORMATION: 1-28 Antibody VH-CDR2

<400> SEQUENCE: 21

Ile Arg Ser Asp Gly Ser Asn Pro
1               5

<210> SEQ ID NO 22
<211> LENGTH: 29
<212> TYPE: PRT
<213> ORGANISM: Artificial Sequence
<220> FEATURE:
<223> OTHER INFORMATION: 1-28 Antibody VH-CDR3
```

<400> SEQUENCE: 22

Ala Lys Asp Gly Asn Gly Tyr Cys Ala Leu Asp Ala Tyr Arg Ser Gly
1               5                   10                  15

Gly Tyr Ser Cys Gly Val Tyr Pro Gly Ser Ile Asp Ala
            20                  25

<210> SEQ ID NO 23
<211> LENGTH: 8
<212> TYPE: PRT
<213> ORGANISM: Artificial Sequence
<220> FEATURE:
<223> OTHER INFORMATION: 2-13 Antibody VL-CDR1

<400> SEQUENCE: 23

Ser Gly Gly Ser Tyr Ser Tyr Gly
1               5

<210> SEQ ID NO 24
<211> LENGTH: 7
<212> TYPE: PRT
<213> ORGANISM: Artificial Sequence
<220> FEATURE:
<223> OTHER INFORMATION: 2-13 Antibody VL-CDR2

<400> SEQUENCE: 24

Trp Asp Asp Glu Arg Pro Ser
1               5

<210> SEQ ID NO 25
<211> LENGTH: 11
<212> TYPE: PRT
<213> ORGANISM: Artificial Sequence
<220> FEATURE:
<223> OTHER INFORMATION: 2-13 Antibody VL-CDR3

<400> SEQUENCE: 25

Gly Thr Glu Asp Ile Ser Gly Thr Ala Gly Val
1               5                   10

<210> SEQ ID NO 26
<211> LENGTH: 13
<212> TYPE: PRT
<213> ORGANISM: Artificial Sequence
<220> FEATURE:
<223> OTHER INFORMATION: 3-2 Antibody VL-CDR1

<400> SEQUENCE: 26

Ser Gly Gly Gly Ser Tyr Ala Gly Ser Tyr Tyr Tyr Gly
1               5                   10

<210> SEQ ID NO 27
<211> LENGTH: 7
<212> TYPE: PRT
<213> ORGANISM: Artificial Sequence
<220> FEATURE:
<223> OTHER INFORMATION: 3-2 Antibody VL-CDR2

<400> SEQUENCE: 27

Glu Ser Asn Lys Arg Pro Ser
1               5

<210> SEQ ID NO 28
<211> LENGTH: 10
<212> TYPE: PRT
<213> ORGANISM: Artificial Sequence
<220> FEATURE:

```
<223> OTHER INFORMATION: 3-2 Antibody VL-CDR3

<400> SEQUENCE: 28

Gly Ser Trp Asp Ser Ser Asn Gly Gly Ile
1               5                   10

<210> SEQ ID NO 29
<211> LENGTH: 11
<212> TYPE: PRT
<213> ORGANISM: Artificial Sequence
<220> FEATURE:
<223> OTHER INFORMATION: 1-65 Antibody VL-CDR1

<400> SEQUENCE: 29

Ser Gly Gly Gly Ser Ser Gly Tyr Gly Tyr Gly
1               5                   10

<210> SEQ ID NO 30
<211> LENGTH: 7
<212> TYPE: PRT
<213> ORGANISM: Artificial Sequence
<220> FEATURE:
<223> OTHER INFORMATION: 1-65 Antibody VL-CDR2

<400> SEQUENCE: 30

Trp Asn Asp Lys Arg Pro Ser
1               5

<210> SEQ ID NO 31
<211> LENGTH: 14
<212> TYPE: PRT
<213> ORGANISM: Artificial Sequence
<220> FEATURE:
<223> OTHER INFORMATION: 1-65 Antibody VL-CDR3

<400> SEQUENCE: 31

Gly Asn Asp Asp Tyr Ser Ser Asp Ser Gly Tyr Val Gly Val
1               5                   10

<210> SEQ ID NO 32
<211> LENGTH: 5
<212> TYPE: PRT
<213> ORGANISM: Artificial Sequence
<220> FEATURE:
<223> OTHER INFORMATION: 1-28 Antibody VL-CDR1

<400> SEQUENCE: 32

Gly Tyr Gly Tyr Gly
1               5

<210> SEQ ID NO 33
<211> LENGTH: 3
<212> TYPE: PRT
<213> ORGANISM: Artificial Sequence
<220> FEATURE:
<223> OTHER INFORMATION: 1-28 Antibody VL-CDR2

<400> SEQUENCE: 33

Gln Asn Asp
1

<210> SEQ ID NO 34
<211> LENGTH: 11
<212> TYPE: PRT
<213> ORGANISM: Artificial Sequence
<220> FEATURE:
<223> OTHER INFORMATION: 1-28 Antibody VL-CDR3
```

<400> SEQUENCE: 34

Gly Ser Glu Asp Ser Ser Thr Leu Ala Gly Ile
1               5                   10

<210> SEQ ID NO 35
<211> LENGTH: 129
<212> TYPE: PRT
<213> ORGANISM: Artificial Sequence
<220> FEATURE:
<223> OTHER INFORMATION: 2-13 Antibody VH

<400> SEQUENCE: 35

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser His
            20                  25                  30

Gly Met Phe Trp Val Arg Gln Thr Pro Gly Lys Gly Leu Glu Tyr Val
        35                  40                  45

Ala Glu Ile Thr Asn Asp Gly Ser Gly Thr Asn Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Arg Ser Thr Tyr Glu Cys Pro Gly Gly Phe Ser Cys Trp Gly Asp
            100                 105                 110

Thr Gly Gln Ile Asp Ala Trp Gly His Gly Thr Glu Val Ile Val Ser
        115                 120                 125

Ser

<210> SEQ ID NO 36
<211> LENGTH: 131
<212> TYPE: PRT
<213> ORGANISM: Artificial Sequence
<220> FEATURE:
<223> OTHER INFORMATION: 3-2 Antibody VH

<400> SEQUENCE: 36

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
        35                  40                  45

Ala Gln Ile Ser Ser Ser Gly Ser Ser Thr Asn Tyr Ala Pro Ala Val
    50                  55                  60

Arg Gly Arg Ala Thr Ile Ser Arg Asp Asn Gly Gln Ser Thr Val Arg
65                  70                  75                  80

Leu Gln Leu Asn Asn Pro Gly Ala Glu Asp Thr Gly Thr Tyr Tyr Cys
                85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
        115                 120                 125

Val Ser Ser
        130

```
<210> SEQ ID NO 37
<211> LENGTH: 122
<212> TYPE: PRT
<213> ORGANISM: Artificial Sequence
<220> FEATURE:
<223> OTHER INFORMATION: 1-65 Antibody VH

<400> SEQUENCE: 37

Ala Val Thr Leu Asp Glu Ser Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Gly Val Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Gly Ser Ala Ser Tyr Ile Thr Ala Ala Thr Ile Asp Ala Trp
            100                 105                 110

Gly His Gly Thr Glu Val Ile Val Ser Ser
        115                 120

<210> SEQ ID NO 38
<211> LENGTH: 136
<212> TYPE: PRT
<213> ORGANISM: Artificial Sequence
<220> FEATURE:
<223> OTHER INFORMATION: 1-28 Antibody VH

<400> SEQUENCE: 38

Ala Val Thr Leu Asp Glu Ser Gly Gly Leu Gln Thr Pro Gly Gly
1               5                   10                  15

Ala Leu Ser Leu Val Cys Lys Ala Ser Gly Phe Asp Phe Ser Asp Tyr
            20                  25                  30

Gly Met Gly Trp Val Arg Gln Ala Pro Gly Lys Gly Leu Glu Trp Val
        35                  40                  45

Ala Ala Ile Arg Ser Asp Gly Ser Asn Pro Ser Tyr Gly Ser Ala Val
    50                  55                  60

Lys Gly Arg Ala Thr Ile Ser Lys Asp Asn Gly Arg Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Asp Gly Asn Gly Tyr Cys Ala Leu Asp Ala Tyr Arg Ser Gly
            100                 105                 110

Gly Tyr Ser Cys Gly Val Tyr Pro Gly Ser Ile Asp Ala Trp Gly His
        115                 120                 125

Gly Thr Glu Val Ile Val Ser Ser
        130                 135

<210> SEQ ID NO 39
<211> LENGTH: 104
<212> TYPE: PRT
<213> ORGANISM: Artificial Sequence
<220> FEATURE:
<223> OTHER INFORMATION: 2-13 Antibody VL
```

<400> SEQUENCE: 39

Ala Leu Thr Gln Pro Ser Ser Val Ser Ala Asn Pro Gly Glu Thr Val
1               5                   10                  15

Lys Ile Thr Cys Ser Gly Gly Ser Tyr Ser Tyr Gly Trp Phe Gln Gln
            20                  25                  30

Lys Ser Pro Gly Ser Ala Leu Val Thr Val Ile Tyr Trp Asp Asp Glu
        35                  40                  45

Arg Pro Ser Asp Ile Pro Ser Arg Phe Ser Gly Ala Leu Ser Gly Ser
    50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu
            100

<210> SEQ ID NO 40
<211> LENGTH: 108
<212> TYPE: PRT
<213> ORGANISM: Artificial Sequence
<220> FEATURE:
<223> OTHER INFORMATION: 3-2 Antibody VL

<400> SEQUENCE: 40

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45

Tyr Glu Ser Asn Lys Arg Pro Ser Asp Ile Pro Ser Arg Phe Ser Gly
    50                  55                  60

Ser Thr Ser Gly Ser Thr Ala Thr Leu Thr Ile Thr Gly Val Gln Ala
65                  70                  75                  80

Asp Asp Glu Ala Ile Tyr Tyr Cys Gly Ser Trp Asp Ser Ser Asn Gly
                85                  90                  95

Gly Ile Phe Gly Ala Gly Thr Thr Leu Thr Val Leu
            100                 105

<210> SEQ ID NO 41
<211> LENGTH: 110
<212> TYPE: PRT
<213> ORGANISM: Artificial Sequence
<220> FEATURE:
<223> OTHER INFORMATION: 1-65 Antibody VL

<400> SEQUENCE: 41

Ala Leu Thr Gln Pro Ser Ser Val Ser Ala Asn Pro Gly Glu Thr Val
1               5                   10                  15

Lys Ile Thr Cys Ser Gly Gly Gly Ser Ser Gly Tyr Gly Tyr Gly Trp
            20                  25                  30

Tyr Gln Gln Lys Ser Pro Ser Ala Pro Leu Thr Val Ile Tyr Trp
        35                  40                  45

Asn Asp Lys Arg Pro Ser Asp Ile Pro Ser Arg Phe Ser Gly Ser Lys
    50                  55                  60

Ser Gly Ser Thr His Thr Leu Thr Ile Thr Gly Val Gln Ala Glu Asp
65                  70                  75                  80

```
Glu Ala Val Tyr Phe Cys Gly Asn Asp Asp Tyr Ser Ser Asp Ser Gly
                85                  90                  95

Tyr Val Gly Val Phe Gly Ala Gly Thr Thr Leu Thr Val Leu
            100                 105                 110
```

<210> SEQ ID NO 42
<211> LENGTH: 104
<212> TYPE: PRT
<213> ORGANISM: Artificial Sequence
<220> FEATURE:
<223> OTHER INFORMATION: 1-28 Antibody VL

<400> SEQUENCE: 42

```
Ala Leu Thr Gln Pro Ser Ser Val Ser Ala Asn Leu Glu Gly Thr Val
1               5                   10                  15

Glu Ile Thr Cys Ser Gly Ser Gly Tyr Gly Tyr Gly Trp Tyr Gln Gln
                20                  25                  30

Lys Ser Pro Gly Ser Ala Pro Val Thr Val Ile Tyr Gln Asn Asp Lys
            35                  40                  45

Arg Pro Ser Asp Ile Pro Ser Arg Phe Ser Gly Ser Lys Ser Gly Ser
        50                  55                  60

Thr Gly Thr Leu Thr Ile Thr Gly Val Gln Val Glu Asp Glu Ala Val
65                  70                  75                  80

Tyr Tyr Cys Gly Ser Glu Asp Ser Ser Thr Leu Ala Gly Ile Phe Gly
                85                  90                  95

Ala Gly Thr Thr Leu Thr Val Leu
            100
```

<210> SEQ ID NO 43
<211> LENGTH: 388
<212> TYPE: DNA
<213> ORGANISM: Artificial Sequence
<220> FEATURE:
<223> OTHER INFORMATION: 2-13 Antibody VH

<400> SEQUENCE: 43

```
gccgtgacgt tggacgagtc cggggggcggc ctccagacgc ccggaggagc gctcagcctc      60
gtctgcaagg cctccggggtt caccttcagc agccatggca tgttctgggt gcgacagacg     120
cccggcaagg ggttggaata tgtcgctgaa attaccaatg atggtagtgg cacaaactac     180
gggtcggcgg tgaagggccg tgccaccatc tcgaggggaca acgggcagag cacagtgagg     240
ctgcagctga caacctcagg ggctgaggac accggcacct acttctgcgc cagatctact     300
tatgaatgtc ctggtggttt tagttgttgg ggtgatactg gtcaaataga cgcatggggc     360
cacgggaccg aagtcatcgt ctcctcca                                        388
```

<210> SEQ ID NO 44
<211> LENGTH: 394
<212> TYPE: DNA
<213> ORGANISM: Artificial Sequence
<220> FEATURE:
<223> OTHER INFORMATION: 3-2 Antibody VH

<400> SEQUENCE: 44

```
gccgtgacgt tggacgagtc cggggggcggc ctccagacgc ccggaggagc gctcagcctc      60
gtctgcaagg cctccggggtt caccttcagc agcttcaaca tgttctgggt gcgacaggcg     120
cccggcaagg ggctggaata cgtcgctcaa attagcagca gtggtagtag cacaaactac     180
gcacccgcgg tgaggggccg tgccaccatc tcgaggggaca acgggcagag cacagtgagg     240
```

```
ctgcagctga caaccccggg ggctgaagac accggcacct actactgcgc caaaagtagt    300
tatgactgtc cttacggtca ttgtagtagt ggtgttgata gtgctggtga gatcgacgca    360 tgggccacg ggaccgaagt catcgtctcc tcca                                 394
```

<210> SEQ ID NO 45
<211> LENGTH: 366
<212> TYPE: DNA
<213> ORGANISM: Artificial Sequence
<220> FEATURE:
<223> OTHER INFORMATION: 1-65 Antibody VH

<400> SEQUENCE: 45

```
gccgtgacgt tggacgagtc cggggcggc ctccagacgc ccggaggagc gctcagcctc     60
gtctgcaagg cctccgggtt caccttcagc agctatcaga tgggctgggt gcgacaggcg   120
cccggcaagg ggctggaatg ggtcggtgtt attaacaaga gtggtagtga cacatcatac   180
gggtcggcgg tgaagggccg tgccaccatc tcgaggaca acgggcagag cacagtgagg   240
ctgcagctga caacctcag ggctgaggac accggcacct acttctgcgc caaaggttct    300
gctagttata taactgctgc taccatcgac gcatggggcc acgggaccga agtcatcgtc   360
tcctcc                                                              366
```

<210> SEQ ID NO 46
<211> LENGTH: 408
<212> TYPE: DNA
<213> ORGANISM: Artificial Sequence
<220> FEATURE:
<223> OTHER INFORMATION: 1-28 Antibody VH

<400> SEQUENCE: 46

```
gccgtgacgt tggacgagtc cggggcggc ctccagacgc ccggaggagc gctcagcctc     60
gtctgcaagg cctccgggtt cgacttcagc gattatggca tgggttgggt gcgacaggct   120
ccaggcaagg ggctggagtg ggttgctgct attagaagtg atggtagtaa cccatcatac   180
gggtcggcgg tgaagggccg tgccaccatc tcgaaggaca acgggcgaag cacagtgagg   240
ctgcagctga caacctcag ggctgaggac accgccacct actactgcgc caaggatggt    300
aatggttact gtgctctcga tgcttatcgt agtggtggtt atagttgtgg tgtttatcct   360
ggtagcatcg acgcatgggg ccacgggacc gaagtcatcg tctcctcc                408
```

<210> SEQ ID NO 47
<211> LENGTH: 315
<212> TYPE: DNA
<213> ORGANISM: Artificial Sequence
<220> FEATURE:
<223> OTHER INFORMATION: 2-13 Antibody VL

<400> SEQUENCE: 47

```
ggccctgact cagccgtcct cggtgtcagc aaacccagga gaaaccgtca agataacctg     60 ctccggggt agctatagct atggctggtt ccagcagaag tcctcctggca gtgcccttgt    120 cactgtgatc tactgggatg atgagagacc ctcggacatc ccttcacgat tctccggtgc   180
cctatccggc tccacaaaca cattaaccat cactggggtc aagccgacg acgaggctgt    240 ctatttctgt gggactgaag acatcagcgg cactgctggt gtatttgggg ccgggacaac    300
cctgaccgtc ctggg                                                    315
```

<210> SEQ ID NO 48
<211> LENGTH: 327

<212> TYPE: DNA
<213> ORGANISM: Artificial Sequence
<220> FEATURE:
<223> OTHER INFORMATION: 3-2 Antibody VL

<400> SEQUENCE: 48

```
ggccctgact cagccgtcct cggtgtcagc aaacccagga gaaaccgtca agatcacctg      60
ctccgggggt ggcagctatg ctggaagtta ctattatggc tggtaccagc agaaggcacc     120
tggcagtgcc cctgtcactc tgatctatga agcaacaag agaccctcgg acatcccttc      180
acgattctcc ggttccacat ctggctccac agccacacta accatcactg ggtccaagc      240
cgatgacgag gctatctatt actgtgggag ctgggacagt agcaatggtg gtatatttgg     300
ggccgggaca accctgaccg tcctagg                                        327
```

<210> SEQ ID NO 49
<211> LENGTH: 331
<212> TYPE: DNA
<213> ORGANISM: Artificial Sequence
<220> FEATURE:
<223> OTHER INFORMATION: 1-65 Antibody VL

<400> SEQUENCE: 49

```
ggccctgact cagccgtcct cggtgtcagc aaaccctggg gaaactgtca agatcacctg      60
ctccgggggt ggtagcagtg ctatggttta tggctggtat cagcagaagt cacctagcag    120
tgcccctctc actgtgatct actggaacga caagagaccc tcggacatcc cttcacgatt    180
ctccggttcc aaatccggct ccacacacac attaaccatc actggggtcc aagccgagga    240
cgaggctgta tatttctgtg ggaatgatga ctacagcagt gatagtggat atgtcggtgt    300
atttggggcc gggacaaccc tgaccgtcct a                                  331
```

<210> SEQ ID NO 50
<211> LENGTH: 312
<212> TYPE: DNA
<213> ORGANISM: Artificial Sequence
<220> FEATURE:
<223> OTHER INFORMATION: 1-28 Antibody VL

<400> SEQUENCE: 50

```
gccctgactc agccgtcctc ggtgtcagca aacctggaag gaaccgtcga gatcacctgc      60
tccgggagtg gctatggtta tggctggtat cagcagaagt ctcctggcag tgcccctgtc    120
actgtgatct atcagaacga caagagaccc tcggacatcc cttcacgatt ctccggttcc    180
aaatccggct ccacgggcac attaaccatc actggggtcc aagtcgagga cgaggctgtc    240
tattactgtg ggagtgaaga cagcagcact cttgctggta tatttggggc cgggacaacc    300
ctgaccgtcc ta                                                       312
```

<210> SEQ ID NO 51
<211> LENGTH: 100
<212> TYPE: PRT
<213> ORGANISM: Artificial Sequence
<220> FEATURE:
<223> OTHER INFORMATION: M3 mutant

<400> SEQUENCE: 51

```
Gln Phe Leu Lys Glu Gly Gln Leu Ala Ala Gly Thr Cys Glu Ile Val
1               5                   10                  15

Thr Leu Asp Arg Asp Ser Ser Gln Pro Arg Ile Glu Glu Arg Ser Gln
            20                  25                  30
```

```
Thr Ala Arg Cys Ala Cys Arg Lys Gly Gln Ile Ala Gly Thr Thr Arg
            35                  40                  45

Ala Arg Pro Ala Cys Val Asp Ala Arg Ile Ile Lys Thr Lys Gln Trp
 50                  55                  60

Cys Asp Met Leu Pro Cys Leu Glu Gly Glu Gly Cys Asp Leu Leu Ile
 65                  70                  75                  80

Asn Arg Ser Gly Trp Thr Cys Thr Gln Pro Gly Gly Arg Ile Lys Thr
            85                  90                  95

Thr Thr Val Ser
            100

<210> SEQ ID NO 52
<211> LENGTH: 100
<212> TYPE: PRT
<213> ORGANISM: Artificial Sequence
<220> FEATURE:
<223> OTHER INFORMATION: M4 mutant

<400> SEQUENCE: 52

Gln Phe Leu Lys Glu Gly Gln Leu Ala Ala Gly Thr Cys Glu Ile Val
 1               5                  10                  15

Thr Leu Asp Arg Asp Ser Ser Gln Pro Arg Arg Thr Ile Ala Arg Gln
            20                  25                  30

Thr Val Lys Cys Ser Cys Phe Pro Gly Gln Ile Ala Gly Thr Thr Arg
            35                  40                  45

Ala Arg Pro Ala Cys Val Asp Ala Arg Ile Ile Lys Thr Lys Gln Trp
 50                  55                  60

Cys Asp Met Leu Pro Cys Leu Glu Gly Glu Gly Cys Asp Leu Leu Ile
 65                  70                  75                  80

Asn Arg Ser Gly Trp Thr Cys Thr Gln Pro Gly Gly Arg Ile Lys Thr
            85                  90                  95

Thr Thr Val Ser
            100

<210> SEQ ID NO 53
<211> LENGTH: 100
<212> TYPE: PRT
<213> ORGANISM: Artificial Sequence
<220> FEATURE:
<223> OTHER INFORMATION: M5 mutant

<400> SEQUENCE: 53

Gln Phe Leu Lys Glu Gly Gln Leu Ala Ala Gly Thr Cys Glu Ile Val
 1               5                  10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
            35                  40                  45

Asn Lys Pro Ser Cys Val Asp Ala Arg Ile Ile Lys Thr Lys Gln Trp
 50                  55                  60

Cys Asp Met Leu Pro Cys Leu Glu Gly Glu Gly Cys Asp Leu Leu Ile
 65                  70                  75                  80

Asn Arg Ser Gly Trp Thr Cys Thr Gln Pro Gly Gly Arg Ile Lys Thr
            85                  90                  95

Thr Thr Val Ser
            100

<210> SEQ ID NO 54
```

```
<211> LENGTH: 100
<212> TYPE: PRT
<213> ORGANISM: Artificial Sequence
<220> FEATURE:
<223> OTHER INFORMATION: M6 mutant

<400> SEQUENCE: 54

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Leu Gln Arg Trp Trp
    50                  55                  60

Cys Gln Met Glu Leu Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 55
<211> LENGTH: 100
<212> TYPE: PRT
<213> ORGANISM: Artificial Sequence
<220> FEATURE:
<223> OTHER INFORMATION: M7 mutant

<400> SEQUENCE: 55

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Glu Cys Lys Thr Leu Pro
65                  70                  75                  80

Asp Asn Ser Gly Trp Thr Cys Thr Gln Pro Gly Gly Arg Ile Lys Thr
                85                  90                  95

Thr Thr Val Ser
            100

<210> SEQ ID NO 56
<211> LENGTH: 101
<212> TYPE: PRT
<213> ORGANISM: Artificial Sequence
<220> FEATURE:
<223> OTHER INFORMATION: M8 mutant

<400> SEQUENCE: 56

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45
```

Ala Arg Pro Ala Cys Val Asp Ala Arg Ile Ile Lys Thr Lys Gln Trp
 50                  55                  60

Cys Asp Met Leu Pro Cys Leu Glu Gly Glu Gly Cys Asp Leu Leu Ile
 65                  70                  75                  80

Asn Arg Ser Gly Trp Thr Cys Ser Cys Ser Ser Gly Asn Lys Ile Lys
                 85                  90                  95

Thr Thr Thr Val Ser
            100

<210> SEQ ID NO 57
<211> LENGTH: 459
<212> TYPE: PRT
<213> ORGANISM: Artificial Sequence
<220> FEATURE:
<223> OTHER INFORMATION: 2-13 Antibody HC

<400> SEQUENCE: 57

Ala Val Thr Leu Asp Glu Ser Gly Gly Gly Leu Gln Thr Pro Gly Gly
 1               5                  10                  15

Ala Leu Ser Leu Val Cys Lys Ala Ser Gly Phe Thr Phe Ser Ser His
             20                  25                  30

Gly Met Phe Trp Val Arg Gln Thr Pro Gly Lys Gly Leu Glu Tyr Val
         35                  40                  45

Ala Glu Ile Thr Asn Asp Gly Ser Gly Thr Asn Tyr Gly Ser Ala Val
 50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Phe Cys
                 85                  90                  95

Ala Arg Ser Thr Tyr Glu Cys Pro Gly Gly Phe Ser Cys Trp Gly Asp
                100                 105                 110

Thr Gly Gln Ile Asp Ala Trp Gly His Gly Thr Glu Val Ile Val Ser
            115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
            325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
            355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
    450                 455

<210> SEQ ID NO 58
<211> LENGTH: 461
<212> TYPE: PRT
<213> ORGANISM: Artificial Sequence
<220> FEATURE:
<223> OTHER INFORMATION: 3-2 Antibody HC

<400> SEQUENCE: 58

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Phe Trp Val Arg Gln Ala Pro Gly Lys Gly Leu Glu Tyr Val
            35                  40                  45

Ala Gln Ile Ser Ser Ser Gly Ser Ser Thr Asn Tyr Ala Pro Ala Val
    50                  55                  60

Arg Gly Arg Ala Thr Ile Ser Arg Asp Asn Gly Gln Ser Thr Val Arg
65                  70                  75                  80

Leu Gln Leu Asn Asn Pro Gly Ala Glu Asp Thr Gly Thr Tyr Tyr Cys
            85                  90                  95

Ala Lys Ser Ser Tyr Asp Cys Pro Tyr Gly His Cys Ser Ser Gly Val
            100                 105                 110

Asp Ser Ala Gly Glu Ile Asp Ala Trp Gly His Gly Thr Glu Val Ile
            115                 120                 125

Val Ser Ser Ala Ser Thr Lys Gly Pro Ser Val Phe Pro Leu Ala Pro
130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
            165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
            195                 200                 205

```
Thr Gln Thr Tyr Ile Cys Asn Val Asn His Lys Pro Ser Asn Thr Lys
            210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
                275                 280                 285

Phe Asn Trp Tyr Val Asp Gly Val Glu Val His Asn Ala Lys Thr Lys
            290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
            450                 455                 460

<210> SEQ ID NO 59
<211> LENGTH: 452
<212> TYPE: PRT
<213> ORGANISM: Artificial Sequence
<220> FEATURE:
<223> OTHER INFORMATION: 1-65 Antibody HC

<400> SEQUENCE: 59

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Gly Val Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
                85                  90                  95

Ala Lys Gly Ser Ala Ser Tyr Ile Thr Ala Ala Thr Ile Asp Ala Trp
            100                 105                 110
```

```
Gly His Gly Thr Glu Val Ile Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 60
<211> LENGTH: 466
<212> TYPE: PRT
<213> ORGANISM: Artificial Sequence
<220> FEATURE:
<223> OTHER INFORMATION: 1-28 Antibody HC

<400> SEQUENCE: 60

Ala Val Thr Leu Asp Glu Ser Gly Gly Gly Leu Gln Thr Pro Gly Gly
1               5                   10                  15
```

-continued

```
Ala Leu Ser Leu Val Cys Lys Ala Ser Gly Phe Asp Phe Ser Asp Tyr
             20                  25                  30

Gly Met Gly Trp Val Arg Gln Ala Pro Gly Lys Gly Leu Glu Trp Val
         35                  40                  45

Ala Ala Ile Arg Ser Asp Gly Ser Asn Pro Ser Tyr Gly Ser Ala Val
     50                  55                  60

Lys Gly Arg Ala Thr Ile Ser Lys Asp Asn Gly Arg Ser Thr Val Arg
 65                  70                  75                  80

Leu Gln Leu Asn Asn Leu Arg Ala Glu Asp Thr Ala Thr Tyr Tyr Cys
                 85                  90                  95

Ala Lys Asp Gly Asn Gly Tyr Cys Ala Leu Asp Ala Tyr Arg Ser Gly
            100                 105                 110

Gly Tyr Ser Cys Gly Val Tyr Pro Gly Ser Ile Asp Ala Trp Gly His
            115                 120                 125

Gly Thr Glu Val Ile Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
```

```
                    435                 440                 445

Glu Ala Leu His Asn His Tyr Thr Gln Lys Ser Leu Ser Leu Ser Pro
    450                 455                 460

Gly Lys
465

<210> SEQ ID NO 61
<211> LENGTH: 211
<212> TYPE: PRT
<213> ORGANISM: Artificial Sequence
<220> FEATURE:
<223> OTHER INFORMATION: 2-13 Antibody LC

<400> SEQUENCE: 61

Ala Leu Thr Gln Pro Ser Ser Val Ser Ala Asn Pro Gly Glu Thr Val
1               5                   10                  15

Lys Ile Thr Cys Ser Gly Gly Ser Tyr Ser Tyr Gly Trp Phe Gln Gln
            20                  25                  30

Lys Ser Pro Gly Ser Ala Leu Val Thr Val Ile Tyr Trp Asp Asp Glu
        35                  40                  45

Arg Pro Ser Asp Ile Pro Ser Arg Phe Ser Gly Ala Leu Ser Gly Ser
    50                  55                  60

Thr Asn Thr Leu Thr Ile Thr Gly Val Gln Ala Asp Asp Glu Ala Val
65                  70                  75                  80

Tyr Phe Cys Gly Thr Glu Asp Ile Ser Gly Thr Ala Gly Val Phe Gly
                85                  90                  95

Ala Gly Thr Thr Leu Thr Val Leu Arg Ser Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 62
<211> LENGTH: 215
<212> TYPE: PRT
<213> ORGANISM: Artificial Sequence
<220> FEATURE:
<223> OTHER INFORMATION: 3-2 Antibody LC

<400> SEQUENCE: 62

Ala Leu Thr Gln Pro Ser Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Ala Pro Gly Ser Ala Pro Val Thr Leu Ile
        35                  40                  45
```

Tyr Glu Ser Asn Lys Arg Pro Ser Asp Ile Pro Ser Arg Phe Ser Gly
            50                  55                  60

Ser Thr Ser Gly Ser Thr Ala Thr Leu Thr Ile Thr Gly Val Gln Ala
 65                  70                  75                  80

Asp Asp Glu Ala Ile Tyr Tyr Cys Gly Ser Trp Asp Ser Ser Asn Gly
                    85                  90                  95

Gly Ile Phe Gly Ala Gly Thr Thr Leu Thr Val Leu Arg Ser Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
210                 215

<210> SEQ ID NO 63
<211> LENGTH: 217
<212> TYPE: PRT
<213> ORGANISM: Artificial Sequence
<220> FEATURE:
<223> OTHER INFORMATION: 1-65 Antibody LC

<400> SEQUENCE: 63

Ala Leu Thr Gln Pro Ser Ser Val Ser Ala Asn Pro Gly Glu Thr Val
1               5                   10                  15

Lys Ile Thr Cys Ser Gly Gly Ser Ser Gly Tyr Gly Tyr Gly Trp
                20                  25                  30

Tyr Gln Gln Lys Ser Pro Ser Ser Ala Pro Leu Thr Val Ile Tyr Trp
            35                  40                  45

Asn Asp Lys Arg Pro Ser Asp Ile Pro Ser Arg Phe Ser Gly Ser Lys
 50                  55                  60

Ser Gly Ser Thr His Thr Leu Thr Ile Thr Gly Val Gln Ala Glu Asp
 65                  70                  75                  80

Glu Ala Val Tyr Phe Cys Gly Asn Asp Asp Tyr Ser Ser Asp Ser Gly
                    85                  90                  95

Tyr Val Gly Val Phe Gly Ala Gly Thr Thr Leu Thr Val Leu Arg Ser
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 64
<211> LENGTH: 211
<212> TYPE: PRT
<213> ORGANISM: Artificial Sequence
<220> FEATURE:
<223> OTHER INFORMATION: 1-28 Antibody LC

<400> SEQUENCE: 64

Ala Leu Thr Gln Pro Ser Ser Val Ser Ala Asn Leu Glu Gly Thr Val
1               5                   10                  15

Glu Ile Thr Cys Ser Gly Ser Gly Tyr Gly Tyr Gly Trp Tyr Gln Gln
            20                  25                  30

Lys Ser Pro Gly Ser Ala Pro Val Thr Val Ile Tyr Gln Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Val Glu Asp Glu Ala Val
65                  70                  75                  80

Tyr Tyr Cys Gly Ser Glu Asp Ser Ser Thr Leu Ala Gly Ile Phe Gly
                85                  90                  95

Ala Gly Thr Thr Leu Thr Val Leu Arg Ser Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 65
<211> LENGTH: 5
<212> TYPE: PRT
<213> ORGANISM: Artificial Sequence
<220> FEATURE:
<223> OTHER INFORMATION: EP1 Epitope

<400> SEQUENCE: 65

Ile Val Thr Leu Asp
1               5

<210> SEQ ID NO 66
<211> LENGTH: 5
<212> TYPE: PRT
<213> ORGANISM: Artificial Sequence
<220> FEATURE:
<223> OTHER INFORMATION: EP2 Epitope

```
<400> SEQUENCE: 66

Asp Ser Ser Gln Pro
1               5

<210> SEQ ID NO 67
<211> LENGTH: 5
<212> TYPE: PRT
<213> ORGANISM: Artificial Sequence
<220> FEATURE:
<223> OTHER INFORMATION: EP3 Epitope

<400> SEQUENCE: 67

Arg Thr Ile Ala Arg
1               5

<210> SEQ ID NO 68
<211> LENGTH: 7
<212> TYPE: PRT
<213> ORGANISM: Artificial Sequence
<220> FEATURE:
<223> OTHER INFORMATION: EP4 Epitope

<400> SEQUENCE: 68

Ala Arg Cys Ala Cys Arg Lys
1               5

<210> SEQ ID NO 69
<211> LENGTH: 4
<212> TYPE: PRT
<213> ORGANISM: Artificial Sequence
<220> FEATURE:
<223> OTHER INFORMATION: EP5 Epitope

<400> SEQUENCE: 69

Ala Arg Pro Ala
1

<210> SEQ ID NO 70
<211> LENGTH: 9
<212> TYPE: PRT
<213> ORGANISM: Artificial Sequence
<220> FEATURE:
<223> OTHER INFORMATION: EP6 Epitope

<400> SEQUENCE: 70

Lys Thr Lys Gln Trp Cys Asp Met Leu
1               5

<210> SEQ ID NO 71
<211> LENGTH: 8
<212> TYPE: PRT
<213> ORGANISM: Artificial Sequence
<220> FEATURE:
<223> OTHER INFORMATION: EP7 Epitope

<400> SEQUENCE: 71

Gly Cys Asp Leu Leu Ile Asn Arg
1               5

<210> SEQ ID NO 72
<211> LENGTH: 8
<212> TYPE: PRT
<213> ORGANISM: Artificial Sequence
<220> FEATURE:
<223> OTHER INFORMATION: EP8 Epitope

<400> SEQUENCE: 72
```

```
Thr Cys Thr Gln Pro Gly Gly Arg
1               5

<210> SEQ ID NO 73
<211> LENGTH: 20
<212> TYPE: PRT
<213> ORGANISM: Artificial Sequence
<220> FEATURE:
<223> OTHER INFORMATION: F2-01-BSA (#1)

<400> SEQUENCE: 73

Thr Ala Asp Arg Asp Ser Ser Gln Pro Arg Arg Thr Ile Ala Arg Gln
1               5                   10                  15

Thr Ala Arg Cys
            20

<210> SEQ ID NO 74
<211> LENGTH: 20
<212> TYPE: PRT
<213> ORGANISM: Artificial Sequence
<220> FEATURE:
<223> OTHER INFORMATION: F2-02-BSA (#2)

<400> SEQUENCE: 74

Thr Leu Ala Arg Asp Ser Ser Gln Pro Arg Arg Thr Ile Ala Arg Gln
1               5                   10                  15

Thr Ala Arg Cys
            20

<210> SEQ ID NO 75
<211> LENGTH: 20
<212> TYPE: PRT
<213> ORGANISM: Artificial Sequence
<220> FEATURE:
<223> OTHER INFORMATION: F2-03-BSA (#3)

<400> SEQUENCE: 75

Thr Leu Asp Arg Ala Ser Ser Gln Pro Arg Arg Thr Ile Ala Arg Gln
1               5                   10                  15

Thr Ala Arg Cys
            20

<210> SEQ ID NO 76
<211> LENGTH: 20
<212> TYPE: PRT
<213> ORGANISM: Artificial Sequence
<220> FEATURE:
<223> OTHER INFORMATION: F2-04-BSA (#4)

<400> SEQUENCE: 76

Thr Leu Asp Arg Asp Ala Ser Gln Pro Arg Arg Thr Ile Ala Arg Gln
1               5                   10                  15

Thr Ala Arg Cys
            20

<210> SEQ ID NO 77
<211> LENGTH: 20
<212> TYPE: PRT
<213> ORGANISM: Artificial Sequence
<220> FEATURE:
<223> OTHER INFORMATION: F2-05-BSA (#5)

<400> SEQUENCE: 77

Thr Leu Asp Arg Asp Ser Ala Gln Pro Arg Arg Thr Ile Ala Arg Gln
```

```
1               5                   10                  15

Thr Ala Arg Cys
        20

<210> SEQ ID NO 78
<211> LENGTH: 20
<212> TYPE: PRT
<213> ORGANISM: Artificial Sequence
<220> FEATURE:
<223> OTHER INFORMATION: F2-06-BSA (#6)

<400> SEQUENCE: 78

Thr Leu Asp Arg Asp Ser Ser Ala Pro Arg Arg Thr Ile Ala Arg Gln
1               5                   10                  15

Thr Ala Arg Cys
        20

<210> SEQ ID NO 79
<211> LENGTH: 20
<212> TYPE: PRT
<213> ORGANISM: Artificial Sequence
<220> FEATURE:
<223> OTHER INFORMATION: F2-07-BSA (#7)

<400> SEQUENCE: 79

Thr Leu Asp Arg Asp Ser Ser Gln Ala Arg Arg Thr Ile Ala Arg Gln
1               5                   10                  15

Thr Ala Arg Cys
        20

<210> SEQ ID NO 80
<211> LENGTH: 20
<212> TYPE: PRT
<213> ORGANISM: Artificial Sequence
<220> FEATURE:
<223> OTHER INFORMATION: F2-08-BSA (#8)

<400> SEQUENCE: 80

Thr Leu Asp Arg Asp Ser Ser Gln Pro Arg Ala Thr Ile Ala Arg Gln
1               5                   10                  15

Thr Ala Arg Cys
        20

<210> SEQ ID NO 81
<211> LENGTH: 20
<212> TYPE: PRT
<213> ORGANISM: Artificial Sequence
<220> FEATURE:
<223> OTHER INFORMATION: F2-09-BSA (#9)

<400> SEQUENCE: 81

Thr Leu Asp Arg Asp Ser Ser Gln Pro Arg Arg Ala Ile Ala Arg Gln
1               5                   10                  15

Thr Ala Arg Cys
        20

<210> SEQ ID NO 82
<211> LENGTH: 20
<212> TYPE: PRT
<213> ORGANISM: Artificial Sequence
<220> FEATURE:
<223> OTHER INFORMATION: F2-10-BSA (#10)

<400> SEQUENCE: 82
```

```
Thr Leu Asp Arg Asp Ser Ser Gln Pro Arg Arg Thr Ala Ala Arg Gln
1               5                   10                  15

Thr Ala Arg Cys
            20

<210> SEQ ID NO 83
<211> LENGTH: 20
<212> TYPE: PRT
<213> ORGANISM: Artificial Sequence
<220> FEATURE:
<223> OTHER INFORMATION: F2-11-BSA (#11)

<400> SEQUENCE: 83

Thr Leu Asp Arg Asp Ser Ser Gln Pro Arg Arg Thr Ile Arg Arg Gln
1               5                   10                  15

Thr Ala Arg Cys
            20

<210> SEQ ID NO 84
<211> LENGTH: 20
<212> TYPE: PRT
<213> ORGANISM: Artificial Sequence
<220> FEATURE:
<223> OTHER INFORMATION: F2-12-BSA (#12)

<400> SEQUENCE: 84

Thr Leu Asp Arg Asp Ser Ser Gln Pro Arg Arg Thr Ile Ala Ala Gln
1               5                   10                  15

Thr Ala Arg Cys
            20

<210> SEQ ID NO 85
<211> LENGTH: 20
<212> TYPE: PRT
<213> ORGANISM: Artificial Sequence
<220> FEATURE:
<223> OTHER INFORMATION: F2-12-BSA (#13)

<400> SEQUENCE: 85

Thr Leu Asp Arg Asp Ser Ser Gln Pro Arg Arg Thr Ile Ala Arg Gln
1               5                   10                  15

Thr Val Arg Cys
            20

<210> SEQ ID NO 86
<211> LENGTH: 100
<212> TYPE: PRT
<213> ORGANISM: Artificial Sequence
<220> FEATURE:
<223> OTHER INFORMATION: Wild-type FAM19A5 Isoform 2 (without signal
      peptide)

<400> SEQUENCE: 86

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
                20                  25                  30

Thr Ala Arg Cys Ala Cys Arg Lys Gly Gln Ile Ala Gly Thr Thr Arg
            35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80
```

```
Asn Arg Ser Gly Trp Thr Cys Thr Gln Pro Gly Gly Arg Ile Lys Thr
                85                  90                  95

Thr Thr Val Ser
            100

<210> SEQ ID NO 87
<211> LENGTH: 100
<212> TYPE: PRT
<213> ORGANISM: Artificial Sequence
<220> FEATURE:
<223> OTHER INFORMATION: M1 mutant

<400> SEQUENCE: 87

Gln Phe Leu Lys Glu Gly Gln Leu Ala Ala Gly Thr Cys Glu Val Ile
1               5                   10                  15

Ala Ala His Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 88
<211> LENGTH: 100
<212> TYPE: PRT
<213> ORGANISM: Artificial Sequence
<220> FEATURE:
<223> OTHER INFORMATION: M2 mutant

<400> SEQUENCE: 88

Gln Phe Leu Lys Glu Gly Gln Leu Ala Ala Gly Thr Cys Glu Ile Val
1               5                   10                  15

Thr Leu Asp Arg Cys Cys Asn Lys Asn Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 89
<211> LENGTH: 5
<212> TYPE: PRT
<213> ORGANISM: Artificial Sequence
<220> FEATURE:
<223> OTHER INFORMATION: P2-C12 antibodyVH CDR1

<400> SEQUENCE: 89
```

```
Thr Tyr Ala Val Thr
1               5
```

<210> SEQ ID NO 90
<211> LENGTH: 16
<212> TYPE: PRT
<213> ORGANISM: Artificial Sequence
<220> FEATURE:
<223> OTHER INFORMATION: P2-C12antibodyVH CDR2

<400> SEQUENCE: 90

```
Tyr Ile Asn Trp Arg Gly Gly Thr Ser Tyr Ala Asn Trp Ala Lys Gly
1               5                   10                  15
```

<210> SEQ ID NO 91
<211> LENGTH: 15
<212> TYPE: PRT
<213> ORGANISM: Artificial Sequence
<220> FEATURE:
<223> OTHER INFORMATION: P2-C12antibodyVH CDR3

<400> SEQUENCE: 91

```
Asp Ala Ser Ser Gly Ala Ala Phe Gly Ser Tyr Gly Met Asp Pro
1               5                   10                  15
```

<210> SEQ ID NO 92
<211> LENGTH: 11
<212> TYPE: PRT
<213> ORGANISM: Artificial Sequence
<220> FEATURE:
<223> OTHER INFORMATION: P2-C12 antibodyVL CDR1

<400> SEQUENCE: 92

```
Gln Ala Ser Gln Ser Ile Ser Ser Tyr Leu Ser
1               5                   10
```

<210> SEQ ID NO 93
<211> LENGTH: 7
<212> TYPE: PRT
<213> ORGANISM: Artificial Sequence
<220> FEATURE:
<223> OTHER INFORMATION: P2-C12antibodyVL CDR2

<400> SEQUENCE: 93

```
Glu Ala Ser Lys Leu Ala Ser
1               5
```

<210> SEQ ID NO 94
<211> LENGTH: 12
<212> TYPE: PRT
<213> ORGANISM: Artificial Sequence
<220> FEATURE:
<223> OTHER INFORMATION: P2-C12antibodyVL CDR3

<400> SEQUENCE: 94

```
Gln Gln Gly Tyr Ser Ser Thr Asn Val Trp Asn Ala
1               5                   10
```

<210> SEQ ID NO 95
<211> LENGTH: 6
<212> TYPE: PRT
<213> ORGANISM: Artificial Sequence
<220> FEATURE:
<223> OTHER INFORMATION: 13B4antibodyVH CDR1

<400> SEQUENCE: 95

```
Ser Ser Asn Trp Trp Ser
```

```
<210> SEQ ID NO 96
<211> LENGTH: 16
<212> TYPE: PRT
<213> ORGANISM: Artificial Sequence
<220> FEATURE:
<223> OTHER INFORMATION: 13B4antibodyVH CDR2

<400> SEQUENCE: 96

Glu Ile Tyr His Gly Gly Thr Thr Asn Tyr Asn Pro Ser Leu Lys Gly
1               5                   10                  15

<210> SEQ ID NO 97
<211> LENGTH: 9
<212> TYPE: PRT
<213> ORGANISM: Artificial Sequence
<220> FEATURE:
<223> OTHER INFORMATION: 13B4antibodyVH CDR3

<400> SEQUENCE: 97

Trp Gln Leu Val Gly Gly Leu Asp Val
1               5

<210> SEQ ID NO 98
<211> LENGTH: 11
<212> TYPE: PRT
<213> ORGANISM: Artificial Sequence
<220> FEATURE:
<223> OTHER INFORMATION: 13B4antibodyVL CDR1

<400> SEQUENCE: 98

Ser Gly Asp Lys Leu Gly Asn Val Tyr Ala Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: 13B4antibodyVL CDR2

<400> SEQUENCE: 99

Gln Asp Asn Lys Arg Pro Ser
1               5

<210> SEQ ID NO 100
<211> LENGTH: 9
<212> TYPE: PRT
<213> ORGANISM: Artificial Sequence
<220> FEATURE:
<223> OTHER INFORMATION: 13B4antibodyVL CDR3

<400> SEQUENCE: 100

Gln Ala Trp Asp Ser Ser Thr Ala Val
1               5

<210> SEQ ID NO 101
<211> LENGTH: 5
<212> TYPE: PRT
<213> ORGANISM: Artificial Sequence
<220> FEATURE:
<223> OTHER INFORMATION: 13F7antibodyVH CDR1

<400> SEQUENCE: 101

Gly Tyr Ser Trp Thr
1               5
```

<210> SEQ ID NO 102
<211> LENGTH: 16
<212> TYPE: PRT
<213> ORGANISM: Artificial Sequence
<220> FEATURE:
<223> OTHER INFORMATION: 13F7antibodyVH CDR2

<400> SEQUENCE: 102

Glu Ile Ser His Phe Gly Ser Ala Asn Tyr Asn Pro Ser Leu Lys Ser
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: 13F7antibodyVH CDR3

<400> SEQUENCE: 103

Ala Leu Arg Gly Thr Tyr Ser Arg Phe Tyr Tyr Gly Met Asp Val
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: 13F7antibodyVL CDR1

<400> SEQUENCE: 104

Arg Ser Ser Gln Ser Leu Leu His Ser Asn Gly Tyr Asn Tyr Leu Asp
1               5                   10                  15

<210> SEQ ID NO 105
<211> LENGTH: 7
<212> TYPE: PRT
<213> ORGANISM: Artificial Sequence
<220> FEATURE:
<223> OTHER INFORMATION: 13F7antibodyVL CDR2

<400> SEQUENCE: 105

Leu Gly Ser Asn Arg Ala Ser
1               5

<210> SEQ ID NO 106
<211> LENGTH: 9
<212> TYPE: PRT
<213> ORGANISM: Artificial Sequence
<220> FEATURE:
<223> OTHER INFORMATION: 13F7antibodyVL CDR3

<400> SEQUENCE: 106

Met Gln Ala Arg Gln Thr Pro Leu Thr
1               5

<210> SEQ ID NO 107
<211> LENGTH: 5
<212> TYPE: PRT
<213> ORGANISM: Artificial Sequence
<220> FEATURE:
<223> OTHER INFORMATION: 15A9antibodyVH CDR1

<400> SEQUENCE: 107

Ser Tyr Tyr Trp Ser
1               5

<210> SEQ ID NO 108
<211> LENGTH: 16
<212> TYPE: PRT
<213> ORGANISM: Artificial Sequence
<220> FEATURE:
<223> OTHER INFORMATION: 15A9antibodyVH CDR2

<400> SEQUENCE: 108

Tyr Ile Tyr Pro Ser Gly Ser Thr Asn Tyr Asn Pro Ser Leu Lys Ser
1               5                   10                  15

<210> SEQ ID NO 109
<211> LENGTH: 12
<212> TYPE: PRT
<213> ORGANISM: Artificial Sequence
<220> FEATURE:
<223> OTHER INFORMATION: 15A9antibodyVH CDR3

<400> SEQUENCE: 109

Val Asn Pro Phe Gly Tyr Tyr Tyr Ala Met Asp Val
1               5                   10

<210> SEQ ID NO 110
<211> LENGTH: 11
<212> TYPE: PRT
<213> ORGANISM: Artificial Sequence
<220> FEATURE:
<223> OTHER INFORMATION: 15A9antibodyVL CDR1

<400> SEQUENCE: 110

Arg Ala Ser Gln Ser Ile Ser Thr Ser Leu Asn
1               5                   10

<210> SEQ ID NO 111
<211> LENGTH: 7
<212> TYPE: PRT
<213> ORGANISM: Artificial Sequence
<220> FEATURE:
<223> OTHER INFORMATION: 15A9antibodyVL CDR2

<400> SEQUENCE: 111

Gly Ala Ser Thr Leu Gln Ser
1               5

<210> SEQ ID NO 112
<211> LENGTH: 9
<212> TYPE: PRT
<213> ORGANISM: Artificial Sequence
<220> FEATURE:
<223> OTHER INFORMATION: 15A9antibodyVL CDR3

<400> SEQUENCE: 112

Gln Glu Ser Ala Ser Ile Pro Arg Thr
1               5

<210> SEQ ID NO 113
<211> LENGTH: 5
<212> TYPE: PRT
<213> ORGANISM: Artificial Sequence
<220> FEATURE:
<223> OTHER INFORMATION: P1-A03antibodyVH CDR1

<400> SEQUENCE: 113

Ser Asp Tyr Met Ser
1               5

```
<210> SEQ ID NO 114
<211> LENGTH: 16
<212> TYPE: PRT
<213> ORGANISM: Artificial Sequence
<220> FEATURE:
<223> OTHER INFORMATION: P1-A03antibodyVH CDR2

<400> SEQUENCE: 114

Ile Ile Tyr Pro Ser Thr Thr Thr Tyr Tyr Ala Ser Trp Ala Lys Gly
1               5                   10                  15

<210> SEQ ID NO 115
<211> LENGTH: 10
<212> TYPE: PRT
<213> ORGANISM: Artificial Sequence
<220> FEATURE:
<223> OTHER INFORMATION: P1-A03antibodyVH CDR3

<400> SEQUENCE: 115

Gly Ser Asn Trp Ser Ser Gly Met Asn Leu
1               5                   10

<210> SEQ ID NO 116
<211> LENGTH: 11
<212> TYPE: PRT
<213> ORGANISM: Artificial Sequence
<220> FEATURE:
<223> OTHER INFORMATION: P1-A03antibodyVL CDR1

<400> SEQUENCE: 116

Leu Ala Ser Glu Asp Ile Tyr Ser Gly Ile Ser
1               5                   10

<210> SEQ ID NO 117
<211> LENGTH: 7
<212> TYPE: PRT
<213> ORGANISM: Artificial Sequence
<220> FEATURE:
<223> OTHER INFORMATION: P1-A03antibodyVL CDR2

<400> SEQUENCE: 117

Gly Ala Ser Asn Leu Glu Ser
1               5

<210> SEQ ID NO 118
<211> LENGTH: 12
<212> TYPE: PRT
<213> ORGANISM: Artificial Sequence
<220> FEATURE:
<223> OTHER INFORMATION: P1-A03antibodyVL CDR3

<400> SEQUENCE: 118

Leu Gly Gly Tyr Ser Tyr Ser Ser Thr Gly Leu Thr
1               5                   10

<210> SEQ ID NO 119
<211> LENGTH: 5
<212> TYPE: PRT
<213> ORGANISM: Artificial Sequence
<220> FEATURE:
<223> OTHER INFORMATION: P1-A08antibodyVH CDR1

<400> SEQUENCE: 119

Thr Tyr Tyr Met Ser
1               5

<210> SEQ ID NO 120
```

```
<211> LENGTH: 16
<212> TYPE: PRT
<213> ORGANISM: Artificial Sequence
<220> FEATURE:
<223> OTHER INFORMATION: P1-A08antibodyVH CDR2

<400> SEQUENCE: 120

Ile Val Tyr Pro Ser Gly Thr Thr Tyr Tyr Ala Asn Trp Ala Lys Gly
1               5                   10                  15

<210> SEQ ID NO 121
<211> LENGTH: 8
<212> TYPE: PRT
<213> ORGANISM: Artificial Sequence
<220> FEATURE:
<223> OTHER INFORMATION: P1-A08antibodyVH CDR3

<400> SEQUENCE: 121

Gly Asp Ser Phe Gly Tyr Gly Leu
1               5

<210> SEQ ID NO 122
<211> LENGTH: 11
<212> TYPE: PRT
<213> ORGANISM: Artificial Sequence
<220> FEATURE:
<223> OTHER INFORMATION: P1-A08antibodyVL CDR1

<400> SEQUENCE: 122

Thr Ala Asp Thr Leu Ser Arg Ser Tyr Ala Ser
1               5                   10

<210> SEQ ID NO 123
<211> LENGTH: 7
<212> TYPE: PRT
<213> ORGANISM: Artificial Sequence
<220> FEATURE:
<223> OTHER INFORMATION: P1-A08antibodyVL CDR2

<400> SEQUENCE: 123

Arg Asp Thr Ser Arg Pro Ser
1               5

<210> SEQ ID NO 124
<211> LENGTH: 13
<212> TYPE: PRT
<213> ORGANISM: Artificial Sequence
<220> FEATURE:
<223> OTHER INFORMATION: P1-A08antibodyVL CDR3

<400> SEQUENCE: 124

Ala Thr Ser Asp Gly Ser Gly Ser Asn Tyr Gln Tyr Val
1               5                   10

<210> SEQ ID NO 125
<211> LENGTH: 5
<212> TYPE: PRT
<213> ORGANISM: Artificial Sequence
<220> FEATURE:
<223> OTHER INFORMATION: P1-F02antibodyVH CDR1

<400> SEQUENCE: 125

Asn Tyr Tyr Met Gly
1               5

<210> SEQ ID NO 126
<211> LENGTH: 16
```

<212> TYPE: PRT
<213> ORGANISM: Artificial Sequence
<220> FEATURE:
<223> OTHER INFORMATION: P1-F02antibodyVH CDR2

<400> SEQUENCE: 126

Ile Ile Tyr Ala Ser Gly Ser Thr Tyr Tyr Ala Ser Trp Ala Lys Gly
1               5                   10                  15

<210> SEQ ID NO 127
<211> LENGTH: 17
<212> TYPE: PRT
<213> ORGANISM: Artificial Sequence
<220> FEATURE:
<223> OTHER INFORMATION: P1-F02antibodyVH CDR3

<400> SEQUENCE: 127

Ile Asp Ile Gly Val Gly Asp Tyr Gly Trp Ala Tyr Asp Arg Leu Asp
1               5                   10                  15
Leu

<210> SEQ ID NO 128
<211> LENGTH: 11
<212> TYPE: PRT
<213> ORGANISM: Artificial Sequence
<220> FEATURE:
<223> OTHER INFORMATION: P1-F02antibodyVL CDR1

<400> SEQUENCE: 128

Leu Ala Ser Glu Asp Ile Tyr Ser Gly Ile Ser
1               5                   10

<210> SEQ ID NO 129
<211> LENGTH: 7
<212> TYPE: PRT
<213> ORGANISM: Artificial Sequence
<220> FEATURE:
<223> OTHER INFORMATION: P1-F02antibodyVL CDR2

<400> SEQUENCE: 129

Gly Ala Ser Asn Leu Glu Ser
1               5

<210> SEQ ID NO 130
<211> LENGTH: 10
<212> TYPE: PRT
<213> ORGANISM: Artificial Sequence
<220> FEATURE:
<223> OTHER INFORMATION: P1-F02antibodyVL CDR3

<400> SEQUENCE: 130

Leu Gly Gly Tyr Ser Tyr Ser Ser Ile Thr
1               5                   10

<210> SEQ ID NO 131
<211> LENGTH: 5
<212> TYPE: PRT
<213> ORGANISM: Artificial Sequence
<220> FEATURE:
<223> OTHER INFORMATION: P2-A01antibodyVH CDR1

<400> SEQUENCE: 131

Gly Tyr Tyr Met Ser
1               5

<210> SEQ ID NO 132

-continued

```
<211> LENGTH: 16
<212> TYPE: PRT
<213> ORGANISM: Artificial Sequence
<220> FEATURE:
<223> OTHER INFORMATION: P2-A01antibodyVH CDR2

<400> SEQUENCE: 132

Ile Ile Tyr Pro Ser Gly Ser Thr Asp Tyr Ala Ser Trp Ala Lys Gly
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: P2-A01antibodyVH CDR3

<400> SEQUENCE: 133

Val Ala Gly Tyr Val Gly Tyr Gly Tyr Glu Thr Phe Phe Asp Ile
1               5                   10                  15

<210> SEQ ID NO 134
<211> LENGTH: 11
<212> TYPE: PRT
<213> ORGANISM: Artificial Sequence
<220> FEATURE:
<223> OTHER INFORMATION: P2-A01antibodyVL CDR1

<400> SEQUENCE: 134

Leu Ala Ser Glu Asp Ile Tyr Ser Gly Ile Ser
1               5                   10

<210> SEQ ID NO 135
<211> LENGTH: 7
<212> TYPE: PRT
<213> ORGANISM: Artificial Sequence
<220> FEATURE:
<223> OTHER INFORMATION: P2-A01antibodyVL CDR2

<400> SEQUENCE: 135

Gly Ala Ser Asn Leu Glu Ser
1               5

<210> SEQ ID NO 136
<211> LENGTH: 14
<212> TYPE: PRT
<213> ORGANISM: Artificial Sequence
<220> FEATURE:
<223> OTHER INFORMATION: P2-A01antibodyVL CDR3

<400> SEQUENCE: 136

Leu Gly Gly Val Thr Tyr Ser Ser Thr Gly Thr His Leu Thr
1               5                   10

<210> SEQ ID NO 137
<211> LENGTH: 5
<212> TYPE: PRT
<213> ORGANISM: Artificial Sequence
<220> FEATURE:
<223> OTHER INFORMATION: P2-A03antibodyVH CDR1

<400> SEQUENCE: 137

Asn Tyr Asp Met Ser
1               5

<210> SEQ ID NO 138
<211> LENGTH: 16
```

```
<212> TYPE: PRT
<213> ORGANISM: Artificial Sequence
<220> FEATURE:
<223> OTHER INFORMATION: P2-A03antibodyVH CDR2

<400> SEQUENCE: 138

Phe Met Asp Thr Asp Gly Ser Ala Tyr Tyr Ala Thr Trp Ala Lys Gly
1               5                   10                  15

<210> SEQ ID NO 139
<211> LENGTH: 11
<212> TYPE: PRT
<213> ORGANISM: Artificial Sequence
<220> FEATURE:
<223> OTHER INFORMATION: P2-A03antibodyVH CDR3

<400> SEQUENCE: 139

Arg Gly Ser Ser Tyr Tyr Gly Gly Ile Asp Ile
1               5                   10

<210> SEQ ID NO 140
<211> LENGTH: 11
<212> TYPE: PRT
<213> ORGANISM: Artificial Sequence
<220> FEATURE:
<223> OTHER INFORMATION: P2-A03antibodyVL CDR1

<400> SEQUENCE: 140

Gln Ala Ser Gln Ser Ile Gly Gly Asn Leu Ala
1               5                   10

<210> SEQ ID NO 141
<211> LENGTH: 7
<212> TYPE: PRT
<213> ORGANISM: Artificial Sequence
<220> FEATURE:
<223> OTHER INFORMATION: P2-A03antibodyVL CDR2

<400> SEQUENCE: 141

Arg Ala Ser Thr Leu Ala Ser
1               5

<210> SEQ ID NO 142
<211> LENGTH: 14
<212> TYPE: PRT
<213> ORGANISM: Artificial Sequence
<220> FEATURE:
<223> OTHER INFORMATION: P2-A03antibodyVL CDR3

<400> SEQUENCE: 142

Gln Ser Pro Ala Tyr Asp Pro Ala Ala Tyr Val Gly Asn Ala
1               5                   10

<210> SEQ ID NO 143
<211> LENGTH: 5
<212> TYPE: PRT
<213> ORGANISM: Artificial Sequence
<220> FEATURE:
<223> OTHER INFORMATION: P2-F07antibodyVH CDR1

<400> SEQUENCE: 143

Ser Tyr Tyr Met Asn
1               5

<210> SEQ ID NO 144
<211> LENGTH: 16
<212> TYPE: PRT
```

<213> ORGANISM: Artificial Sequence
<220> FEATURE:
<223> OTHER INFORMATION: P2-F07antibodyVH CDR2

<400> SEQUENCE: 144

Ile Ile Tyr Pro Ser Gly Thr Thr Tyr Tyr Ala Gly Trp Ala Lys Gly
1               5                   10                  15

<210> SEQ ID NO 145
<211> LENGTH: 8
<212> TYPE: PRT
<213> ORGANISM: Artificial Sequence
<220> FEATURE:
<223> OTHER INFORMATION: P2-F07antibodyVH CDR3

<400> SEQUENCE: 145

Thr Val Ser Gly Tyr Phe Asp Ile
1               5

<210> SEQ ID NO 146
<211> LENGTH: 11
<212> TYPE: PRT
<213> ORGANISM: Artificial Sequence
<220> FEATURE:
<223> OTHER INFORMATION: P2-F07antibodyVL CDR1

<400> SEQUENCE: 146

Leu Ala Ser Glu Asp Ile Tyr Ser Ala Leu Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: P2-F07antibodyVL CDR2

<400> SEQUENCE: 147

Gly Thr Ser Asn Leu Glu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: P2-F07antibodyVL CDR3

<400> SEQUENCE: 148

Gln Gly Tyr Ser Ser Tyr Pro Leu Thr
1               5

<210> SEQ ID NO 149
<211> LENGTH: 5
<212> TYPE: PRT
<213> ORGANISM: Artificial Sequence
<220> FEATURE:
<223> OTHER INFORMATION: P2-F11antibodyVH CDR1

<400> SEQUENCE: 149

Ser Tyr Gly Val Ser
1               5

<210> SEQ ID NO 150
<211> LENGTH: 16
<212> TYPE: PRT
<213> ORGANISM: Artificial Sequence

```
<220> FEATURE:
<223> OTHER INFORMATION: P2-F11antibodyVH CDR2

<400> SEQUENCE: 150

Tyr Ile Ala Asn Asn Tyr Asn Pro His Tyr Ala Ser Trp Ala Lys Gly
1               5                   10                  15

<210> SEQ ID NO 151
<211> LENGTH: 7
<212> TYPE: PRT
<213> ORGANISM: Artificial Sequence
<220> FEATURE:
<223> OTHER INFORMATION: P2-F11antibodyVH CDR3

<400> SEQUENCE: 151

Asp Asn Tyr Gly Met Asp Pro
1               5

<210> SEQ ID NO 152
<211> LENGTH: 13
<212> TYPE: PRT
<213> ORGANISM: Artificial Sequence
<220> FEATURE:
<223> OTHER INFORMATION: P2-F11antibodyVL CDR1

<400> SEQUENCE: 152

Gln Ala Ser Gln Ser Val Tyr Asn Asn Lys Asn Leu Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: P2-F11antibodyVL CDR2

<400> SEQUENCE: 153

Ala Ala Ser Thr Leu Ala Ser
1               5

<210> SEQ ID NO 154
<211> LENGTH: 13
<212> TYPE: PRT
<213> ORGANISM: Artificial Sequence
<220> FEATURE:
<223> OTHER INFORMATION: P2-F11antibodyVL CDR3

<400> SEQUENCE: 154

Gln Gly Glu Phe Ser Cys Ser Ser Ala Asp Cys Asn Ala
1               5                   10

<210> SEQ ID NO 155
<211> LENGTH: 121
<212> TYPE: PRT
<213> ORGANISM: Artificial Sequence
<220> FEATURE:
<223> OTHER INFORMATION: P2-C12antibodyVH

<400> SEQUENCE: 155

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
        35                  40                  45
```

```
Tyr Ile Asn Trp Arg Gly Gly Thr Ser Tyr Ala Asn Trp Ala Lys Gly
        50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Asp
                85                  90                  95

Ala Ser Ser Gly Ala Ala Phe Gly Ser Tyr Gly Met Asp Pro Trp Gly
                100                 105                 110

Pro Gly Thr Leu Val Thr Val Ser Ser
        115                 120

<210> SEQ ID NO 156
<211> LENGTH: 118
<212> TYPE: PRT
<213> ORGANISM: Artificial Sequence
<220> FEATURE:
<223> OTHER INFORMATION: 13B4antibodyVH

<400> SEQUENCE: 156

Gln Val Gln Leu Gln Glu Ser Gly Pro Gly Leu Val Lys Pro Ser Gly
1               5                   10                  15

Thr Leu Ser Leu Asn Cys Ala Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Gly Gly Thr Thr Asn Tyr Asn Pro Ser Leu
        50                  55                  60

Lys Gly Arg Val Thr Met Ser Val Asp Lys Thr Lys Asn Gln Phe Ser
65                  70                  75                  80

Leu Arg Leu Ser Ser Val Thr Ala Val Asp Thr Ala Val Tyr Tyr Cys
                85                  90                  95

Ala Arg Trp Gln Leu Val Gly Gly Leu Asp Val Trp Gly Gln Gly Thr
                100                 105                 110

Thr Val Thr Val Ser Ser
            115

<210> SEQ ID NO 157
<211> LENGTH: 123
<212> TYPE: PRT
<213> ORGANISM: Artificial Sequence
<220> FEATURE:
<223> OTHER INFORMATION: 13F7antibodyVH

<400> SEQUENCE: 157

Gln Val Gln Leu Gln Glu Trp Gly Ala Gly Leu Leu Lys Pro Ser Glu
1               5                   10                  15

Thr Leu Ser Leu Thr Cys Ala Ile Asn Ala Glu Ser Phe Asn Gly Tyr
                20                  25                  30

Ser Trp Thr Trp Ile Arg Gln Thr Pro Gly Lys Gly Leu Glu Trp Ile
            35                  40                  45

Gly Glu Ile Ser His Phe Gly Ser Ala Asn Tyr Asn Pro Ser Leu Lys
        50                  55                  60

Ser Arg Ala Thr Ile Ser Ala Asp Lys Ser Lys Asn Gln Phe Ser Leu
65                  70                  75                  80

Lys Leu Thr Ser Val Thr Ala Val Asp Thr Ala Val Tyr Tyr Cys Ala
                85                  90                  95

Arg Ala Leu Arg Gly Thr Tyr Ser Arg Phe Tyr Tyr Gly Met Asp Val
                100                 105                 110
```

```
Trp Gly Gln Gly Thr Thr Val Thr Val Ser Ser
        115                 120

<210> SEQ ID NO 158
<211> LENGTH: 120
<212> TYPE: PRT
<213> ORGANISM: Artificial Sequence
<220> FEATURE:
<223> OTHER INFORMATION: 15A9antibodyVH

<400> SEQUENCE: 158

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Pro Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Lys Ser Val Thr Ala Val Asp Thr Ala Val Tyr Tyr Cys Ala
                85                  90                  95

Arg Val Asn Pro Phe Gly Tyr Tyr Tyr Ala Met Asp Val Trp Gly Gln
            100                 105                 110

Gly Thr Thr Val Thr Val Ser Ser
        115                 120

<210> SEQ ID NO 159
<211> LENGTH: 116
<212> TYPE: PRT
<213> ORGANISM: Artificial Sequence
<220> FEATURE:
<223> OTHER INFORMATION: P1-A03antibodyVH

<400> SEQUENCE: 159

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asp Tyr
            20                  25                  30

Met Ser Trp Val Arg Gln Ala Pro Gly Glu Gly Leu Glu Trp Ile Gly
        35                  40                  45

Ile Ile Tyr Pro Ser Thr Thr Thr Tyr Tyr Ala Ser Trp Ala Lys Gly
    50                  55                  60

Arg Phe Thr Ile Ser Lys Thr Ser Ser Thr Thr Val Glu Leu Lys Met
65                  70                  75                  80

Thr Ser Leu Thr Thr Glu Asp Thr Ala Thr Tyr Phe Cys Ala Arg Gly
                85                  90                  95

Ser Asn Trp Ser Ser Gly Met Asn Leu Trp Gly Pro Gly Thr Leu Val
            100                 105                 110

Thr Val Ser Ser
        115

<210> SEQ ID NO 160
<211> LENGTH: 113
<212> TYPE: PRT
<213> ORGANISM: Artificial Sequence
<220> FEATURE:
<223> OTHER INFORMATION: P1-A08antibodyVH
```

-continued

<400> SEQUENCE: 160

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ile Val Tyr Pro Ser Gly Thr Thr Tyr Tyr Ala Asn Trp Ala Lys Gly
    50                  55                  60

Arg Phe Thr Ile Ser Thr Ala Ser Thr Thr Val Asp Leu Met Ile Thr
65                  70                  75                  80

Ser Pro Thr Thr Glu Asp Thr Ala Thr Tyr Phe Cys Ala Arg Gly Asp
                85                  90                  95

Ser Phe Gly Tyr Gly Leu Trp Gly Pro Gly Thr Leu Val Thr Val Ser
                100                 105                 110

Ser

<210> SEQ ID NO 161
<211> LENGTH: 122
<212> TYPE: PRT
<213> ORGANISM: Artificial Sequence
<220> FEATURE:
<223> OTHER INFORMATION: P1-F02antibodyVH

<400> SEQUENCE: 161

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Gly Trp Val Arg Gln Ala Pro Gly Glu Gly Leu Glu Trp Ile Gly
        35                  40                  45

Ile Ile Tyr Ala Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Ile Asp
                85                  90                  95

Ile Gly Val Gly Asp Tyr Gly Trp Ala Tyr Asp Arg Leu Asp Leu Trp
                100                 105                 110

Gly Gln Gly Thr Leu Val Thr Val Ser Ser
        115                 120

<210> SEQ ID NO 162
<211> LENGTH: 121
<212> TYPE: PRT
<213> ORGANISM: Artificial Sequence
<220> FEATURE:
<223> OTHER INFORMATION: P2-A01antibodyVH

<400> SEQUENCE: 162

Gln Glu Gln Leu Val Glu Ser Gly Gly Arg Leu Val Thr Pro Gly Thr
1               5                   10                  15

Pro Leu Thr Leu Ser Cys Thr Ala Ser Gly Phe Phe Leu Ser Gly Tyr
            20                  25                  30

Tyr Met Ser Trp Val Arg Gln Ala Pro Gly Lys Gly Leu Glu Trp Ile
        35                  40                  45

```
Gly Ile Ile Tyr Pro Ser Gly Ser Thr Asp Tyr Ala Ser Trp Ala Lys
        50                  55                  60

Gly Arg Phe Thr Ile Ser Lys Thr Ser Thr Val Asp Leu Lys Ile
65                  70                  75                  80

Thr Thr Pro Thr Thr Glu Asp Thr Ala Thr Tyr Phe Cys Ala Arg Val
                    85                  90                  95

Ala Gly Tyr Val Gly Tyr Gly Tyr Glu Thr Phe Phe Asp Ile Trp Gly
                100                 105                 110

Pro Gly Thr Leu Val Thr Val Ser Leu
            115                 120

<210> SEQ ID NO 163
<211> LENGTH: 116
<212> TYPE: PRT
<213> ORGANISM: Artificial Sequence
<220> FEATURE:
<223> OTHER INFORMATION: P2-A03antibodyVH

<400> SEQUENCE: 163

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
                20                  25                  30

Met Ser Trp Val Arg Gln Ala Pro Gly Lys Gly Leu Glu Tyr Ile Gly
            35                  40                  45

Phe Met Asp Thr Asp Gly Ser Ala Tyr Tyr Ala Thr Trp Ala Lys Gly
        50                  55                  60

Arg Phe Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg Arg Gly
                85                  90                  95

Ser Ser Tyr Tyr Gly Gly Ile Asp Ile Trp Gly Pro Gly Thr Pro Val
                100                 105                 110

Thr Val Ser Leu
            115

<210> SEQ ID NO 164
<211> LENGTH: 113
<212> TYPE: PRT
<213> ORGANISM: Artificial Sequence
<220> FEATURE:
<223> OTHER INFORMATION: P2-F07antibodyVH

<400> SEQUENCE: 164

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
                20                  25                  30

Met Asn Trp Val Arg Gln Ala Pro Gly Lys Gly Leu Glu Trp Ile Gly
            35                  40                  45

Ile Ile Tyr Pro Ser Gly Thr Thr Tyr Tyr Ala Gly Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Ser Glu Asp Thr Ala Thr Tyr Phe Cys Ala Arg Thr Val
                85                  90                  95

Ser Gly Tyr Phe Asp Ile Trp Gly Pro Gly Thr Leu Val Thr Val Ser
                100                 105                 110
```

Leu

<210> SEQ ID NO 165
<211> LENGTH: 114
<212> TYPE: PRT
<213> ORGANISM: Artificial Sequence
<220> FEATURE:
<223> OTHER INFORMATION: P2-F11antibodyVH

<400> SEQUENCE: 165

```
Gln Glu Gln Leu Val Glu Ser Gly Gly Arg Leu Val Thr Pro Gly Thr
1               5                   10                  15

Thr Leu Thr Leu Thr Cys Thr Val Ser Gly Phe Ser Leu Ser Ser Tyr
            20                  25                  30

Gly Val Ser Trp Val Arg Gln Ala Pro Gly Lys Gly Leu Glu Trp Ile
        35                  40                  45

Gly Tyr Ile Ala Asn Asn Tyr Asn Pro His Tyr Ala Ser Trp Ala Lys
    50                  55                  60

Gly Arg Phe Thr Ile Ser Lys Thr Ser Ser Thr Val Asp Leu Lys
65                  70                  75                  80

Met Thr Ser Leu Thr Thr Glu Asp Thr Ala Thr Tyr Phe Cys Ala Arg
                85                  90                  95

Asp Asn Tyr Gly Met Asp Pro Trp Gly Pro Gly Thr Leu Val Thr Val
            100                 105                 110

Ser Ser
```

<210> SEQ ID NO 166
<211> LENGTH: 110
<212> TYPE: PRT
<213> ORGANISM: Artificial Sequence
<220> FEATURE:
<223> OTHER INFORMATION: P2-C12antibodyVL

<400> SEQUENCE: 166

```
Glu Leu Asp Met Thr Gln Thr Pro Ser Ser Val Ser Ala Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Ser Thr Asn
                85                  90                  95

Val Trp Asn Ala Phe Gly Gly Gly Thr Asn Val Glu Ile Lys
            100                 105                 110
```

<210> SEQ ID NO 167
<211> LENGTH: 106
<212> TYPE: PRT
<213> ORGANISM: Artificial Sequence
<220> FEATURE:
<223> OTHER INFORMATION: 13B4antibodyVL

<400> SEQUENCE: 167

```
Ser Tyr Glu Leu Thr Gln Pro Leu Ser Val Ser Val Ser Pro Gly Gln
1               5                   10                  15
```

```
Thr Ala Ser Ile Thr Cys Ser Gly Asp Lys Leu Gly Asn Val Tyr Ala
            20                  25                  30

Ser Trp Tyr Gln Gln Lys Pro Gly Gln Ser Pro Thr Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Lys Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 168
<211> LENGTH: 112
<212> TYPE: PRT
<213> ORGANISM: Artificial Sequence
<220> FEATURE:
<223> OTHER INFORMATION: 13F7antibodyVL

<400> SEQUENCE: 168

Asp Ile Val Met Thr Gln Thr Pro Leu Ser Leu Pro Val Ala Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Val Gln Lys Pro Gly Gln Pro
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Leu Thr Phe Gly Gly Gly Thr Lys Val Glu Ile Lys
            100                 105                 110

<210> SEQ ID NO 169
<211> LENGTH: 107
<212> TYPE: PRT
<213> ORGANISM: Artificial Sequence
<220> FEATURE:
<223> OTHER INFORMATION: 15A9antibodyVL

<400> SEQUENCE: 169

Asp Ile Gln Met Thr Gln Ser Pro Ser Ser Leu Ser Ala Ser Val Gly
1               5                   10                  15

Asp Arg Ile Thr Ile Ser Cys Arg Ala Ser Gln Ser Ile Ser Thr Ser
            20                  25                  30

Leu Asn Trp Tyr Gln Gln Thr Pro Gly Lys Ala Pro Arg Leu Leu Ile
        35                  40                  45

Tyr Gly Ala Ser Thr Leu Gln Ser Gly Val Pro Ser Arg Phe Ser Gly
    50                  55                  60

Gly Gly Ser Gly Thr Asp Phe Ser Leu Thr Ile Thr Ser Leu Gln Pro
65                  70                  75                  80

Glu Asp Phe Ala Thr Tyr Tyr Cys Gln Glu Ser Ala Ser Ile Pro Arg
                85                  90                  95

Thr Phe Gly Gln Gly Thr Lys Leu Asp Ile Lys
```

<210> SEQ ID NO 170
<211> LENGTH: 110
<212> TYPE: PRT
<213> ORGANISM: Artificial Sequence
<220> FEATURE:
<223> OTHER INFORMATION: P1-A03antibodyVL

<400> SEQUENCE: 170

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Pro Thr Leu Leu Ile
        35                  40                  45

Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Thr Gly Leu Thr Phe Gly Ala Gly Thr Asn Val Glu Ile Lys
            100                 105                 110

<210> SEQ ID NO 171
<211> LENGTH: 110
<212> TYPE: PRT
<213> ORGANISM: Artificial Sequence
<220> FEATURE:
<223> OTHER INFORMATION: P1-A08antibodyVL

<400> SEQUENCE: 171

Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
    50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Asn
                85                  90                  95

Tyr Gln Tyr Val Phe Gly Gly Gly Thr Gln Leu Thr Val Thr
            100                 105                 110

<210> SEQ ID NO 172
<211> LENGTH: 108
<212> TYPE: PRT
<213> ORGANISM: Artificial Sequence
<220> FEATURE:
<223> OTHER INFORMATION: P1-F02antibodyVL

<400> SEQUENCE: 172

Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

```
Ile Ser Trp Tyr Gln Gln Lys Pro Gly Lys Pro Thr Leu Leu Ile
            35                  40                  45

Tyr Gly Ala Ser Asn Leu Glu Ser Gly Val Pro Pro Arg Phe Ser Gly
 50                  55                  60

Ser Gly Ser Gly Thr Asp Tyr Thr Leu Thr Ile Gly Gly Val Gln Ala
 65                  70                  75                  80

Glu Asp Ala Ala Thr Tyr Tyr Cys Leu Gly Gly Tyr Ser Tyr Ser Ser
                 85                  90                  95

Ile Thr Phe Gly Ala Gly Thr Asn Val Glu Ile Lys
                100                 105
```

<210> SEQ ID NO 173
<211> LENGTH: 112
<212> TYPE: PRT
<213> ORGANISM: Artificial Sequence
<220> FEATURE:
<223> OTHER INFORMATION: P2-A01antibodyVL

<400> SEQUENCE: 173

```
Glu Leu Val Met Thr Gln Thr Pro Pro Ser Leu Ser Ala Ser Val Gly
 1               5                  10                  15

Glu Thr Val Arg Ile Arg Cys Leu Ala Ser Glu Asp Ile Tyr Ser Gly
                 20                  25                  30

Ile Ser Trp Tyr Gln Gln Lys Pro Gly Lys Pro Thr Leu Leu Ile
             35                  40                  45

Tyr Gly Ala Ser Asn Leu Glu Ser Gly Val Pro Pro Arg Phe Ser Gly
 50                  55                  60

Ser Gly Ser Gly Ser Asp Tyr Thr Leu Thr Ile Gly Gly Val Gln Ala
 65                  70                  75                  80

Glu Asp Ala Ala Thr Tyr Tyr Cys Leu Gly Gly Val Thr Tyr Ser Ser
                 85                  90                  95

Thr Gly Thr His Leu Thr Phe Gly Ala Gly Thr Asn Val Glu Ile Lys
                100                 105                 110
```

<210> SEQ ID NO 174
<211> LENGTH: 112
<212> TYPE: PRT
<213> ORGANISM: Artificial Sequence
<220> FEATURE:
<223> OTHER INFORMATION: P2-A03antibodyVL

<400> SEQUENCE: 174

```
Glu Leu Asp Leu Thr Gln Thr Pro Ala Ser Val Ser Glu Pro Val Gly
 1               5                  10                  15

Gly Thr Val Thr Ile Lys Cys Gln Ala Ser Gln Ser Ile Gly Gly Asn
                 20                  25                  30

Leu Ala Trp Tyr Gln Gln Lys Pro Gly Gln Pro Pro Lys Leu Leu Ile
             35                  40                  45

Tyr Arg Ala Ser Thr Leu Ala Ser Gly Val Pro Ser Arg Phe Lys Gly
 50                  55                  60

Ser Gly Ser Gly Thr Asp Phe Thr Leu Thr Ile Ser Asp Leu Glu Cys
 65                  70                  75                  80

Ala Asp Ala Ala Thr Tyr Tyr Cys Gln Ser Pro Ala Tyr Asp Pro Ala
                 85                  90                  95

Ala Tyr Val Gly Asn Ala Phe Gly Gly Gly Thr Glu Leu Glu Ile Leu
                100                 105                 110
```

<210> SEQ ID NO 175
<211> LENGTH: 107
<212> TYPE: PRT
<213> ORGANISM: Artificial Sequence
<220> FEATURE:
<223> OTHER INFORMATION: P2-F07antibodyVL

<400> SEQUENCE: 175

```
Glu Leu Asp Leu Thr Gln Thr Pro Pro Ser Leu Ser Ala Ser Val Gly
1               5                   10                  15
Gly Thr Val Thr Ile Asn Cys Leu Ala Ser Glu Asp Ile Tyr Ser Ala
            20                  25                  30
Leu Ala Trp Tyr Gln Gln Lys Pro Gly Lys Pro Thr Leu Leu Ile
        35                  40                  45
Ser Gly Thr Ser Asn Leu Glu Ser Gly Val Pro Pro Arg Phe Ser Gly
    50                  55                  60
Ser Gly Ser Gly Thr Asp Tyr Thr Leu Thr Ile Gly Gly Val Gln Ala
65                  70                  75                  80
Glu Asp Ala Ala Thr Tyr Phe Cys Gln Gly Tyr Ser Ser Tyr Pro Leu
                85                  90                  95
Thr Phe Gly Ala Gly Thr Asn Val Glu Ile Lys
            100                 105
```

<210> SEQ ID NO 176
<211> LENGTH: 113
<212> TYPE: PRT
<213> ORGANISM: Artificial Sequence
<220> FEATURE:
<223> OTHER INFORMATION: P2-F11antibodyVL

<400> SEQUENCE: 176

```
Glu Leu Asp Leu Thr Gln Thr Pro Ser Ser Val Ser Ala Ala Val Gly
1               5                   10                  15
Gly Thr Val Thr Ile Asn Cys Gln Ala Ser Gln Ser Val Tyr Asn Asn
            20                  25                  30
Lys Asn Leu Ala Trp Tyr Gln Gln Lys Pro Gly Gln Pro Pro Lys Leu
        35                  40                  45
Leu Ile Tyr Ala Ala Ser Thr Leu Ala Ser Gly Val Ser Ser Arg Phe
    50                  55                  60
Lys Gly Ser Gly Ser Gly Thr Gln Phe Thr Leu Thr Ile Ser Asp Val
65                  70                  75                  80
Gln Cys Asp Asp Ala Ala Thr Tyr Tyr Cys Gln Gly Glu Phe Ser Cys
                85                  90                  95
Ser Ser Ala Asp Cys Asn Ala Phe Gly Gly Thr Glu Leu Glu Ile
            100                 105                 110
Leu
```

<210> SEQ ID NO 177
<211> LENGTH: 363
<212> TYPE: DNA
<213> ORGANISM: Artificial Sequence
<220> FEATURE:
<223> OTHER INFORMATION: P2-C12antibodyVH

<400> SEQUENCE: 177

```
cagtcgctgg aggagtccgg gggtcgcctg gtcacgcctg ggacacccct gacactcacc      60
tgcaccgtct ctggattctc cctcagtacc tatgcagtga cctgggtccg ccaggctcca     120
gggaaggggc tggaatggat cggatacatt aattggcgtg gtgggacatc ctacgcgaac     180
```

```
tgggcgaaag gccgattcac catctccaaa acctcgtcga ccacggtgga tctgaaaatg      240
accagtccga caaccgagga cacggccacc tatttctgtg ccagagatgc tagtagtggt      300
gctgcttttg ggtcttacgg catggacccc tggggcccag ggaccctcgt caccgtctct      360
tca                                                                    363
```

<210> SEQ ID NO 178
<211> LENGTH: 330
<212> TYPE: DNA
<213> ORGANISM: Artificial Sequence
<220> FEATURE:
<223> OTHER INFORMATION: P2-C12antibodyVL

<400> SEQUENCE: 178

```
gagctcgata tgacccagac tccatcctcc gtgtctgcag ctgtgggagg cacagtcacc       60
atcaagtgcc aggccagtca gagcattagt agctacttat cctggtatca gcagaaacca      120
gggcagcctc ccaagctcct gatctatgaa gcatccaaac tggcctctgg ggtcccatcg      180
cggttcagcg gcagtggata tgggacagag ttcactctca ccatcagcga cctggagtgt      240
gccgatgctg ccacttacta ctgtcaacag ggttatagta gtactaatgt ttggaatgct      300
ttcggcggag gcaccaatgt ggaaatcaaa                                       330
```

<210> SEQ ID NO 179
<211> LENGTH: 451
<212> TYPE: PRT
<213> ORGANISM: Artificial Sequence
<220> FEATURE:
<223> OTHER INFORMATION: P2-C12HC

<400> SEQUENCE: 179

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
        35                  40                  45

Tyr Ile Asn Trp Arg Gly Gly Thr Ser Tyr Ala Asn Trp Ala Lys Gly
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Asp
                85                  90                  95

Ala Ser Ser Gly Ala Ala Phe Gly Ser Tyr Gly Met Asp Pro Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 180
<211> LENGTH: 448
<212> TYPE: PRT
<213> ORGANISM: Artificial Sequence
<220> FEATURE:
<223> OTHER INFORMATION: 13B4HC

<400> SEQUENCE: 180

Gln Val Gln Leu Gln Glu Ser Gly Pro Gly Leu Val Lys Pro Ser Gly
1               5                   10                  15

Thr Leu Ser Leu Asn Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Gly Gly Thr Thr Asn Tyr Asn Pro Ser Leu
    50                  55                  60

Lys Gly Arg Val Thr Met Ser Val Asp Lys Thr Lys Asn Gln Phe Ser
65                  70                  75                  80

Leu Arg Leu Ser Ser Val Thr Ala Val Asp Thr Ala Val Tyr Tyr Cys
                85                  90                  95

Ala Arg Trp Gln Leu Val Gly Gly Leu Asp Val Trp Gly Gln Gly Thr
            100                 105                 110

```
Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 181
<211> LENGTH: 453
<212> TYPE: PRT
<213> ORGANISM: Artificial Sequence
<220> FEATURE:
<223> OTHER INFORMATION: 13F7HC

<400> SEQUENCE: 181

Gln Val Gln Leu Gln Glu Trp Gly Ala Gly Leu Leu Lys Pro Ser Glu
1               5                   10                  15

Thr Leu Ser Leu Thr Cys Ala Ile Asn Ala Glu Ser Phe Asn Gly Tyr
            20                  25                  30
```

```
Ser Trp Thr Trp Ile Arg Gln Thr Pro Gly Lys Gly Leu Glu Trp Ile
         35                  40                  45

Gly Glu Ile Ser His Phe Gly Ser Ala Asn Tyr Asn Pro Ser Leu Lys
 50                  55                  60

Ser Arg Ala Thr Ile Ser Ala Asp Lys Ser Lys Asn Gln Phe Ser Leu
 65                  70                  75                  80

Lys Leu Thr Ser Val Thr Ala Val Asp Thr Ala Val Tyr Tyr Cys Ala
                 85                  90                  95

Arg Ala Leu Arg Gly Thr Tyr Ser Arg Phe Tyr Tyr Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
```

-continued

```
                            450

<210> SEQ ID NO 182
<211> LENGTH: 450
<212> TYPE: PRT
<213> ORGANISM: Artificial Sequence
<220> FEATURE:
<223> OTHER INFORMATION: 15A9HC

<400> SEQUENCE: 182

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Pro Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Lys Ser Val Thr Ala Val Asp Thr Ala Val Tyr Tyr Cys Ala
                85                  90                  95

Arg Val Asn Pro Phe Gly Tyr Tyr Ala Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                    355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 183
<211> LENGTH: 446
<212> TYPE: PRT
<213> ORGANISM: Artificial Sequence
<220> FEATURE:
<223> OTHER INFORMATION: P1-A03HC

<400> SEQUENCE: 183

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asp Tyr
                20                  25                  30

Met Ser Trp Val Arg Gln Ala Pro Gly Glu Gly Leu Glu Trp Ile Gly
            35                  40                  45

Ile Ile Tyr Pro Ser Thr Thr Thr Tyr Tyr Ala Ser Trp Ala Lys Gly
        50                  55                  60

Arg Phe Thr Ile Ser Lys Thr Ser Thr Thr Val Glu Leu Lys Met Thr
65                  70                  75                  80

Ser Leu Thr Thr Glu Asp Thr Ala Thr Tyr Phe Cys Ala Arg Gly Ser
                85                  90                  95

Asn Trp Ser Ser Gly Met Asn Leu Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val
```

```
            260                 265                 270
Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 184
<211> LENGTH: 443
<212> TYPE: PRT
<213> ORGANISM: Artificial Sequence
<220> FEATURE:
<223> OTHER INFORMATION: P1-A08HC

<400> SEQUENCE: 184

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ile Val Tyr Pro Ser Gly Thr Thr Tyr Tyr Ala Asn Trp Ala Lys Gly
    50                  55                  60

Arg Phe Thr Ile Ser Thr Ala Ser Thr Thr Val Asp Leu Met Ile Thr
65                  70                  75                  80

Ser Pro Thr Thr Glu Asp Thr Ala Thr Tyr Phe Cys Ala Arg Gly Asp
                85                  90                  95

Ser Phe Gly Tyr Gly Leu Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
```

```
                180             185                 190
Thr Tyr Ile Cys Asn Val Asn His Lys Pro Ser Asn Thr Lys Val Asp
            195                 200                 205
Lys Lys Val Glu Pro Lys Ser Cys Asp Lys Thr His Thr Cys Pro Pro
        210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440

<210> SEQ ID NO 185
<211> LENGTH: 452
<212> TYPE: PRT
<213> ORGANISM: Artificial Sequence
<220> FEATURE:
<223> OTHER INFORMATION: P1-F02HC

<400> SEQUENCE: 185

Gln Ser Leu Glu Glu Ser Gly Gly Arg Leu Val Thr Pro Gly Thr Pro
1               5                   10                  15
Leu Thr Leu Thr Cys Thr Ala Ser Gly Phe Ser Leu Ser Asn Tyr Tyr
            20                  25                  30
Met Gly Trp Val Arg Gln Ala Pro Gly Glu Gly Leu Glu Trp Ile Gly
        35                  40                  45
Ile Ile Tyr Ala Ser Gly Ser Thr Tyr Tyr Ala Ser Trp Ala Lys Gly
    50                  55                  60
Arg Phe Thr Ile Ser Lys Thr Ser Thr Thr Val Asp Leu Lys Met Thr
65                  70                  75                  80
Ser Leu Thr Thr Glu Asp Thr Ala Thr Tyr Phe Cys Ala Arg Ile Asp
                85                  90                  95
Ile Gly Val Gly Asp Tyr Gly Trp Ala Tyr Asp Arg Leu Asp Leu Trp
```

```
            100                 105                 110
Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 186
<211> LENGTH: 451
<212> TYPE: PRT
<213> ORGANISM: Artificial Sequence
<220> FEATURE:
<223> OTHER INFORMATION: P2-A01HC

<400> SEQUENCE: 186

Gln Glu Gln Leu Val Glu Ser Gly Gly Arg Leu Val Thr Pro Gly Thr
```

-continued

```
1               5                   10                  15
Pro Leu Thr Leu Ser Cys Thr Ala Ser Gly Phe Phe Leu Ser Gly Tyr
                20                  25                  30

Tyr Met Ser Trp Val Arg Gln Ala Pro Gly Lys Gly Leu Glu Trp Ile
            35                  40                  45

Gly Ile Ile Tyr Pro Ser Gly Ser Thr Asp Tyr Ala Ser Trp Ala Lys
        50                  55                  60

Gly Arg Phe Thr Ile Ser Lys Thr Ser Thr Val Asp Leu Lys Ile
65                  70                  75                  80

Thr Thr Pro Thr Thr Glu Asp Thr Ala Thr Tyr Phe Cys Ala Arg Val
                85                  90                  95

Ala Gly Tyr Val Gly Tyr Gly Tyr Glu Thr Phe Phe Asp Ile Trp Gly
                100                 105                 110

Pro Gly Thr Leu Val Thr Val Ser Leu Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly Lys
    450

<210> SEQ ID NO 187
<211> LENGTH: 446
<212> TYPE: PRT
<213> ORGANISM: Artificial Sequence
<220> FEATURE:
<223> OTHER INFORMATION: P2-A03HC

<400> SEQUENCE: 187

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
                20                  25                  30

Met Ser Trp Val Arg Gln Ala Pro Gly Lys Gly Leu Glu Tyr Ile Gly
            35                  40                  45

Phe Met Asp Thr Asp Gly Ser Ala Tyr Tyr Ala Thr Trp Ala Lys Gly
    50                  55                  60

Arg Phe Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg Arg Gly
                85                  90                  95

Ser Ser Tyr Tyr Gly Gly Ile Asp Ile Trp Gly Pro Gly Thr Pro Val
            100                 105                 110

Thr Val Ser Leu Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

-continued

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 188
<211> LENGTH: 443
<212> TYPE: PRT
<213> ORGANISM: Artificial Sequence
<220> FEATURE:
<223> OTHER INFORMATION: P2-F07HC

<400> SEQUENCE: 188

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
                20                  25                  30

Met Asn Trp Val Arg Gln Ala Pro Gly Lys Gly Leu Glu Trp Ile Gly
            35                  40                  45

Ile Ile Tyr Pro Ser Gly Thr Thr Tyr Tyr Ala Gly Trp Ala Lys Gly
        50                  55                  60

Arg Phe Thr Ile Ser Lys Thr Ser Thr Val Asp Leu Lys Ile Thr
65                  70                  75                  80

Ser Pro Thr Ser Glu Asp Thr Ala Thr Tyr Phe Cys Ala Arg Thr Val
                85                  90                  95

Ser Gly Tyr Phe Asp Ile Trp Gly Pro Gly Thr Leu Val Thr Val Ser
                100                 105                 110

Leu Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
        210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

```
Cys Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
        435                 440

<210> SEQ ID NO 189
<211> LENGTH: 444
<212> TYPE: PRT
<213> ORGANISM: Artificial Sequence
<220> FEATURE:
<223> OTHER INFORMATION: P2-F11HC

<400> SEQUENCE: 189

Gln Glu Gln Leu Val Glu Ser Gly Gly Arg Leu Val Thr Pro Gly Thr
1               5                   10                  15

Thr Leu Thr Leu Thr Cys Thr Val Ser Gly Phe Ser Leu Ser Ser Tyr
                20                  25                  30

Gly Val Ser Trp Val Arg Gln Ala Pro Gly Lys Gly Leu Glu Trp Ile
            35                  40                  45

Gly Tyr Ile Ala Asn Asn Tyr Asn Pro His Tyr Ala Ser Trp Ala Lys
        50                  55                  60

Gly Arg Phe Thr Ile Ser Lys Thr Ser Thr Thr Val Asp Leu Lys
65                  70                  75                  80

Met Thr Ser Leu Thr Thr Glu Asp Thr Ala Thr Tyr Phe Cys Ala Arg
                85                  90                  95

Asp Asn Tyr Gly Met Asp Pro Trp Gly Pro Gly Thr Leu Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175
```

```
Tyr Ser Leu Ser Ser Val Val Thr Val Pro Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 190
<211> LENGTH: 217
<212> TYPE: PRT
<213> ORGANISM: Artificial Sequence
<220> FEATURE:
<223> OTHER INFORMATION: P2-C12LC

<400> SEQUENCE: 190

Glu Leu Asp Met Thr Gln Thr Pro Ser Ser Val Ser Ala Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Thr Ser Asn
                85                  90                  95
```

Val Trp Asn Ala Phe Gly Gly Thr Asn Val Glu Ile Lys Arg Ser
            100                 105                 110

Val Ala Ala Pro Ser Val Phe Ile Phe Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 191
<211> LENGTH: 213
<212> TYPE: PRT
<213> ORGANISM: Artificial Sequence
<220> FEATURE:
<223> OTHER INFORMATION: 13B4LC

<400> SEQUENCE: 191

Ser Tyr Glu Leu Thr Gln Pro Leu Ser Val Ser Val Ser Pro Gly Gln
1               5                   10                  15

Thr Ala Ser Ile Thr Cys Ser Gly Asp Lys Leu Gly Asn Val Tyr Ala
            20                  25                  30

Ser Trp Tyr Gln Gln Lys Pro Gly Gln Ser Pro Thr Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Lys Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Arg Ser Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 192

```
<211> LENGTH: 219
<212> TYPE: PRT
<213> ORGANISM: Artificial Sequence
<220> FEATURE:
<223> OTHER INFORMATION: 13F7LC

<400> SEQUENCE: 192

Asp Ile Val Met Thr Gln Thr Pro Leu Ser Leu Pro Val Ala Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Val Gln Lys Pro Gly Gln Pro
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Leu Thr Phe Gly Gly Gly Thr Lys Val Glu Ile Lys
            100                 105                 110

Arg Ser Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 193
<211> LENGTH: 214
<212> TYPE: PRT
<213> ORGANISM: Artificial Sequence
<220> FEATURE:
<223> OTHER INFORMATION: 15A9LC

<400> SEQUENCE: 193

Asp Ile Gln Met Thr Gln Ser Pro Ser Ser Leu Ser Ala Ser Val Gly
1               5                   10                  15

Asp Arg Ile Thr Ile Ser Cys Arg Ala Ser Gln Ser Ile Ser Thr Ser
            20                  25                  30

Leu Asn Trp Tyr Gln Gln Thr Pro Gly Lys Ala Pro Arg Leu Leu Ile
        35                  40                  45

Tyr Gly Ala Ser Thr Leu Gln Ser Gly Val Pro Ser Arg Phe Ser Gly
    50                  55                  60

Gly Gly Ser Gly Thr Asp Phe Ser Leu Thr Ile Thr Ser Leu Gln Pro
65                  70                  75                  80

Glu Asp Phe Ala Thr Tyr Tyr Cys Gln Glu Ser Ala Ser Ile Pro Arg
                85                  90                  95

Thr Phe Gly Gln Gly Thr Lys Leu Asp Ile Lys Arg Ser Val Ala Ala
```

```
                100              105              110
Pro Ser Val Phe Ile Phe Pro Pro Ser Asp Glu Gln Leu Lys Ser Gly
        115                  120                  125

Thr Ala Ser Val Val Cys Leu Leu Asn Asn Phe Tyr Pro Arg Glu Ala
        130                  135              140

Lys Val Gln Trp Lys Val Asp Asn Ala Leu Gln Ser Gly Asn Ser Gln
145                  150                  155                  160

Glu Ser Val Thr Glu Gln Asp Ser Lys Asp Ser Thr Tyr Ser Leu Ser
                165                  170                  175

Ser Thr Leu Thr Leu Ser Lys Ala Asp Tyr Glu Lys His Lys Val Tyr
            180                  185                  190

Ala Cys Glu Val Thr His Gln Gly Leu Ser Ser Pro Val Thr Lys Ser
        195                  200                  205

Phe Asn Arg Gly Glu Cys
    210

<210> SEQ ID NO 194
<211> LENGTH: 217
<212> TYPE: PRT
<213> ORGANISM: Artificial Sequence
<220> FEATURE:
<223> OTHER INFORMATION: P1-A03LC

<400> SEQUENCE: 194

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Pro Thr Leu Leu Ile
        35                  40                  45

Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Thr Gly Leu Thr Phe Gly Ala Gly Thr Asn Val Glu Ile Lys Arg Ser
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 195
<211> LENGTH: 217
<212> TYPE: PRT
```

<213> ORGANISM: Artificial Sequence
<220> FEATURE:
<223> OTHER INFORMATION: P1-A08LC

<400> SEQUENCE: 195

```
Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Asn
                85                  90                  95

Tyr Gln Tyr Val Phe Gly Gly Thr Gln Leu Thr Val Thr Arg Ser
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
        210                 215
```

<210> SEQ ID NO 196
<211> LENGTH: 215
<212> TYPE: PRT
<213> ORGANISM: Artificial Sequence
<220> FEATURE:
<223> OTHER INFORMATION: P1-F02LC

<400> SEQUENCE: 196

```
Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
        35                  40                  45

Tyr Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Ile Thr Phe Gly Ala Gly Thr Asn Val Glu Ile Lys Arg Ser Val Ala
            100                 105                 110
```

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 197
<211> LENGTH: 219
<212> TYPE: PRT
<213> ORGANISM: Artificial Sequence
<220> FEATURE:
<223> OTHER INFORMATION: P2-A01LC

<400> SEQUENCE: 197

Glu Leu Val Met Thr Gln Thr Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Thr Leu Leu Ile
            35                  40                  45

Tyr Gly Ala Ser Asn Leu Glu Ser Gly Val Pro Pro Arg Phe Ser Gly
    50                  55                  60

Ser Gly Ser Gly Ser Asp Tyr Thr Leu Thr Ile Gly Gly Val Gln Ala
65                  70                  75                  80

Glu Asp Ala Ala Thr Tyr Tyr Cys Leu Gly Gly Val Thr Tyr Ser Ser
                85                  90                  95

Thr Gly Thr His Leu Thr Phe Gly Ala Gly Thr Asn Val Glu Ile Lys
            100                 105                 110

Arg Ser Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 198
<211> LENGTH: 219
<212> TYPE: PRT
<213> ORGANISM: Artificial Sequence
<220> FEATURE:

<223> OTHER INFORMATION: P2-A03LC

<400> SEQUENCE: 198

Glu Leu Asp Leu Thr Gln Thr Pro Ala Ser Val Ser Glu Pro Val Gly
1               5                   10                  15

Gly Thr Val Thr Ile Lys Cys Gln Ala Ser Gln Ser Ile Gly Gly Asn
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Pro Ser Arg Phe Lys Gly
50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Pro Ala Tyr Asp Pro Ala
                85                  90                  95

Ala Tyr Val Gly Asn Ala Phe Gly Gly Gly Thr Glu Leu Glu Ile Leu
                100                 105                 110

Arg Ser Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 199
<211> LENGTH: 214
<212> TYPE: PRT
<213> ORGANISM: Artificial Sequence
<220> FEATURE:
<223> OTHER INFORMATION: P2-F07LC

<400> SEQUENCE: 199

Glu Leu Asp Leu Thr Gln Thr Pro Pro Ser Leu Ser Ala Ser Val Gly
1               5                   10                  15

Gly Thr Val Thr Ile Asn Cys Leu Ala Ser Glu Asp Ile Tyr Ser Ala
                20                  25                  30

Leu Ala Trp Tyr Gln Gln Lys Pro Gly Lys Pro Pro Thr Leu Leu Ile
            35                  40                  45

Ser Gly Thr Ser Asn Leu Glu Ser Gly Val Pro Pro Arg Phe Ser Gly
50                  55                  60

Ser Gly Ser Gly Thr Asp Tyr Thr Leu Thr Ile Gly Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 200
<211> LENGTH: 220
<212> TYPE: PRT
<213> ORGANISM: Artificial Sequence
<220> FEATURE:
<223> OTHER INFORMATION: P2-F11LC

<400> SEQUENCE: 200

Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Ser Cys
                85                  90                  95

Ser Ser Ala Asp Cys Asn Ala Phe Gly Gly Gly Thr Glu Leu Glu Ile
                100                 105                 110

Leu Arg Ser Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 201
<211> LENGTH: 18
<212> TYPE: PRT
<213> ORGANISM: Artificial Sequence
<220> FEATURE:
<223> OTHER INFORMATION: Synthetic Peptide KLH conjugate
```

```
<400> SEQUENCE: 201

Val Thr Leu Asp Arg Asp Ser Ser Gln Pro Arg Arg Thr Ile Ala Arg
1               5                   10                  15

Gln Thr
```